United States Patent [19]
Urata et al.

[11] Patent Number: 5,910,619
[45] Date of Patent: Jun. 8, 1999

[54] PROCESS FOR PRODUCING α-OLEFIN OLIGOMERS

[75] Inventors: Hisao Urata; Takayuki Aoshima, both of Yokohama; Toshiyuki Oshiki, Ikeda; Jun Takahara, Yokohama; Shinji Iwade, Kurashiki; Yoshiaki Nanba, Kurashiki; Yoshitaka Araki, Kurashiki; Hirofumi Nakamura, Kurashiki; Takeshi Okano, Kurashiki, all of Japan

[73] Assignee: Mitsubishi Chemical Corporation, Japan

[21] Appl. No.: 08/493,234

[22] Filed: Jun. 20, 1995

[30] Foreign Application Priority Data

| | | | |
|---|---|---|---|
| Jun. 21, 1994 | [JP] | Japan | 6-139024 |
| Sep. 13, 1994 | [JP] | Japan | 6-218477 |
| Mar. 2, 1995 | [JP] | Japan | 7-068598 |
| Mar. 2, 1995 | [JP] | Japan | 7-068599 |

[51] Int. Cl.⁶ .............. C07C 2/24; C07C 2/26
[52] U.S. Cl. .......... 585/513; 585/571; 585/512; 585/500; 585/502; 585/520; 585/521; 585/523; 585/527; 585/530
[58] Field of Search .......... 585/511, 512, 585/513, 500, 502, 520, 521, 523, 527, 530

[56] References Cited

U.S. PATENT DOCUMENTS

| | | | |
|---|---|---|---|
| 3,347,840 | 10/1967 | Manyik et al. | 526/169 |
| 4,668,838 | 5/1987 | Briggs | 585/513 |
| 4,853,356 | 8/1989 | Briggs | 502/117 |
| 5,198,563 | 3/1993 | Reagen et al. | 556/57 |
| 5,288,823 | 2/1994 | Reagen et al. | 526/124 |
| 5,376,612 | 12/1994 | Reagen et al. | 502/104 |
| 5,491,272 | 2/1996 | Tanaka et al. | 585/520 |
| 5,523,507 | 6/1996 | Reagen et al. | 585/513 |

FOREIGN PATENT DOCUMENTS

| | | |
|---|---|---|
| 0 237 079 | 9/1987 | European Pat. Off. . |
| 0 417 477 A2 | 3/1991 | European Pat. Off. . |
| 0 537 609 A2 | 4/1993 | European Pat. Off. . |
| 0 608 447 A1 | 8/1994 | European Pat. Off. . |
| 0 611 743 A2 | 8/1994 | European Pat. Off. . |
| 0614865 A1 | 9/1994 | European Pat. Off. . |
| 6263822 | 9/1994 | Japan . |
| 6-329562 | 11/1994 | Japan . |
| 7-10780 | 1/1995 | Japan . |
| 7017878 | 1/1995 | Japan . |
| 7018013 | 1/1995 | Japan . |
| 2 271 116 | 4/1994 | United Kingdom . |

*Primary Examiner*—Elizabeth D Wood
*Attorney, Agent, or Firm*—Nixon & Vanderhye

[57] ABSTRACT

The disclosure described a process for producing an α-olefin oligomer, which comprises carrying out oligomerization of an α-olefin in a solvent in the presence of a catalytically effective amount of a chromium-based catalyst system composed of a combination of at least (a) a chromium compound, (b) a nitrogen-containing compound of at least one selected from the group consisting of an amine, an amide and an imide, (c) an alkylaluminum compound and (d) a halogen-containing compound, wherein each of the α-olefin, the chromium compound (a), the nitrogen-containing compound (b) of at least one selected from the group consisting of an amine, an amide and an imide, the alkylaluminum compound (c) and the halogen-containing compound (d) is supplied to a reaction system in a mode that the chromium compound (a) and the alkylaluminum compound (c) do not contact each other before each of said compounds (a) to (d) and the α-olefin coexists in the reaction solvent and the oligomerization of an α-olefin takes place.

35 Claims, 1 Drawing Sheet

PROCESS FOR PRODUCING α-OLEFIN OLIGOMERS

BACKGROUND OF THE INVENTION

The present invention relates to a process for preparing α-olefin oligomers. More particularly, it relates to an industrially advantageous process of formation of α-olefin oligomers in which it is possible to produce α-olefin oligomers principally composed of 1-hexene from ethylene with a high selectivity and in a high yield.

As an oligomerization process of α-olefins such as ethylene, etc., methods are known in which a chromium-based catalyst composed of a specific chromium compound and a specific organoaluminum compound is used as a catalyst. For instance, Japanese Patent Publication (KOKOKU) No. 43-18707 discloses a process for producing 1-hexene from ethylene by using a catalyst consisting of a chromium-containing VIB Group transition metal compound and a polyhydrocarbylaluminum oxide.

Also, in Japanese Patent Application Laid-Open (KOKAI) No. 3-128904 is disclosed a method for oligomerizing α-olefins by using a catalyst obtained by reacting a chromium-containing compound having chromium-pyrrolyl bond with an alkyl metal or a Lewis acid. South Africa Patent Publication ZA93/0350 describes a process for producing an α-olefin oligomer using a catalyst system obtained by mixing a chromium compound, a pyrrole-containing compound, a metal alkyl compound and a halide source in a mutual solvent.

However, according to the process of Japanese KOKOKU No. 43-18707, the amount of the by-product polyethylene which is produced with 1-hexene is large, and if such reaction is carried out under the conditions which decrease yield of the by-product polyethylene, the catalyst activity is lowered.

Also, the method of Japanese KOKAI No. 3-128904 has the problem that the activity of the catalyst is unsatisfactory, although the yield of the by-products such as polyethylene, etc. is low. Further, in this method, there are required, in addition to the α-olefin oligomerization process, a step for preparing a chromium-containing compound at least having chromium-pyrrolyl bond from a chromium salt and metal pyrrolide, and a step for isolating the said chromium-containing compound, so that not only the oligomerization operations become too complicated but also the construction cost for the whole process is elevated. Moreover, it is very difficult to handle the chromium-containing compounds at least having chromium-pyrrolyl bond, since they are very sensitive to air and to moisture.

South Africa Patent ZA93/0350 discloses that when an unsaturated hydrocarbon for improving a stability of the catalyst system is present in excess, the selectivity and/or activity of the catalyst are lowered. Also, the process described in South Africa Patent ZA93/0350 is defective in that since it also requires a preliminary preparation process of an unstable catalyst and an isolation process of the catalyst, the operation is not only complicated but also requires a high construction cost for the entire process.

As a result of the present inventors' earnest studies in order to solve the above-mentioned problems, it has been found that by carrying out oligomerization of an α-olefin in a reaction solvent by reacting the α-olefin in a catalytically effective amount of a chromium-based catalyst system comprising a combination of at least a chromium compound, a nitrogen-containing compound of at least one selected from the group consisting of an amine, an amide and an imide, an alkylaluminum compound and a halogen-containing compound, in a contacting mode that the chromium compound is not contacted with the alkylaluminum compound each other before each of the chromium compound, the nitrogen-containing compound of at least one selected from the group consisting of an amine, an amide and an imide, the alkylaluminum compound and the halogen-containing compound and α-olefin coexist in the reaction solvent, and the oligomerization of α-olefin takes place, α-olefin oligomers are obtained in a high yield. On the basis of this finding, the present invention has been attained.

SUMMARY OF THE INVENTION

It is an object of the present invention to provide a process for producing an α-olefin oligomer in which it is possible to prepare an α-olefin oligomer such as 1-hexene in a high selectivity and in a high yield without requiring any complicated operations.

It is another object of the present invention to provide a process for producing an α-olefin oligomer which realizes the activation of a catalyst in a reaction system.

To achieve these ends, in a first aspect of the present invention, there is provided a process for producing an α-olefin oligomer, which comprises carrying out oligomerization of an α-olefin in a solvent in the presence of a catalytically effective amount of a chromium-based catalyst system composed of a combination of at least (a) a chromium compound, (b) a nitrogen-containing compound of at least one selected from the group consisting of an amine, an amide and an imide, (c) an alkylaluminum compound and (d) a halogen-containing compound, wherein each of the α-olefin, the chromium compound (a), the nitrogen-containing compound (b) of at least one selected from the group consisting of an amine, an amide and an imide, the alkylaluminum compound (c) and the halogen-containing compound (d) is supplied to a reaction system in a mode that the chromium compound (a) and the alkylaluminum compound (c) do not contact each other before each of said compounds (a) to (d) and the α-olefin coexists in the reaction solvent and the oligomerization of an α-olefin takes place. According to the said process of the present invention, it is not necessary to conduct a formation of the chromium-based catalyst.

In a second aspect of the present invention, there is provided a process for producing an α-olefin oligomer, which comprises carrying out oligomerization of an α-olefin in a solvent in the presence of a chromium-based catalyst system composed of a combination of at least (a) a chromium compound, (b) a nitrogen-containing compound of at least one selected from the group consisting of an amine, an amide and an imide, (c) an alkylaluminum compound and (d) a halogen-containing compound, wherein catalyst components composed of at least the alkylaluminum compound (c) and the halogen-containing compound (d) without the chromium compound (a), are heated to not lower than 100° C. in a reaction solvent in advance and the treated catalyst components are contacted with the rest of the catalyst components and the α-olefin in the reaction solvent.

In a third aspect of the present invention, there is provided a process for producing an α-olefin oligomer, which comprises carrying out oligomerization of an α-olefin in a reaction solvent in the presence of a chromium-based catalyst system composed of a combination of at least (a) a chromium compound, (b) a nitrogen-containing compound of at least one selected from the group consisting of an amine, an amide and an imide, (c) an alkylaluminum compound and (d) a halogen-containing compound, wherein the oligomerization of the α-olefin in a reaction solvent is conducted by a semi-batch process or by a continuous process, and at least one catalyst component selected from the group consisting of the nitrogen-containing compound(b), the alkylaluminum compound (c) and the halogen-containing compound (d) is added as supplement to a reaction system.

DETAILED DESCRIPTION OF THE INVENTION

Figure 1:
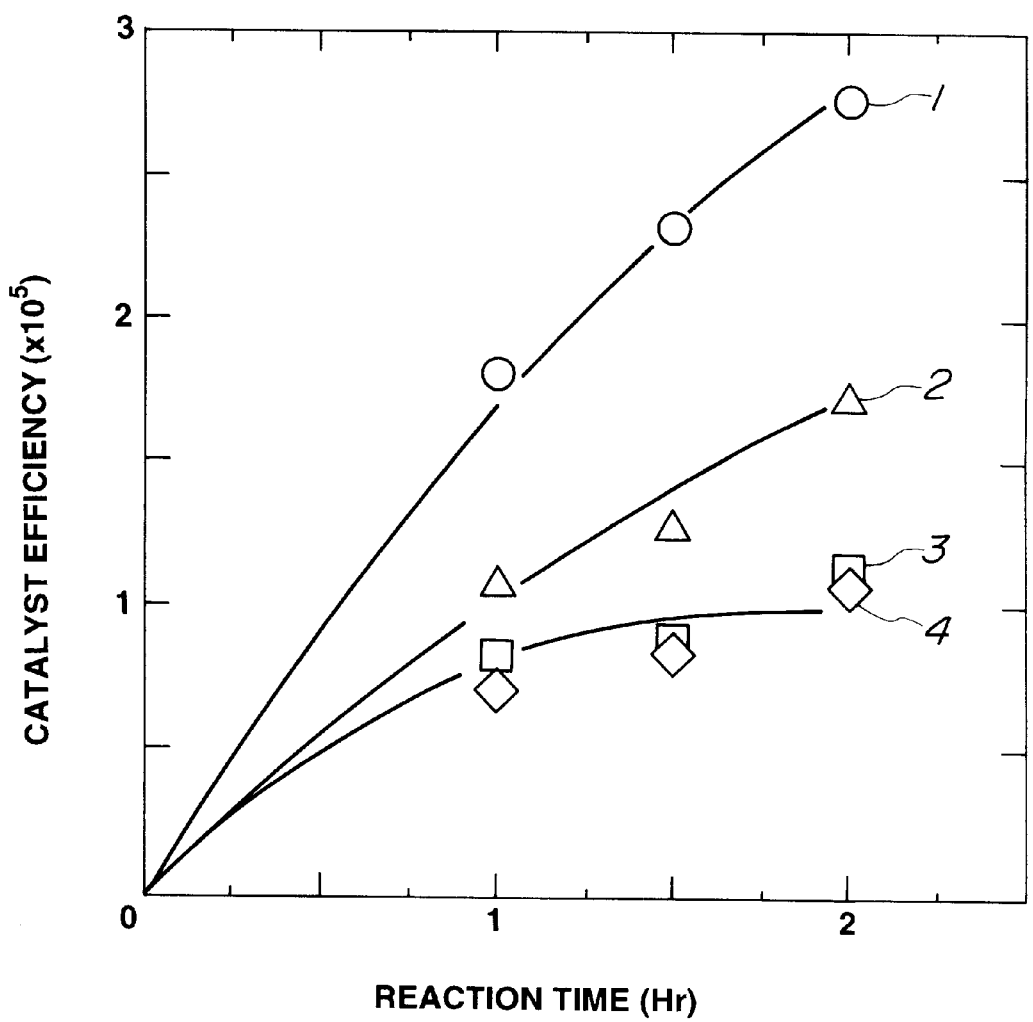
FIG. 1 shows a change of the catalytic efficiency with passage of time.

In the present invention, a catalyst comprising a combination of at least (a) a chromium compound, (b) a nitrogen-containing compound of at least one selected from the group consisting of an amine, an amide and an imide, (c) an alkylaluminum compound and (d) a halogen-containing compound is used as chromium-based catalyst.

The chromium compound (a) used in the present invention is represented by the formula: $CrX_n$, wherein X is an organic group, an inorganic group or an anionic atom; n is an integer of 1 to 6, and when n is not less than 2, X may be the same or different from each other. The valency of chromium is 0 to 6. Also, n in the above formula is preferably not less than 2.

The organic groups represented by X in the above formula include various kinds of groups having usually 1 to 30 carbon atoms. Typical examples of such organic groups having 1 to 30 carbon atoms are hydrocarbon groups, carbonyl groups, alkoxy groups, carboxyl groups, β-diketonate groups, β-ketocarboxyl groups, β-ketoester groups and amide groups. As the hydrocarbon groups having 1 to 30 carbon atoms, an alkyl group, a cycloalkyl group, an aryl group, an alkylaryl group, an aralkyl group and a cyclopentadienyl group may be exemplified. The inorganic groups include chromium salt-forming groups such as nitrate group and sulfate group. The anionic (negative) atoms include oxygen and halogens.

The preferred chromium compounds used in the present invention are chromium alkoxides, chromium carboxylates, chromium β-diketonates, salts of chromium with anions of β-ketoesters, and chromium halides. Specifically, chromium (IV) tert-butoxide, chromium (III) acetylacetonate, chromium (III) trifluoroacetylacetonate, chromium (III) hexafluoroacetylacetonate, chromium (III) (2,2,6,6-tetramethyl-3,5-heptanedionate), $Cr(PhCOCHCOPh)_3$ (wherein Ph represents phenyl group), chromium (II) acetate, chromium (III) acetate, chromium (III) 2-ethylhexanoate, chromium (III) benzoate, chromium (III) naphthenate, $Cr(CH_3COCHCOOCH_3)_3$, chromous chloride, chromic chloride, chromous bromide, chromic bromide, chromous iodide, chromic iodide, chromous fluoride and chromic fluoride may be exemplified.

Complexes composed of the above-mentioned chromium compounds and an electron donor can also be favorably used in the present invention. As the electron donor, a nitrogen-containing compound, an oxygen-containing compound, a phosphorus-containing compound and a sulfur-containing compound may be cited.

The nitrogen-containing compounds include nitriles, amines and amides. As typical examples thereof, acetonitrile, pyridine, dimethylpyridine, dimethylformamide, N-methylformamide, aniline, nitrobenzene, tetramethylethylenediamine, diethylamine, isopropylamine, hexamethyldisilazane and pyrrolidone may be exemplified.

The oxygen-containing compounds include esters, ethers, ketones, alcohols and aldehydes. As typical examples thereof, ethyl acetate, methyl acetate, tetrahydrofuran, dioxane, diethyl ether, dimethoxyethane, diethylene glycol dimethyl ether, triethylene glycol dimethyl ether, acetone, methyl ethyl ketone, methanol, ethanol and acetaldehyde may be exemplified.

As the phosphorus-containing compounds, hexamethylphosphoramide, hexamethyl phosphorus triamide, triethyl phosphite, tributylphosphine oxide and triethylphosphine may be exemplified.

As the sulfur-containing compounds, carbon disulfide, dimethyl sulfoxide, tetramethylene sulfone, thiophene and dimethyl sulfide may be exemplified.

Thus, as the complexes composed of chromium compounds and an electron donor, ether complexes, ester complexes, ketone complexes, aldehyde complexes, alcohol complexes, amine complexes, nitrile complexes, phosphine complexes and thioether complexes of chromium halides can be cited. More specifically, $CrCl_3 \cdot 3THF$, $CrCl_3 \cdot 3dioxane$, $CrCl_3 \cdot (CH_3CO_2n\text{-}C_4H_9)$, $CrCl_3 \cdot (CH_3CO_2C_2H_5)$, $CrCl_3 \cdot 3(i\text{-}C_3H_7OH)$, $CrCl_3 \cdot 3[CH_3(CH_2)_3CH(C_2H_5)CH_2OH]$, $CrCl_3 \cdot 3pyridine$, $CrCl_3 \cdot 2(i\text{-}C_3H_7NH_2)$, $[CrCl_3 \cdot 3CH_3CN] \cdot CH_3CN$, $CrCl_3 \cdot 3PPh_3$, $CrCl_2 2THF$, $CrCl_2 \cdot 2pyridine$, $CrCl_2 \cdot 2[(C_2H_5)_2NH]$, $CrCl_2 \cdot 2CH_3CN$ and $CrCl_2 \cdot 2[P(CH_3)2Ph]$ may be exemplified.

The chromium compound used in the present invention is preferably one which is soluble in hydrocarbon solvents. Examples of such chromium compounds are chromium β-diketonates, chromium carboxylates, salts of chromium with anions of β-ketoesters, chromium β-ketocarboxylates, chromium amide complexes, chromium carbonyl complexes, chromium carbene complexes, various kinds of cyclopentadienyl complexes of chromium, chromium alkyl complexes and chromium phenyl complexes. As specific examples thereof, $Cr(CO)_6$, $(C_6H_6)Cr(CO)_3$, $(CO)_5Cr(=CCH_3(OCH_3))$, $(CO)_5Cr(=CC_6H_5(OCH_3))$, $CpCrCl_2$ (wherein Cp represents a cyclopentadienyl group), $(Cp^*CrClCH_3)_2$ (wherein Cp* represents a pentamethylcyclopentadienyl group) and $(CH_3)_2CrCl$ may be exemplified.

The chromium compound can be used in the form supported on a carrier such as an inorganic oxide, but it is preferably used in combination with other catalyst components without being supported on a carrier. In the present invention, the chromium-based catalyst is used in a specific contacting mode described later, and according to such contacting mode of process, it is possible to obtain a high catalyst activity, even if the chromium compound is not supported on a carrier. When the chromium compound is used without supporting it on a carrier, it is possible to dispense with the complicated operations required for supporting the chromium compound on a carrier and to avoid the problem of increase of the whole amount of the catalyst used (the total amount of carrier and catalyst components combined) due to use of a carrier.

The nitrogen-containing compound (b) used in the present invention is a compound of at least one selected from the group consisting of an amine, an amide and an imide.

The amine used in the present invention is a primary or secondary amine. As the primary amines usable in the present invention, ammonia, ethylamine, isopropylamine, cyclohexylamine, benzylamine, aniline and naphthylamine may be exemplified. As the secondary amines usable in the present invention, diethylamine, diisopropylamine, dicyclohexylamine, dibenzylamine, bis(trimethylsilyl) amine, morpholine, imidazole, indoline, indol, pyrrole, 2,5-dimethylpyrrole, 3,4-dimethylpyrrole, 3,4-diethylpyrrole, 2,3,4-trimethylpyrrole, 3,4-dichloropyrrole, 2,3,4,5-tetrachloropyrrole, 2-acylpyrrole, 3,3',4,4'-tetramethyldipyrrolomethane, pyrazole and pyrrolidine may be exemplified. As the amine used in the present invention, a mixture of a primary amine and a secondary amine may be used.

The metal amide used in the present invention is one derived from a primary or secondary amine. Specifically, an amide obtained from the reaction of a primary or secondary amine and a metal selected from the group consisting of IA, IIA, IIIA and IVB Groups in the periodic table is usable. As such metal amides, lithium amide, sodium ethylamide, calcium diethylamide, lithium diisopropylamide, potassium benzylamide, sodium bis(trimethylsilyl)amide, lithium indolide, sodium pyrrolide, lithium pyrrolide, potassium pyrrolide, potassium pyrrolidide, diethylaluminum pyrrolide, ethylaluminum dipyrrolide, aluminum tripyrrolide and lithium (2,5-dimethylpyrrolide) may be exemplified.

The metal amide in the present invention may be a mixture of metal amides which are induced from primary or secondary amines.

In the present invention, a secondary amine, a metal amide derived from a secondary amine or a mixture thereof is preferably used. As preferred examples of the secondary amines used in the present invention, pyrrole, 2,5-dimethylpyrrole, 3,4-dimethylpyrrole, 2,3,4-trimethylpyrrole, 3,4-dichloropyrrole, 2,3,4,5-tetrachloropyrrole, 2-acylpyrrole and 3,3',4,4'-tetramethyldipyrrolomethane may be exemplified. Among them, pyrrole and 2,5-dimethylpyrrole are especially preferred. As preferred examples of the metal amides derived from the secondary amines, aluminum pyrrolide, ethylaluminum dipyrrolide, aluminum tripyrrolide, sodium pyrrolide, lithium pyrrolide, potassium pyrrolide, aluminum (2,5-dimethylpyrrolide), ethylaluminum bis(2,5-dimethylpyrrolide), aluminum tris(2,5-dimethylpyrrolide), sodium (2,5-dimethylpyrrolide), lithium (2,5-dimethylpyrrolide) and potassium (2,5-dimethylpyrrolide) may be exemplified. Of the pyrrole derivatives, those having a hydrocarbon group in the pyrrole ring are especially preferred.

The other amide used in the present invention is an acid amide. As the acid amide, compounds represented by the following general formulas (1) to (3) are usable. The general formulas (1) to (3) simultaneously include an imide, which is another nitrogen compound used in the present invention, for convenience' sake.

Examples of the acid amide or imide compounds used in the present invention are represented by the following general formulas (1) to (3).

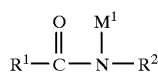

(1)

wherein $M^1$ represents a hydrogen atom or a metal element in the Groups IA, IIA, IB and IIIA of the Periodic Table, $R^1$ represents a hydrogen atom, an alkyl group having 1 to 30 carbon atoms, alkenyl group having 1 to 30 carbon atoms, an aralkyl group having 1 to 30 carbon atoms, an aryl group which may have a substituent or an aryl group which may contain a hetero element, and $R^2$ represents a hydrogen atom, an alkyl group having 1 to 30 carbon atoms, alkenyl group having 1 to 30 carbon atoms, an aralkyl group having 1 to 30 carbon atoms, an aryl group which may have a substituent, an aryl group which may have a hetero element or an acyl group: $-C(=O)R^3$, ($R^3$ is defined in the same as $R^1$, $R^3$ and $R^1$ may be either the same or different), and $R^1$ and $R^2$ may form a ring.

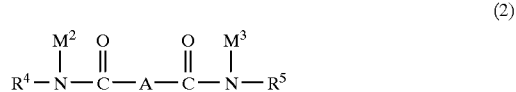

(2)

wherein $M^2$ and $M^3$ independently represent a hydrogen atom, or a metal element in the Groups IA, IIA, IB and IIIA of the Periodic Table, $R^4$ and $R^5$ independently represent a hydrogen atom, an alkyl group having 1 to 30 carbon atoms, alkenyl group having 1 to 30 carbon atoms, an aralkyl group having 1 to 30 carbon atoms, an aryl group which may contain a substituent, or an aryl group which may have a hetero element, $R^4$ and $R^5$ may form a ring, and A represents an alkylene group which may contain an unsaturated bond.

As examples of an acid amide represented by the general formula (1) or (2) will be cited acetamide, N-methylhexane amide, succinamide, maleamide, N-methylbenzamide, imidazole-2-carbonamide, di-2-thenoyl amine, β-lactam, δ-lactam, ε-caprolactam, and the salts of one of these compounds and a metal element in the Groups IA, IIA, IB and IIIA of the Periodic Table.

Examples of an imide are 1,2-cyclohexane dicarboxyimide, succcinimide, phthalimide, maleimide, 2,4,6-pyperidine trione, perhydroazecyne-2,10-dione, and the salts of one of these compounds and a metal element in the Groups IA, IIA, IB and IIIA of the Periodic Table.

(3)

wherein $M^4$ represents a hydrogen atom or a metal element in the Groups IA, IIA, IB and IIIA of the Periodic Table, $R^6$ represents a hydrogen atom, an alkyl group having 1 to 30 carbon atoms, alkenyl group having 1 to 30 carbon atoms, an aralkyl group having 1 to 30 carbon atoms, an aryl group which may contain a substituent, $R^6$ and $R^8$ being either the same or different, $R^7$ represents a hydrogen atom, an alkyl group having 1 to 30 carbon atoms, alkenyl group having 1 to 30 carbon atoms, an aralkyl group having 1 to 30 carbon atoms, an aryl group which may have a substituent, an aryl group which may have a hetero element or an $SO_2R^8$ group, ($R^8$ is defined in the same as $R^6$ and $R^8$ and $R^6$ may be either the same or different), and $R^6$ and $R^7$ may form a ring.

As examples of the sulfonamides and sulfonimides represented by the general formula (3) will be cited benzene sulfonamide, N-methylmethane sulfonamide, N-methyltrifluoromethyl sulfonamide, and the salts of one of these compounds and a metal element in the Groups IA, IIA, IB and IIIA of the Periodic Table.

Among the above-described acid amides or imide compounds, the compounds represented by the general formula (1) are preferable, and especially preferable are the imide compounds in which $R^2$ in the general formula (1) represents an acyl group: $C(=O)R^3$, and $R^1$ and $R^3$ form a ring.

The alkylaluminum compounds used in the present invention are those represented by the)following formula (4):

$$R^1_m Al(OR^2)_n H_p X_q \quad (4)$$

wherein $R^1$ and $R^2$ are each a hydrocarbon group having usually 1 to 15 carbon atoms, preferably 1 to 8 carbon atoms, and $R^1$ and $R^2$ may be the same or different from each other; X is a halogen atom; m, n, p and q are the numbers defined by $0<m\leq3$, $0\leq n<3$, $0\leq p<3$ and $0\leq q<3$, respectively, and $m+n+p+q=3$.

The above-defined alkylaluminum compounds include the trialkylaluminum compounds represented by the following formula (5), the halogenated alkylaluminum compounds represented by the following formula (6), the alkoxyaluminum compounds represented by the following formula (7) and the alkylaluminum hydride compounds represented by the following formula (8):

$$R^1_3 Al \quad (5)$$

$$R^1_m AlX_{3-m} \;(1.5 \leq m < 3) \quad (6)$$

$$R^1_m Al(OR^2)_{3-m} \quad (7)$$
$(0 < m < 3,\ \text{preferably}\ 1.5 \leq m < 3)$ $$R^1_m AlH_{3-m} \quad (8)$$
$(0 < m < 3,\ \text{preferably}\ 1.5 \leq m < 3)$ As specific examples of the said alkylaluminum compounds, trimethylaluminum, triethylaluminum, triisobutylaluminum, diethylaluminum monochloride, diethylaluminum ethoxide and diethylaluminum hydride may be exemplified. Also, as the alkylaluminum compounds used in the present invention, a mixture of 2 or more compounds above, for example, trialkylaluminum and halogenated alkylaluminum can be used. Of these compounds, trialkylaluminum is especially preferred because of minimized formation of polymeric by-products.

The halogen-containing compound (d) used in the present invention may be any compound containing a halogen atom, but the following halogen-containing compounds (1) to (4) are preferable.

A halogen-containing compound (1) is a compound containing an element in the Groups IIIA, IIIB, IVA, IVB, VA, VB and VIB of the Periodic Table. Concrete examples thereof are scandium chloride, yttrium chloride, lanthanum chloride, titanium tetrachloride, zirconium tetrachloride, hafnium tetrachloride, boron trichloride, aluminum chloride, diethylaluminum chloride, ethylaluminum sesquichloride, gallium chloride, carbon tetrachloride, chloroform, methylene chloride, dichrloroethane, hexachlorobenzene, 1,3,5-trichlorobenzene, trityl chloride, silane tetrachloride, trimethylchlorosilane, germanium tetrachloride, tin tetrachloride, tributyltin chloride, phosphorus trichloride, antimony trichloride, trityl hexachlroroantimonate, antimony pentachloride, bismuth trichloride, boron tribromide, aluminum tribromide, carbon tetrabromide, bromoform, bromobenzene, iodomethane, silicon tetrabromide, hexafluorobenzene and aluminum fluoride. As a halogen in the halogen-containing compound (1), bromine or chlorine is preferable. Among these, compounds having a large number of halogen atoms are preferable, and compounds soluble in a solvent which is used in an oligomerization reaction are also preferable and especially chlorine is more preferred from the synthetic viewpoint of a catalytic activity, a selectivity of the objective product, etc. Particularly preferable halogen-containing compounds (1) are carbon tetrachloride, chloroform, dichloroethane, titanium tetrachloride, germanium tetrachloride and tin tetrachloride. It is possible to use a mixture of at least two of these compounds.

A halogen-containing compound (2) is a linear hydrocarbon which is sustituted with at least three halogen atoms and which has at least two carbons. As the linear hydrocarbon as the halogen-containing compound (2), a linear saturated hydrocarbon is preferable, and a linear saturated hydrocarbon in which adjacent two carbons are replaced by at least three halogen atoms is more preferable. A linear saturated hydrocarbon which is represented by the general formula (9), (10) or (11) is especially preferable.

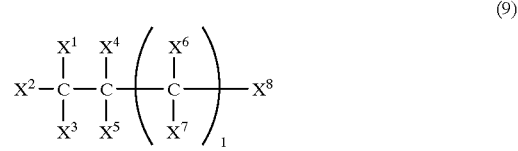
(9)

wherein $X^1$ to $X^8$ represent hydrogen atoms or halogen atoms, and at least three of $X^1$ to $X^5$ are halogen atoms, and 1 represents 0 or an integer of 1 to 8.

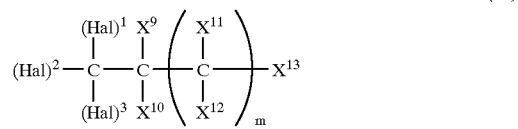
(10)

wherein $(Hal)^1$ to $(Hal)^3$ represent halogen atoms, $X^9$ to $X^{13}$ represent halogen atoms or hydrogen atoms, and m represents 0 or an integer of 1 to 8.

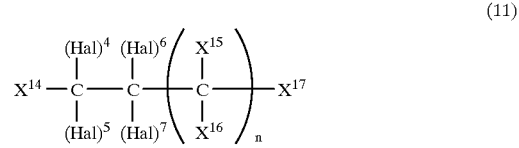
(11)

wherein $(Hal)_4$ to $(Hal)_7$ represent halogen atoms, $X^{14}$ to $X^{17}$ represent halogen atoms or hydrogen atoms, and n represents 0 or an integer of 1 to 8.

As a halogen in the halogen-containing compound (2), chlorine or bromine is preferable and especially chlorine is more preferred from the synthetic viewpoint of a catalytic activity, a selectivity of the objective product, etc., and 1, m and n are preferable 0,1,2 and 3, respectively. As the linear hydrocarbon halide represented by the general formula (9), (10) and (11) are preferable 1,1,1-trichloroethane, 1,1,2-trichloroethane, 1,1,2,2-tetrachloroethane, pentachloroethane, hexachlroroethane, 1,1,1-trichloropropane, 1,1,2,2-tetrachloropropane, 1,1,1-trichlorobutane, 1,1,2,2-tetrachlorobutane, 1,1,1-trichloropentane, 1,1,2,2-tetrachloropentane, 1,1,1-tribromoethane, 1,1,2,2-tetrabromoethane, etc. Among them, 1,1,-trichloroethane, pentachloroethane, hexachloroehtane and 1,1,2,2-tetrachloroethane are more preferred.

Use of the halogen-containing compound (2) is advantageous not only in that the catalytic activity and the selectivity of a trimer are greatly enhanced but also in that the deterioration of the catalyst with passage of time is ameliorated.

A halogen-containing compound (3) is a cyclic hydrocarbon halide. As the halogen-containing compound (3), a cyclic saturated hydrocarbon is preferable and a cyclic saturated hydrocarbon which is substituted with three halogen atoms is more preferable. As the halogen atom, chlorine or bromine is preferable and especially chlorine is more preferred from the synthetic viewpoint of a catalytic activity, a selectivity of the objective product, etc.

Concrete examples of the halogen-containing compound (3) are cyclopropane trihalides such as 1,2,3-trichlorocyclopropane, 1,1,2-trichlorocyclopropane, 1,2,3-tribromocyclopropane and 1,1,2-tribromocylcopropane; cyclopropane tetrahalides such as 1,1,2,3-tetrachlorocyclopropane, 1,1,2,2-tetrachlorocyclopropane, 1,1,2,3-tetrabromocyclopropane and 1,1,2,2-tetrabromocyclopropane; cyclopropane pentahalides such as pentachlorocyclopropane and pentabromocyclopropane; cyclopropane hexaharide such as hexachlorocyclopropane and hexabromocyclopropane; cyclobutane trihalides such as 1,2,3-trichlorocyclobutane, 1,1,2-trichlorocyclobutane, 1,2,3-tribromocyclobutane and 1,1,2-tribromocylcobutane; cyclobutane tetrahalides such as 1,2,3,4-tetrachlorocyclobutane, 1,1,2,3-tetrachlorocyclobutane, 1,2,3,4-tetrabromocyclobutane and 1,1,2,3-tetrabromocylcobutane; cyclobutanepentahalides such as 1,1,2,3,4-pentachlorocyclobutane, 1,1,2,2,3-pentachlorocyclobutane, 1,1,2,3,4-pentabromocyclobutane and 1,1,2,2,3-pentabromocylcobutane; cyclobutanehexahalides such as 1,1,2,2,3,4-hexachlorocyclobutane, 1,1,2,2,3,3-hexachlorocyclobutane, 1,1,2,2,3,4-hexabromocyclobutane and 1,1,2,2,3,3-hexabromocylcobutane; cyclobutane heptahalides such as heptachlorocyclobutane and heptabromocyclobutane; and cyclobutane octahalides such as octachlorocyclobutane and octabromocyclobutane.

Further examples are cyclopentane trihalides such as 1,2,3-trichlorocyclopentane, 1,1,2-trichlorocyclopentane, 1,2,3-tribromocyclopentane and 1,1,2-tribromocylcopentane; cyclopentane tetrahalides such as 1,2,3,4-tetrachlorocyclopentane, 1,1,2,3-tetrachlorocyclopentane, 1,2,3,4-tetrabromocyclopentane and 1,1,2,3-tetrabromocyclopentane; cyclopentane pentahalides such as 1,2,3,4,5-pentachlorocyclopentane, 1,1,2,3,4-pentachlorocyclopentane, 1,1,2,2,3-pentachlorocyclopentane, 1,2,3,4,5-pentabromocyclopentane, 1,1,2,3,4-pentabromocyclopentane and 1,1,2,2,3-pentabromocyclopentane; cyclopentane hexahalides such as 1,1,2,3,4,5-hexachlorocyclopentane, 1,1,2,3,4,5-hexabromocyclopentane and 1,1,2,2,3,4-hexabromocyclopentane; cyclopentane heptahalides such as 1,1,2,2,3,4,5-heptachlorocyclopentane and 1,1,2,2,3,4,5-heptabromocyclopentane; cyclopentane octahalides such as 1,1,2,2,3,3,4,5-octachlorocyclopentane and 1,1,2,2,3,3,4,5-octabromocyclopentane; cyclopentane nonahalides such as nonachlorocyclopentane; and cyclopentane decahalides such as decachlorocyclopentane.

Still further examples are cyclohexane trihalides such as 1,2,3-trichlorocyclohexane, 1,1,2-trichlorocyclohexane, 1,2,3-tribromocyclohexane and 1,1,2-tribromocylcohexane; cyclohexane tetrahalides such as 1,2,3,4-tetrachlorocyclohexane, 1,1,2,3-tetrachlorocyclohexane, 1,2,3,4-tetrabromocyclohexane and 1,1,2,3-tetrabromocyclohexane; cyclohexane pentahalides such as 1,2,3,4,5-pentachlorocyclohexane, 1,1,2,3,4-pentachlorocyclohexane, 1,1,2,2,3-pentachlorocyclohexane, 1,2,3,4,5-pentabromocyclohexane, 1,1,2,3,4-pentabromocyclohexane and 1,1,2,2,3-pentabromocyclohexane; cyclohexane hexahalides such as 1,2,3,4,5,6-hexachlorocyclohexane and 1,2,3,4,5,6-hexabromocyclohexane; cyclohexane heptahalides such as 1,1,2,3,4,5,6-heptachlorocyclohexane and 1,1,2,3,4,5,6-heptabromocyclohexane; cyclohexane octahalides such as 1,1,2,2,3,4,5,6-octachlorocyclohexane and 1,1,2,2,3,4,5,6-octabromocyclohexane; cyclohexane nonahalides such as 1,1,2,2,3,3,4,5,6-nonachlorocyclohexane; cyclohexane decahalides such as 1,1,2,2,3,3,4,4,5,6-decachlorocyclohexane; cyclohexane undecahalides such as undecachlorocyclohexane; and cyclohexane dodecahalides such as dodecachlorocyclohexane.

Among these, 1,2,3-trichlorocyclopropane, pentachlorocyclopropane, 1,2,3,4-tetrachlorocyclobutane, 1,2,3,4,5-pentachlorocyclopentane and 1,2,3,4,5,6-hexachlorocyclohexane are especially preferable.

Use of the halogen-containing compound (3) is advantageous not only in that the catalytic activity and the selectivity of a trimer are greatly enhanced but also in that the deterioration of the catalyst with passage of time is ameliorated.

A halogen-containing compound (4) is a halogenated allyl compound which is substituted with one or two halogen atom at allyl position (at carbon atom adjacent to a double bond) and represents by the following formula (12):

(12)

wherein $X^{18}$ to $X^{20}$ represent hydrogen atom or alkyl group having 1 to 30 carbon atoms, $X^{21}$ to $X^{23}$ represent hydrogen atom, alkyl group having 1 to 30 carbon atoms or halogen atom and one or two of $X^{21}$ to $X^{23}$ is halogen atom.

As a halogen atom in the halogen-containing compound (4), chlorine or bromine is preferable and especially, chlorine is more preferred from the synthetic viewpoint of a catalytic activity, a selectivity of the objective product, etc.

Concrete example of the halogen-containing compound (4) are allyl chloride, 3,3-dichloro-1-propene, 3-chloro-1-butene, 3,3-dichloro-1-butene, 1-chloro-2-butene, 1,1-dichloro-2-butene, 3-chloro-3-methyl-1-butene, 3-chloro-1-pentene, 3,3-dichloro-1-pentene, 4-chloro-2-pentene, 4,4-dichloro-2-pentene, 1-chloro-2-pentene and 1,1-dichloro-2-pentene. Among them, allyl chloride is preferable.

Use of the halogen-containing compound (4) is advantageous not only in that the catalytic activity and the selectivity of a trimer are greatly enhanced but also in that since the activity based on the halogen atom is high, the amount of the halogen-containing compound used is small, or since the amount of halogen-containing substances decomposed during reaction steps or in the distillation step is small, it is possible to separate easily halogen-containing impurities at the distillation of the trimer and to recover the objective product at the high purity.

In the present invention, t-butyldimethylsilyl trifluorate (t-BuMe$_2$SiOSO$_2$CF$_3$), trispentafluorophenylboron (B(C$_6$F$_5$)$_3$), trifluoromethanesulfonic acid (CF$_3$SO$_3$H), hexafluoroisopropanol ((CF$_3$)$_2$CHOH), etc. are also preferably usable.

In the present invention, when the nitrogen-containing compound (b) is one selected from the group consisting of maleimides and derivatives thereof, it is preferred to use an inorganic halides as the halogen-containing compound (d).

In the present invention, an α-olefin oligomerization reaction is conducted in a solution by using a chromium-based catalyst system composed of a combination of the catalyst components (a) to (d) is used. When a chromium compound containing a halogen such as chromous chloride is used as the chromium compound (a), such chromium compound also serves as the halogen-containing compound (d). Similarly, an alkylaluminum compound containing a halogen such as diethylaluminum monochloride is used as the alkylaluminum compound (c), such alkylaluminum compound also serves as the halogen-containing compound (d).

As the α-olefin used as starting material in the present invention, substituted or non-substituted α-olefins having 2 to 30 carbon atoms are usable. As such α-olefins, ethylene, propylene, 1-butene, 1-hexene, 1-octene, 3-methyl-1-butene and 4-methyl-1-pentene may be exemplified. Ethylene is especially preferred since it is possible to produce 1-hexene as a trimer at a high selectivity and in a high yield.

As the solvent used in the reaction of the present invention, there can be used acyclic or alicyclic saturated hydrocarbons having 3 to 20 carbon atoms such as butane, pentane, 3-methylpentane, hexane, heptane, 2-methylhexane, octane, cyclohexane, methylcyclohexane, decalin, etc.; aromatic hydrocarbons such as benzene, toluene, xylene, ethylbenzene, mesitylene, tetralin, etc. These reaction solvents may be used either singly or as a mixture.

The α-olefin used as the starting material for the reaction or the α-olefins other than the main starting material for the reaction can also be used as a reaction solvent. The α-olefin can be incorporated into chromium-based catalyst system as a catalyst component before the initiation of the oligomerization. An α-olefin having 4 to 30 carbon atoms, especially an α-olefin which is liquid at room temperature is preferred as a reaction solvent.

As a reaction solvent, a chain saturated hydrocarbon having 4 to 7 carbon atoms or alicyclic saturated hydrocarbons having 4 to 7 carbon atoms is preferably used. Use of a solvent such as mentioned above proves helpful for suppressing formation of the polymeric by-products. Further, in case of using an alicyclic hydrocarbon, a high catalytic activity can be obtained. As typical examples of such saturated hydrocarbons, butane, pentane, hexane, heptane or cyclohexane may be exemplified. These solvents may have a branched chain structure.

Reaction temperature is usually 0 to 250° C., preferably 10 to 150° C., more preferably 20 to 100° C. Reaction pressure can be suitably selected from between 3 kg/cm$^2$ and 250 kg/cm$^2$, but a pressure between about 5 kg/cm$^2$ and 100 kg/cm$^2$ is preferable. Reaction time is usually one minute to 20 hours, preferably 0.5 to 6 hours. The type of reaction may be batchwise, semi-batchwise or continuous.

In the present invention, it is preferable that 0.1 to 15 vol % of hydrogen exists in the gas phase of a reaction vessel. Use of such a specific amount of hydrogen prevents the production of a filmy polymer as a by-product.

In a first aspect of the present invention, an α-olefin is oligomerized by supplying each of the components (a) to (d) to the reaction system in such a manner that the chromium compound (a) and the alkylaluminum compound (c) do not come into contact with each other before each of the components (a) to (d) and the α-olefin co-exists in a reaction solvent and the oligomerization of α-olefin takes place. By adopting this contacting method, the catalytic activity is greatly improved, the selectivity of a trimer is greatly enhanced and the content of 1-alkene among the said trimer obtained also becomes very high.

In the contacting mode of the present invention, for improving the catalytic activity and the selectivity of the objective product, it is preferable to adjust the concentration of α-olefin in the reaction system to high when α-olefin is contacted with the chromium-based catalyst system. Concretely, the α-olefin concentration in the reaction solvent of the reaction system of 5 to 100 mol %, more preferably 10 to 100 mol %, still more preferably 20 to 100 mol % is exemplified.

In the case where α-olefin of a low boiling point, for example, ethylene and the like is introduced as a gas in the reaction system, it is preferable to contact α-olefin with the chromium-based catalyst system under the α-olefin pressure of about 3 to 250 kg/cm$^2$, more preferably about 5 to 100 kg/cm$^2$, still more preferably about 5 to 50 kg/cm$^2$, so that the oligomerization of the α-olefin can carried out without needing a catalyst formation step.

In the present contact mode of the present invention, the presence of high concentration of α-olefin can improve the catalytic activity of the α-olefin oligomerization. The reason is not clear at present, but it is presumed as follows.

That is, when the chromium compound is contacted with the alkylaluminum compound, the alkylation of the chromium compound followed by reduction of it, via reductive elimination, may proceed to give the low valent, coordinatively unsaturated chromium complex(es). Such low valent, coordinatively unsaturated chromium complex(es) themselves easily decompose because of their instability. On the other hand, α-olefin can coordinate to the metal center in the low valent, coordinatively unsaturated chromium complex (es) in the presence of α-olefin to give the optimum chromium-olefin complexes for the oligomerization of the α-olefin in the present invention when the chromium compound is contacted with the alkylaluminum compound. The high concentration of coexisting α-olefin makes it advantageous to form such chromium-olefin complexes. Therefore, when the chromium compound and the alkylaluminum compound contacts each other, if the high concentration of α-olefin coexists therewith, the olefin complexes are produced quite effectively.

Furthermore, the advantage using the high concentration of α-olefins is as follows. Since there is dissociation equilibrium between the coordinated olefin in the olefin complexes and free α-olefin in the solution, the concentration of the olefin complexes is increased and the olefin complexes are stabilized in the presence of the high concentration of the α-olefin. Therefore, since the olefin complexes would be more stable under the higher concentration of the α-olefin because of the reason described above, it is more preferable to initiate the oligomerization of the α-olefin at the same time when the chromium compound is contacted with the alkylaluminum compound without the catalyst preparation steps (described in ZA 93/0350) in order to obtain the objective product with high activity and selectivity. Further, since the stability of the chromium-olefin complexes toward heat and moisture depends on the π-acceptor ability of the coordinated olefin, ethylene is the most profitable α-olefin because of its potent π-acceptor property among all of α-olefins and of its strong coordination bond to chromium metal center. From these respects, ethylene is the most suitable α-olefin for the oligomerization in the present invention.

As examples of the specific contacting mode, the following methods (1) to (9) will be cited. Each of the following solutions is ordinarily formed by using a reaction solvent.

(1) Method of introducing the chromium compound (a) and the α-olefin into a solution containing the nitrogen-containing compound (b), the alkylaluminum compound (c) and the halogen-containing compound (d).

(2) Method of introducing the alkylaluminum compound (c) and the α-olefin into a solution containing the chromium compound (a), the halogen-containing compound (d) and the nitrogen-containing compound (b).

(3) Method of introducing the nitrogen-containing compound (b), the alkylaluminum compound (c) and the α-olefin into a solution containing the chromium compound (a) and the halogen-containing compound (d).

(4) Method of introducing the chromium compound (a), the nitrogen-containing compound (b) and the α-olefin into a solution containing the alkylaluminum compound (c) and the halogen-containing compound (d).

(5) Method of introducing the alkylaluminum compound (c), the halogen-containing compound (d) and the α-olefin into a solution containing the chromium compound (a) and the nitrogen-containing compound (b).

(6) Method of introducing the chromium compound (a), the halogen-containing compound (d) and the α-olefin into a solution containing the nitrogen-containing compound (b) and the alkylaluminum compound (c).

(7) Method of introducing the chromium compound (a), the nitrogen-containing compound (b), the halogen-containing compound (d) and the α-olefin into a solution containing the alkylaluminum compound (c).

(8) Method of introducing the halogen-containing compound (d), the nitrogen-containing compound (b), the alkylaluminum compound (c) and the α-olefin into a solution containing the chromium compound (a).

(9) Method of introducing the chromium compound (a), the nitrogen-containing compound (b), the alkylaluminum compound (c), the halogen-containing compound (d) and the α-olefin into a reaction system simultaneously and independently of each other.

A method of maintaining the chromium compound and the alkylaluminum compound in such a manner as not to come into contact with each other before the initiation of an oligomerization reaction, and simultaneously and separately supplying the chromium compound and the alkylaluminum compound with the α-olefin into the reaction system at the time of an oligomerization reaction can be carried out.

In the present invention, the expression of "in the mode that the chromium compound and the alkylaluminum compound do not come into contact with each other before the initiation of an oligomerization reaction" means that the chromium compound and the alkylaluminum compound are maintained in this mode not only before the initiation of an oligomerization reaction but also when additional α-olefin and catalyst components are supplied to the reaction vessel. The said specific contacting mode, however, is of a preferable mode required at the time of the formation of the catalyst from the catalyst components, and after the formation of the catalyst, this mode is unnecessary. Therefore, after the formation of the catalyst by the said mode, it is possible to recycle the catalyst solution recovered from the reaction system to the reaction vessel and it does not contradict with the contacting mode of the present invention.

Among of the above-mentioned contacting mode of the present invention, the catalytic activity is remarkably improved by continuously supplying α-olefin to the reaction system and continually supplying each of catalyst components the chromium compound (a), the nitrogen-containing compound (b), the alkylaluminum compound (c) and the halogen-containing compound (d) to the reaction system as compared with a batch reaction and the semi-batch reaction. In case of supplying continuously the each catalyst component to the reaction system, it is preferable to conduct α-olefin oligomerization reaction using a stirred-tank reactor.

In a second aspect of the present invention, the catalyst components which contain at least the alkylaluminum compound (c) and the halogen-containing compound (d) and which does not contain the chromium compound (a) are heated to not lower than 100° C. in a reaction solvent in advance, and the treated catalyst components are contacted with the rest of the catalyst components and an α-olefin in the reaction solvent. If after the specific catalyst components are heated they are contacted with the remaining catalyst components and α-olefin, the reaction selectivity is improved.

The preheating temperature for the catalyst components is preferably not lower than 100° C., but if the temperature is too high, there may be a fear of the alkylaluminum compound (c) being metallized. In consideration of the progress of side reaction and economical efficiency, the preheating temperature is ordinarily set to be not higher than 200° C. The preferable preheating temperature is 110 to 180° C., and the more preferable temperature is 120 to 160° C. The preheating time depends on the preheating temperature, but it is ordinarily 5 to 120 minutes, preferably 30 to 90 minutes. Although it is not definitely clear why the selectivity of the catalytic reaction is enhanced, it is presumed that the chromium-based catalyst system is formed effectively and the α-olefin oligomerization is accelerated by the preheating.

The above-described preheating method is preferably combined with the method of "a mode that the chromium compound and the alkylaluminum compound do not come into contact with each other before the initiation of a reaction". For example, in the case of the introducing method (1), an α-olefin and the chromium compound (a) are introduced into a solution containing the nitrogen-containing compound (b), the alkylaluminum compound (c) and the halogen-containing compound (d), which is preheated to a temperature of not lower than 100° C. For another example, in the case of the introducing method (4), an α-olefin, the chromium compound (a) and the nitrogen-containing compound (b) are introduced into a solution containing the alkylaluminum compound (c) and the halogen-containing compound (d), which is preheated to a temperature of not lower than 100° C. This method produces an excellent result in the reaction selectivity, the catalytic activity, etc. in comparison with the method in which after a solution containing the chromium compound (a), the alkylaluminum compound (c) and the halogen-containing compound (d) is preheated to a temperature of not lower than 100° C., and thereafter an α-olefin is introduced into the resultant solution.

In the preheating method, a halogen-containing compound which contains an element in the Groups IIIA, IIIB, IVA, IVB, VA and VB in the Periodic Table is preferably used as the halogen-containing compound (d).

In the above-mentioned specific contacting mode and preheating mode, the existing amount of the chromium compound (a) in the reaction system is ordinarily $1 \times 10^{-7}$ to 0.5 mol, preferably $5 \times 10^{-7}$ to 0.2 mol, more preferably $1 \times 10^{-6}$ to $5 \times 10^{-2}$ mol based on one liter of the reaction solvent. The existing amount of the nitrogen-containing compound (b) in the reaction system is ordinarily $1 \times 10^{-7}$ to 0.1 mol, preferably $5 \times 10^{-7}$ to $5 \times 10^{-2}$ mol, more preferably $1 \times 10^{-6}$ to $1 \times 10^{-2}$ mol based on one liter of the reaction solvent. The existing amount of the alkylaluminum compound (c) in the reaction system is ordinarily $1 \times 10-7$ to $7 \times 10^2$ mol, preferably $5 \times 10^{-7}$ to $5 \times 10^{-2}$ mol, more preferably $1 \times 10^{-6}$ to $1 \times 10^{-2}$ mol based on one liter of the reaction solvent. The existing amount the halogen-containing compound (d) in the reaction system is ordinarily $1 \times 10^{-7}$ to 0.1 mol, preferably $5 \times 10^{-7}$ to $5 \times 10^{-2}$ mol, more preferably $1 \times 10^{-6}$ to $1 \times 10^{-2}$ mol based on one liter of the reaction solvent. It is preferred to use a catalytically effective amount of each of the catalyst components.

In the present invention, the molar ratio of (a) the chromium compound, (b) the amine or metal amide, and (c) the alkylaluminum compound in the reaction system is adjusted ordinarily so as to (a):(b):(c):(d)=1:0.1 to 100:0.1 to 500:0.1 to 100, preferably (a):(b): (c):(d)=1:0.1 to 10:1 to 100:0.1 to 20, more preferably (a):(b):(c):(d)=1:1 to 5:5 to 150:1 to 10. By combining such specific conditions, it is possible to produce α-olefin oligomers, for example hexenes, in a yield of not less than 90% by weight (ratio to the total amount of products), and further, the selectivity of 1-hexene in the produced hexenes can be enhanced to 99% or more.

In a third aspect of the present invention, the oligomerization of an α-olefin in a reaction solvent is conducted by a semi-batch process or by a continuous process, and at least one catalyst component selected from the group consisting of the nitrogen-containing compound (b), the alkylaluminum compound (c) and the halogen-containing compound (d) is added as supplement to the reaction system. According to this process, the activation of the catalyst in the reaction system is realized, so that it is possible to produce a α-olefin oligomer comprising 1-hexene as the main ingredient especially from ethylene with a high yield and high selectivity.

In the catalyst system composed of the above-described catalyst components, since the catalyst begins to deactivate about 30 to 60 minutes after the initiation of a reaction (when the residence time of the α-olefin as the raw material exceeds 30 to 60 minutes), it is very important to enhance the catalytic efficiency. It is preferable to improve the catalytic efficiency by activating the catalyst in the reaction system in order to use the catalyst only once and then throw it away. According to the above-described process, this demand is satisfied.

The reaction in a semi-batch process is achieved by continuously supplying an α-olefin to the reaction vessel, and the reaction in a continuous process is achieved by using a tubular reactor or a multi-staged stirred tank. The tubular reactor is fundamentally a reaction apparatus for introducing a reaction component from one end of a straight tube or a coiled or a U-shaped tube and discharging the reaction product from the other end thereof. The multi-staged stirred tank is fundamentally a reaction apparatus composed of a plurality of stirred tanks which are arranged in series. A reaction component is introduced to a first stirred tank, then it is moved to subsequent tanks and the reaction product is discharged from the final stirred tank.

This mode of adding a specific catalyst component is preferably combined with the method of "a mode that the chromium compound and the alkylaluminum compound do not come into contact with each other before the initiation of a reaction". In the case of a semi-batch process for the reaction, after the catalyst components are contacted in the above-described specific mode, the reaction is initiated in the reaction vessel, an α-olefin is continuously supplied to the reaction vessel in such a manner that the reaction pressure is maintained at a constant pressure, and the above-described specific catalyst component is added to the reaction vessel. In the case of a continuous reaction process using a tubular reactor, the catalyst components other than the chromium compound are introduced from the end of the tubular reactor, and the α-olefin and the chromium compound are introduced from a middle of the tubular reactor. After all of the catalyst components and α-olefin are contacted and a oligomerization is initiated, the specific catalyst component is introduced from an appropriate position of the tubular reactor. In the case of a continuous reaction process using a multi-staged stirred tank, the chromium-based catalyst and α-olefin are introduced to the first stirred tank, and the specific catalyst component is added to a stirred tank after the first stirred tank.

The timing at which the specific catalyst component is added is not limited, but ordinarily it is after the time at which the catalytic activity begins to lower. It is possible to add the specific catalyst component after the deactivation of the catalyst, but to provide a long deactivation period is industrially disadvantageous. It is, therefore, preferable to add the specific catalyst component in the period between the time at which the catalytic activity begins to lower and the time at which the catalyst deactivates. This period varies according to the types of the catalyst components, but it is about 15 to 90 minutes after the initiation of the oligomerization reaction (when the residence time of the α-olefin as the raw material exceeds 15 to 90 minutes).

As the nitrogen-containing compound (b), the alkylaluminum compound (c) and the halogen-containing compound (d) which are supplemented in the reaction system as the specific reaction compound, the same compounds as the catalyst components which are used for the initiation of the oligomerization, but it is not always necessary that they are the same. The specific catalyst component may be added to the reaction system any number of times until the catalyst completely deactivates. For example, in the case of a semi-batch process, it is possible to add the specific catalyst component every time a predetermined reaction time elapses. In the case of a continuous reaction using a tubular reactor or a multi-staged mixed tank, it is possible to add the specific catalyst component from appropriate positions at which the residence time is different.

In case of adding the said catalyst components, the amount of the chromium compound used in the initiation of the oligomerization is $1 \times 10^{-7}$ to 0.5 mol, preferably $5 \times 10^{-7}$ to 0.2 mol, more preferably $1 \times 10^{-6}$ to $5 \times 10^{-2}$ mol based on one liter of the reaction solvent.

The amount of each component added as supplement each time is not defined as the deactivation speed of the catalyst system can not uniformly defined because it is changed due to the reaction conditions, but an amount of nitrogen-containing compound (b), an amount of alkylaluminum compound (c) and an amount of halogen-containing compound (d), which are added as supplement, are respectively preferably not more than 10 mol, more preferably 0.1 to 10 mol, still more preferably 1 to 5 mol, preferably not more than 100 mol, more preferably 1 to 100 mol, still more preferably 5 to 50 mol, preferably not more than 20 mol, more preferably 0.1 to 20 mol, still more preferably 1 to 10 mol, per one mol of the chromium compound (a) added at the initiation of the oligomerization.

According to this method of supplementing a specific catalyst component, it is possible to activate the chromium-based catalyst whose catalytic activity (g-α-olefin/g-chromium.Hr) in the reaction system gradually lowers and continuously to use the chromium-based catalyst. It is, therefore, possible to greatly enhance the efficiency of the chromium-based catalyst by using it until it completely deactivates, for example, due to the thermal history.

In the method of adding a specific catalyst component, a halogen-containing compound which contains an element in the Groups IIIA, IIIB, IVA, IVB, VA and VB in the Periodic Table is preferably used as the halogen-containing compound (d).

The α-olefin oligomerization can also be carried out in the presence of water of 0.001 to 1.5 mol based on one mole of alkylaluminum compound (c) in the reaction system. For example, n-heptane used as the reaction solvent may contain about 100 ppm of water. If such n-heptane is used as the reaction solvent, though depending to the molar ratio of the catalyst components, the molar ratio of water accompanied from the reaction solvent to the alkylaluminum compound (c) is more than 1.5 mol, so that a large amount of polymers such as polyethylene, etc. is by-produced and the selectivity of the objective products is remarkably lowered. However, it is relatively easy to decrease the water content of n-heptane to 5 to 20 ppm. For example, in case of removing water by a distilling column, the distilling column having a relatively small number of stages can be used. The treating method comprising using desiccating agent which is a little utility as compared with the distilling column. Therefore, by existing water of 0.001 to 1.5 mol based on the alkylaluminum compound (c) in the reaction system, it is possible to pare down refining cost which is unnecessary and it is remarkably profitable in industrial.

Further, it is preferable that the catalyst components, the reaction solvent and α-olefin are previously treated with the desiccating agent, such as molecular sieves, to adjust the water content existing in the reaction system. As the desiccating agent, molecular sieve are usable. Also, in order to dry the reaction solvent, the alkylaluminum compound which is one of the catalyst components can be used for the desiccating agent. In this case, since aluminoxane is by-produced by the reaction of the alkylaluminum compound and water, before using as the catalyst component the alkylaluminum compound, it is preferred that the produced aluminoxane is removed by filtration, etc.

In the present invention, it is possible to add at least one selected from the group consisting of an alkylating agent, a reducing agent and a halogen-containing compound to the solvent containing the catalyst components which is recovered by separating the α-olefin oligomer from the reaction solution by distillation, and to circulate the mixed solvent to the reaction system. That is, it is possible to activate the catalyst by a simple operation of adding the above-described specific compound to the solvent containing the catalyst components. It goes without saying that there is no bad influence in circulating the activated catalyst to the reaction system together with the added component.

In this method, a halogen-containing compound which contains an element in the Groups IIIA, IIIB, IVA, IVB, VA and VB in the Periodic Table is preferably used as the halogen-containing compound (d).

In this method of the present invention, distillation for separating α-olefin oligomers may not necessarily be conducted on all of the substances in the reaction mixture. For instance, in case of producing 1-hexene from ethylene, small amount of other α-olefin oligomers such as 1-octene may be left in the reaction mixture without separation. Also, the by-products such as $C_{10}$ compounds may be left in the reaction mixture.

As examples of an alkylating agent added to the solvent containing the catalyst components alkylaluminum compounds such as triethylaluminum, which is described above as one of the catalyst components are usable. Other examples of the alkylating agent are a Grignard reagent (RMgX), alkyl lithium (RLi), and alkyl boron ($BR_3$). The alkylaluminum compound also serves as a reducing agent. Therefore, as the reducing agent which is added to the solvent containing the catalyst components, an alkylaluminum compound as an alkylating agent is used, but the reducing agent is not restricted thereto and ordinary reducing agents are usable. The ordinary reducing agents are, for example, $NaBH_4$, $LiAlH_4$, LiH, NaH, KH, Na, K, Mg and $H_2$. As the halogen-containing compound, each halogen-containing compound which is described above as one of the catalyst components is usable.

The amount of each component added each time is not restricted, but in the case of an alkylating agent or a reducing agent, a preferred amount of alkylating agent (the reducing agent is regarded as the alkylating agent) added is 1 to 100 mol, more preferably 5 to 50 mol based on one mol of the chromium compound (a) used at the initiation of the oligomerization. A preferred amount of halogen-containing agent added is 0.1 to 20 mol, more preferably 1 to 10 mol based on one mol of the chromium compound (a) used at the initiation of the oligomerization.

The α-olefin oligomer is recovered by distilling off the solvent after the polymeric by-product is separated from the reaction liquid, and the α-olefin oligomer is purified, if necessary. For the purification, a distillation process is ordinarily adopted so as to recover the objective compound of a high purity.

The polymeric by-product is separated from the reaction solution by appropriately using a known solid-liquid separator. In the present invention, it is preferable to use a solid-liquid separator having a structure of discharge of the solid contents by using a rotary screw while separating the solid contents by centrifugal separation. By using the solid-liquid separator having such a structure, the separation of the powdery polymeric by-product is greatly facilitated.

A solid/liquid separator having the above-described specific structure is per se known. For example, this type of separator is commercially available under the trade name of "Sharples Super-D-Canter" (manufactured by Tomoe Kogyo Co., Ltd.). Also, various types of screw-adapted centrifuges are marketed by Ishikawajima Harima Industrial Co., Ltd.

The said solid/liquid separator is mainly composed of an external bowl having a shape of a cylinder and a cone combined integrally with each other, the said bowl being supported at its both ends by bearings and equipped with a discharge port for separating liquid and solid matter; an internal screw arranged inside of the said bowl coaxially therewith, and having equipped therearound a screw blade and a plurality of liquid spouts in the body portion; a feed tube for feeding the stock solution through the liquid spouts in the body portion of the said internal screw; a rotatory mechanism (planetary gears) designed to produce a rotational difference between the said external bowl and internal screw in the same direction; and a casing enclosing said external bowl, and having a discharge port for separating liquid and solid matter. There are two types of separator such as a vertical separator and horizontal separator.

In operation of the above solid/liquid separator, the external bowl is rotated at high speed while the internal screw is rotated at a lower speed, whereby the stock solution supplied from the feed tube is centrifuged, with the solid matter being separated to the wall surface side of the said bowl and discharged out of the system by the conveying action of the screw. In the present invention, the operating conditions of the said solid/liquid separator are not subjected to any specific restrictions, but usually the external bowl is operated at a speed of 2,000 to 6,000 r.p.m., while the internal screw is operated at a speed about 500 to 1,000 r.p.m. lower than the speed of the external bowl.

The reaction liquid is supplied to the solid-liquid separator without melting the polymeric by-product after the pressure is lowered to an appropriate pressure when the reaction is carried out under pressurization. If the polymeric by-product is dispersed by stirring the reaction liquid prior to the supply of the reaction liquid to the solid-liquid separator, it is possible to control the particle size of the polymeric by-product.

In the present invention, the reaction solution containing the catalyst components is contacted with an aqueous acidic or alkaline solution of not more than 2.5 mol/liter so as to remove the catalyst components therefrom, so that it is possible to enhance the purity of the $\alpha$-olefin oligomers.

The various substances obtained from the oligomerization reaction of $\alpha$-olefins can be applied to various uses. For instance, 1-hexene recovered from distilled $\alpha$-olefin oligomer composition can be used as a starting monomer for formation of useful polymers such as linear low-density polyethylene (L-LDPE). Also, 1-butene or butane of $C_4$, 1-octene or octane of $C_8$, etc., can be converted into corresponding sulfonic acids derivatives by adding hydrogen sulfide and oxidizing the resultant mixture. Salts of such sulfonic acids are useful as surfactant.

Thus, trying to enhance purity of the produced $\alpha$-olefin oligomers by removing the catalyst components such as chromium compound contained in the reaction mixture is important in use of the various substances obtained from the oligomerization reaction of $\alpha$-olefin. Further, depending on the conditions of distillation separation of the substances, there may arise the problems such as deposition of the catalyst components such as chromium compound on distillation column, so that it is necessary, from such aspect, to remove the catalyst components such as chromium compound contained in the reaction mixture.

As the acids for removing the catalyst components contained in the reaction mixture, nitric acid, hydrochloric acid and sulfuric acid are preferably used, and as the alkali, sodium hydroxide, potassium hydroxide and calcium hydroxide are preferably used. Such an acid or alkali is used at a low concentration such as not higher than 2.5 mol/liter. A preferred concentration of an acid is $1.0 \times 10^{-5}$ to 2.0 mol/liter, and a preferred concentration of an alkali is $3.0 \times 10^{-7}$ to 2.0 mol/liter.

Contact of the reaction mixture containing the catalyst components with an aqueous acid or alkali solution can be accomplished by using various types of extractor, but it is preferred to use an apparatus composed of a stirred tank and a stationary separating tank. Such tanks may be arranged in single stage or multiple stages. The extraction system may be either batchwise or continues.

The catalyst components easily removed by the said extraction, although variable depending on the type of extracting agent used (acid or alkali aqueous solution), are mostly chromium compound (a), the nitrogen-containing compound (b) and alkylaluminum compound (c). In the present invention, if necessary, there may be used two stirring tanks to perform extraction with both an acidic aqueous solution and an alkaline aqueous solution.

The extracting conditions are not critical, but in case of using stirring tank and stationary separating tank, a volume ratio of the oil layer to aqueous layer in the stirring tank is usually 1:0.1 to 10, preferably 1:0.5 to 5, a treating temperature is usually 25 to 60° C., preferably 40 to 60° C., and a treating time is usually 5 to 120 minutes, preferably 30 to 90 minutes.

Removal of the catalyst components can be performed at any desired stage after oligomerization. Therefore, the reaction mixture containing the catalyst components is not limited to the reaction mixture which has just been led out of the reaction system, and it may be the reaction mixture distilled off the main components of $\alpha$-olefin oligomers and/or solvent. However, in case the catalyst components are removed from the reaction mixture distilled off the great part of $\alpha$-olefin oligomers and solvent, there may arise the problems such as deposition of the catalyst components on the distillation column in the distillation separation just before the removal operation. Therefore, removal of the catalyst components needs to be conducted at a stage where the catalyst components are not yet concentrated to a high degree after distillation of the reaction mixture.

In the case of removing the catalyst components, the concentration of the chromium compound (a) in the reaction solution is preferably comparatively low. The concentration of the solvent is preferably in the range of $1.0 \times 10^{-7}$ to 0.1 mol/liter, and more preferably $2.0 \times 10^{-7}$ to 0.02 mol/liter.

Metal ions in the acidic or alkaline aqueous solution after extraction treatment can be recovered by a known method, for example, a method using a chelate resin. "Diaion CR10", "Diaion CR11" (produced by Mitsubishi Chemical Corporation), can be used as chelate resin. These chelate resins enable efficient recovery of trivalent chromium ions and aluminum ions. For recovering metal ions, it is also possible to employ a method in which the desired substances are precipitated as insoluble metals by making use of a pertinent chemical reaction, or a combination of such method and the method using a chelate resin.

In the present invention, since the concentration of the aqueous acid or alkali solution used for removing the catalyst is low, it is possible to reduce the load at the step of neutralizing the extract at the time of recovering the metal ions. In addition, since a low concentration of the aqueous acid or alkali solution is used, it is possible to recover an expensive amine from the catalyst components and to reuse the recovered amine.

That is, in the case of using a low concentration of an aqueous alkali solution, for example, since it is possible to suppress the reaction between an amine such as pyrrole and a halogen compound, it is possible to recover the expensive amine which remains in the oil layer by distillation or the like and to reuse the recovered amine. In the case of using a low concentration of an acid aqueous solution, since it is possible to suppress the polymerization reaction of an amine such as pyrrole, it is possible to recover the expensive amine by distillation after the neutralization step or the like, and to reuse the recovered amine.

The reaction mixture cleared off the catalyst components is usually washed with water to remove the acid or alkali mixed therein and then separated into $\alpha$-olefin oligomers and solvent by distillation. Such distillation separation can be accomplished by using a known distillation apparatus. The recovered solvent may be recycled to the reaction system. It is possible to produce L-LDPE, which is a useful resin, from ethylene and 1-hexene, which is produced by the process of the present invention, by a polymerization reaction using a known polymerization catalyst.

According to the present invention described above, oligomers of $\alpha$-olefin(s) such as 1-hexene can be produced in a high yield with high selectivity without complicate operations and in an industrially advantageous way. It is also possible to prevent deposition of the polymeric by-products on the reactor, distillation column, other incidental equipment, and piping. According to the present invention, it is possible to activate the catalyst in the reaction system, and to circulate the activated catalyst to the reaction system by a simple operation. Still further, according to the present invention, since it is possible to obtain 1-hexene in a high yield, distillation recovery of the reaction solvent to be recycled to the reaction system can be practiced at low load, and separation of the polymeric by-products after the reaction can be accomplished under ordinary pressure or low pressure in an industrially advantageous way.

EXAMPLE

The present invention will now be described in more detail with reference to the following examples and comparative examples, but the present invention is not restricted to those examples and various modifications are possible within the scope of the invention.

The reaction conditions in Examples 1 to 69 are collectively shown in Table 1, and the results of the reactions such as the composition analysis of α-olefin oligomer by a gas chromatography are collectively shown in Table 2.

In Tables, "Cr(2EHA)$_3$" represents chromium (III) 2-ethyl hexanoate and "Et$_3$Al" represents triethylaluminum. The symbols and the numerals in the kind of solvent, the kind of nitrogen-containing compound and the kind of halogen-containing compound represent as follows.

Kind of solvent
"CHX": cyclohexane, "HP": n-heptane, "TL": toluene

Kind of nitrogen-containing compound
(1) 2,5-dimethylpyrrole, (2) maleimide, (3) 3,4-dimethylmaleimide, (4) 3,4-dichloromaleimide Kind of halogen-containing compound
(1): CCl$_4$, (2): SnCl$_4$, (3): n-Bu$_2$SnCl$_2$, (4): Ph$_3$CCl, (5): Ph$_3$CSbCl$_6$, (6): GeCl$_4$, (7): CHCl$_3$, (8): EtAlCl$_2$, (9): Et$_2$AlCl, (10) : Et$_3$Al$_2$Cl$_3$, (11): n-Bu$_2$SnBr$_2$, (12): Cl$_2$CHCHCl$_2$, (13): CH$_2$Cl$_2$, (14): CBr$_4$, (15): CH$_2$Br$_2$, (16): C$_5$H$_{11}$Br, (17): t-BuMe$_2$SiOSO$_2$CF$_3$, (18): B(C$_6$F$_5$)$_3$, (19): CF$_3$SO$_3$H, (20): (CF$_3$)$_2$CHOH The numerals and the symbol in the contacting method in Table 1 represent as follows.

(1): Method of introducing a chromium compound and an α-olefin into a solution containing a nitrogen-containing compound, an alkylaluminum compound and a halogen-containing compound.

(2): Method of introducing an α-olefin and an alkylaluminum compound into a solution containing a chromium compound, a nitrogen-containing compound and a halogen-containing compound.

(3): Method of introducing an alkylaluminum compound, a halogen-containing compound and an α-olefin into a solution containing a chromium compound and a nitrogen-containing compound.

(4): Method of introducing a chromium compound, a halogen-containing compound and an α-olefin into a solution containing a nitrogen-containing compound and an alkylaluminum compound.

(X): Method of introducing a nitrogen-containing compound, a halogen-containing compound and an α-olefin into a solution containing a chromium compound and an alkylaluminum compound.

In Tables, the unit of the catalytic efficiency is g-α-olefin/g-chromium and the unit of the catalytic activity is g-α-olefin/g-chromium.Hr. The content of chromium metal in Cr(2EHA)$_3$ used in Examples 48 to 95 was 10.4% by weight and the content of chromium metal in Cr(2EHA)$_3$ used in Examples 1 to 47 and Comparative Examples 1 and 2 was 10.8% by weight.

Example 1

A 300-ml autoclave which was heated and dried by a dryer of 120° C. was assembled while it was hot, and the air in the autoclave was replaced by nitrogen under a vacuum. A catalyst component feed tube provided with a rupture plate was previously attached to the autoclave. It had been confirmed that the rupture plate was not burst by a pressure of nitrogen of about 5 kg/cm$^2$. 120 ml of cyclohexane, a n-heptane solution of 0.078 mmol of 2,5-dimethylpyrrole, a n-heptane solution of 8.00 mg (0.052 mmol) of carbon tetrachloride (CCl$_4$) and a n-heptane solution of 0.390 mmol of triethylaluminum were charged into the autoclave body side in that order, and a n-heptane solution of 12.5 mg (0.026 mmol) of chromium (III) 2-ethyl hexanoate was charged into the catalyst component feed tube. The total amount of n-heptane was 5 ml. At this point of time, the chromium compound was not in contact with the triethylaluminum.

The autoclave was first heated to 80° C. and ethylene was then introduced from the catalyst component feed tube at 80° C. The rupture plate was burst by the pressure of ethylene, so that the chromium compound was introduced to the autoclave body side to start the oligomerization of ethylene initiated. Ethylene was introduced until the total pressure reached 35 kg/cm$^2$ G, and thereafter, the total pressure was maintained at 35 kg/cm$^2$ G and the reaction temperature at 80° C. 30 minutes after, ethanol was injected into the autoclave to terminate the reaction. After releasing ethylene from the autoclave, the polymeric by-product (mainly polyethylene) in the reaction liquid was removed by a filter to obtain an α-olefin oligomer.

Example 2

An α-olefin oligomer was produced in the same reaction as in Example 1 except for using 13.5 mg (0.052 mmol) of tin tetrachloride (SnCl$_4$) in place of carbon tetrachloride.

Example 3

An α-olefin oligomer was produced in the same reaction as in Example 1 except for using 12.6 mg (0.041 mmol) of dibutyltin dichloride (n-Bu$_2$SnCl$_2$) in place of carbon tetrachloride.

Example 4

An α-olefin oligomer was produced in the same reaction as in Example 1 except for using 11.7 mg (0.042 mmol) of triphenylmethyl chloride (Ph$_3$CCl) in place of carbon tetrachloride.

Example 5

An α-olefin oligomer was produced in the same reaction as in Example 1 except for using 24.3 mg (0.042 mmol) of triphenylmethyl hexachloroantimonate (Ph$_3$CSbCl$_6$) in place of carbon tetrachloride.

Example 6

An α-olefin oligomer was produced in the same reaction as in Example 1 except for using 11.1 mg (0.052 mmol) of germanium tetrachloride (GeCl$_4$) in place of carbon tetrachloride.

Example 7

An α-olefin oligomer was produced in the same reaction as in Example 6 except for using 120 ml of n-heptane in place of 120 ml of cyclohexane.

Example 8

An α-olefin oligomer was produced in the same reaction as in Example 6 except for changing the order of charging the materials into the autoclave body side to the order of cyclohexane, triethylaluminum, 2,5-dimethylpyrrole, and germanium tetrachloride.

Example 9

An α-olefin oligomer was produced in the same reaction as in Example 6 except for changing the order of charging the materials into the autoclave body side to the order of cyclohexane, triethylaluminum, germanium tetrachloride and 2,5-dimethylpyrrole.

Example 10

A 2-liter autoclave which was heated and dried by a dryer of 150° C. was assembled while it was hot, and the air in the autoclave was replaced by nitrogen under a vacuum. A catalyst component feed tube provided with a rupture plate was previously attached to the autoclave. It had been confirmed that the rupture plate was not burst by a pressure of nitrogen of about 5 kg/cm$^2$. 730 ml of cyclohexane, a n-heptane solution of 0.47 mmol of 2,5-dimethylpyrrole, a n-heptane solution of 37.2 mg (0.312 mmol) of chloroform (CHCl$_3$) and a n-heptane solution of 2.3 mmol of triethylaluminum were charged into the autoclave body side in that order, and a n-heptane solution of 75.2 mg (0.156 mmol) of chromium (III) 2-ethyl hexanoate was charged into the catalyst component feed tube. The total amount of n-heptane was 20 ml. At this point of time, the chromium compound was not in contact with the triethylaluminum. An oligomerization reaction was carried out and the polymeric by-product was removed in the same procedure as in Example 1.

Example 11

A 300-ml autoclave prepared in the same procedure as in Example was used. 120 ml of cyclohexane, a n-heptane solution of 0.078 mmol of 2,5-dimethylpyrrole, a n-heptane solution of 0.39 mmol of triethylaluminum were charged into the autoclave body side in that order, and a n-heptane solution of 12.5 mg (0.026 mmol) of chromium (III) 2-ethyl hexanoate and a n-heptane solution of 8.00 mg (0.052 mmol) of carbon tetrachloride (CCl$_4$) were charged into the catalyst component feed tube. The total amount of n-heptane was 5 ml. At this point of time, the chromium compound was not in contact with the triethylaluminum. An oligomerization reaction was carried out and the polymeric by-product was removed in the same procedure as in Example 1.

Comparative Example 1

An α-olefin oligomer was produced in the same reaction as in Example 1 except that carbon tetrachloride was not added.

Comparative Example 2

A 300-ml autoclave prepared in the same procedure as in Example was used. 120 ml of cyclohexane, a n-heptane solution of 0.39 mmol of triethylaluminum and a n-heptane solution of 12.5 mg (0.026 mmol) of chromium (III) 2-ethyl hexanoate were charged into the autoclave body side in that order. At this point of time, the chromium compound was in contact with the triethylaluminum. A n-heptane solution of 0.078 mmol of 2,5-dimethylpyrrole and a n-heptane solution of 8.00 mg (0.052 mmol) of carbon tetrachloride (CCl$_4$) were charged into the catalyst component feed tube. The total amount of n-heptane was 5 ml. An oligomerization reaction was carried out and the polymeric by-product was removed in the same procedure as in Example 1.

Example 12

A 300-ml autoclave prepared in the same procedure as in Example was used. 120 ml of cyclohexane, a n-heptane solution of 0.062 mmol of maleimide, a n-heptane solution of 0.311 mmol of triethylaluminum and a n-heptane solution of 0.042 mmol of ethylaluminum dichloride (EtAlCl$_2$) were charged into the autoclave body side, and a n-heptane solution of 10 mg (0.021 mmol) of chromium (III) 2-ethyl hexanoate was charged into the catalyst component feed tube. The total amount of n-heptane was 2 ml. At this point of time, the chromium compound was not in contact with the triethylaluminum. An oligomerization reaction was carried out and the polymeric by-product was removed in the same procedure as in Example 1.

Example 13

An α-olefin oligomer was produced in the same reaction as in Example 12 except for using 3,4-dimethylmaleimide in place of maleimide.

Example 14

An α-olefin oligomer was produced in the same reaction as in Example 12 except for using 3,4-dichloromaleimide in place of maleimide.

Example 15

An α-olefin oligomer was produced in the same reaction as in Example 12 except for using diethylaluminum chloride (Et$_2$AlCl) in place of ethylaluminum dichloride.

Example 16

An α-olefin oligomer was produced in the same reaction as in Example 12 except for using sesquialuminum chloride (Et$_3$Al$_2$Cl$_3$) in place of ethylaluminum dichloride.

Example 17

An α-olefin oligomer was produced in the same reaction as in Example 12 except for using 48 ml of cyclohexane and 1 ml of toluene in place of 48 ml of cyclohexane.

Example 18

An α-olefin oligomer was produced in the same reaction as in Example 12 except for changing the amount of solvent and the amount of catalyst components. That is, 120 ml of cyclohexane, 0.156 mmol of maleimide, 0.779 mmol of triethylaluminum, 0.104 mmol of ethylaluminum dichloride, 2.5 mg (0.0052 mmol) of chromium (III) 2-ethyl hexanoate and 5 ml of n-heptane were used.

Example 19

An α-olefin oligomer was produced in the same reaction as in Example 12 except for changing the amount of ethylaluminum dichloride to 0.073 mmol.

Example 20

An α-olefin oligomer was produced in the same reaction as in Example 12 except for changing the amount of ethylaluminum dichloride to 0.208 mmol.

Example 21

An α-olefin oligomer was produced in the same reaction as in Example 12 except for changing the amount of ethylaluminum dichloride to 0.126 mmol.

Example 22

An α-olefin oligomer was produced in the same reaction as in Example 12 except for changing the amount of triethylaluminum to 0.934 mmol.

Example 23

An α-olefin oligomer was produced in the same reaction as in Example 12 except for changing the amount of catalyst components. That is, 0.108 mmol of maleimide, 0.42 mmol of triethylaluminum and 0.062 mmol of ethylaluminum dichloride were used.

Example 24

An α-olefin oligomer was produced in the same reaction as in Example 18 except that 2.5 mg (0.052 mmol) of chromium (III) 2-ethyl hexanoate was used, that the temperature at which ethylene was introduced and the reaction temperature were changed to 50° C., and that the pressure at the time of reaction was changed to 20 kg/cm$^2$G.

Example 25

An α-olefin oligomer was produced in the same reaction as in Example 12 except for using 0.032 mmol of tin tetrachloride in place of ethylaluminum dichloride.

Example 26

An α-olefin oligomer was produced in the same reaction as in Example 12 except for using 0.063 mmol of dibutyltin dichloride in place of ethylaluminum dichloride.

Example 27

An α-olefin oligomer was produced in the same reaction as in Example 12 except for using 0.084 mmol of dibutyltin dibromide (n-Bu$_2$SnBr$_2$) in place of ethylaluminum dichloride.

Example 28

An α-olefin oligomer was produced in the same reaction as in Example 12 except for using 0.021 mmol of dibutyltin dibromide in place of ethylaluminum dichloride.

Example 29

An α-olefin oligomer was produced in the same reaction as in Example 24 except that 0.104 mmol of carbon tetrachloride was used in place of ethylaluminum dichloride and that the reaction temperature was changed to 80° C.

Example 30

An α-olefin oligomer was produced in the same reaction as in Example 12 except for using 0.062 mmol of tetrachloroethane (Cl$_2$CHCHCl$_2$) in place of ethylaluminum dichloride.

Example 31

An α-olefin oligomer was produced in the same reaction as in Example 29 except for using 23.4 mmol of dichloromethane (CH$_2$Cl$_2$) in place of carbon tetrachloride.

Example 32

An α-olefin oligomer was produced in the same reaction as in Example 12 except for using 0.084 mmol of carbon tetrabromide in place of ethylaluminum dichloride.

Example 33

An α-olefin oligomer was produced in the same reaction as in Example 12 except for using 0.084 mmol of dibromomethane (CH$_2$Br$_2$) in place of ethylaluminum dichloride.

Example 34

An α-olefin oligomer was produced in the same reaction as in Example 12 except for using 0.084 mmol of pentyl bromide (C$_5$M$_{11}$Br) in place of ethylaluminum dichloride.

Example 35

An α-olefin oligomer was produced in the same reaction as in Example 12 except for using 0.084 mmol of dibutyltin dichloride and 0.021 mmol of dibutyltin dibromide in place of ethylaluminum dichloride.

Example 36

An α-olefin oligomer was produced in the same reaction as in Example 12 except for using 0.062 mmol of dibutyltin dichloride and 0.010 mmol of dibutyltin dibromide in place of ethylaluminum dichloride.

Example 37

An α-olefin oligomer was produced in the same reaction as in Example 12 except for using 0.062 mmol of dibutyltin dichloride and 0.002 mmol of dibutyltin dibromide in place of ethylaluminum dichloride.

Example 38

An α-olefin oligomer was produced in the same reaction as in Example 12 except for using 0.168 mmol of diethylaluminum chloride and 0.042 mmol of carbon tetrachloride in place of ethylaluminum dichloride.

Example 39

An α-olefin oligomer was produced in the same reaction as in Example 29 except for using 0.26 mmol of t-butyldimethylsilyl trifluoromethanesulfonate (t-BuMe$_2$SiOSO$_2$CF$_3$) in place of carbon tetrachloride.

Example 40

An α-olefin oligomer was produced in the same reaction as in Example 12 except for using 0.042 mmol of trispentafluorophenylboron (B(C$_6$F$_5$)$_3$ in place of ethylaluminum dichloride.

Example 41

An α-olefin oligomer was produced in the same reaction as in Example 12 except for using a reaction solution which was obtained by mixing 0.126 mmol of trifluoromethanesulfonic acid (CF$_3$SO$_3$H) and 0.125 mmol of triethylaluminum in n-heptane in a different vessel, in place of ethylaluminum dichloride.

Example 42

An α-olefin oligomer was produced in the same reaction as in Example 41 except for changing the amount of catalyst components reacted in the different vessel to 0.415 mmol of trifluoromethanesulfonic acid and 0.411 mmol of triethylaluminum.

Example 43

An α-olefin oligomer was produced in the same reaction as in Example 41 except for changing the amount of catalyst components reacted in the different vessel to 1.246 mmol of trifluoromethanesulfonic acid and 0.411 mmol of triethylaluminum.

Example 44

An α-olefin oligomer was produced in the same reaction as in Example 29 except for using 0.104 mmol of hexafluoroisopropanol [$(CF_3)_2CHOH$] in place of carbon tetrachloride.

Example 45

An α-olefin oligomer was produced in the same reaction as in Example 12 except for changing the place into which the catalyst components were charged. That is, cyclohexane, a n-heptane solution of maleimide, a n-heptane solution of chromium (III) 2-ethyl hexanoate and a n-heptane solution of ethylaluminum dichloride were charged into the autoclave body side, while a n-heptane solution of triethylaluminum was charged into the complex component feed tube.

Example 46

An α-olefin oligomer was produced in the same reaction as in Example 12 except for changing the place into which the catalyst components were charged. That is, cyclohexane, a n-heptane solution of maleimide, and a n-heptane solution of chromium (III) 2-ethyl hexanoate were charged into the autoclave body side, while a n-heptane solution of triethylaluminum and a n-heptane solution of ethylaluminum dichloride were charged into the complex component feed tube.

Example 47

An α-olefin oligomer was produced in the same reaction as in Example 12 except for changing the place into which the catalyst components were charged. That is, cyclohexane, a n-heptane solution of maleimide and a n-heptane solution of triethylaluminum were charged into the autoclave body side, while a n-heptane solution of chromium (III) 2-ethyl hexanoate and a n-heptane solution of ethylaluminum dichloride were charged into the complex component feed tube.

Example 48

A 2-liter autoclave which was heated and dried by a dryer of 120° C. was assembled while it was hot, and the air in the autoclave was replace by nitrogen under a vacuum. A catalyst component feed tube provided with a rupture plate was previously attached to the autoclave. It had been confirmed that the rupture plate was not burst by a pressure of nitrogen of about 5 kg/cm². 730 ml of n-heptane, a n-heptane solution of 0.140 mmol of 2,5-dimethylpyrrole, a n-heptane solution of 0.700 mmol of triethylaluminum and a n-heptane solution of 39.4 mg (0.235 mmol) of 1,1,2,2-tetrachloroethane were charged into the autoclave body side, and a n-heptane solution of 22.5 mg (0.047 mmol) of chromium (III) 2-ethyl hexanoate was charged into the catalyst component feed tube. The total amount of n-heptane was 750 ml.

The mixture of 2,5-dimethylpyrrole, triethylaluminum and 1,1,2,2-tetrachloroethane in the autoclave was first heated to 120° C. and after the mixture was held for 1.0 hour, it was cooled to 80° C. Ethylene was then introduced from the catalyst component feed tube. The rupture plate was burst by the pressure of ethylene, so that the chromium compound was introduced to the autoclave body side and the oligomerization of ethylene started. Ethylene was introduced until the total pressure reached 35 Kg/cm²G and thereafter, the total pressure was maintained at 35 Kg/cm²G and the reaction temperature at 80° C. for 0.5 hour.

After releasing ethylene from the autoclave, the polymeric by-product (mainly polyethylene) in the reaction liquid was removed by a filter so as to obtain an α-olefin oligomer.

Example 49

An α-olefin oligomer was produced in the same reaction as in Example 48 except for changing the heating temperature for the mixture of 2,5-dimethylpyrrole, triethylaluminum and 1,1,2,2-tetrachloroethane in the autoclave to 140° C.

Example 50

An α-olefin oligomer was produced in the same reaction as in Example 48 except that 730 ml of n-heptane, a n-heptane solution of 0.700 mmol of triethylaluminum and a n-heptane solution of 39.4 mg (0.235 mmol) of 1,1,2,2-tetrachloroethane were charged into the autoclave body side, and a n-heptane solution of 22.5 mg (0.047 mmol) of chromium (III) 2-ethyl hexanoate and a n-heptane solution of 0.140 mmol of 2,5-dimethylpyrrole were charged into the catalyst component feed tube, and that the mixture of triethylaluminum and 1,1,2,2-tetrachloroethane in the autoclave was heated to 120° C.

Example 51

An α-olefin oligomer was produced in the same reaction as in Example 48 except that heat treatment of the mixture of 2,5-dimethylpyrrole, triethylaluminum and 1,1,2,2-tetrachloroethane in the autoclave was not executed.

Example 52

A 2-liter autoclave which was prepared in the same procedure as in Example 48 was used, and 730 ml of n-heptane, a n-heptane solution of 0.140 mmol of 2,5-dimethylpyrrole, a n-heptane solution of 0.700 mmol of triethylaluminum and a n-heptane solution of 39.4 mg (0.235 mmol) of 1,1,2,2-tetrachloroethane were charged into the autoclave body side, while a n-heptane solution of 22.5 mg (0.047 mmol) of chromium (III) 2-ethyl hexanoate was charged into the catalyst component feed tube. The total amount of n-heptane was 750 ml. At this point of time, the chromium compound was not in contact with the triethylaluminum.

In order to prepare the volume of hydrogen in the gas phase of the autoclave to 2.8 vol %, hydrogen was first bubbled in the liquid in the autoclave under a normal pressure so as to make a hydrogen atmosphere. The autoclave was then heated to 80° C. and ethylene was introduced from the catalyst component feed tube. The rupture plate was burst by the pressure of ethylene, so that the chromium compound was introduced to the autoclave body side and the oligomerization of ethylene initiated. Ethylene was introduced until the total pressure reached 35 Kg/cm²G and thereafter, the total pressure was maintained at 35 Kg/cm²G and the reaction temperature at 80° C.

After the reaction continued for 0.5 hour, the autoclave was degassed by releasing the pressure of the autoclave. The polymeric by-product (mainly polyethylene) in the reaction liquid was removed by a filter so as to obtain an α-olefin oligomer.

Example 53

An α-olefin oligomer was produced in the same reaction as in Example 52 except that the partial pressure of ethylene was maintained at 35 Kg/cm² G and that hydrogen was supplied so that the hydrogen volume in the gas phase of the autoclave was 11.0 vol %.

Example 54

An α-olefin oligomer was produced in the same reaction as in Example 52 except that the partial pressure of ethylene was maintained at 35 Kg/cm²G and that hydrogen was supplied so that the hydrogen volume in the gas phase of the autoclave was 23.9 vol %.

Example 55

An α-olefin oligomer was produced in the same reaction as in Example 52 except that hydrogen did not exist in the gas phase of the autoclave.

Example 56

A 10-liter autoclave (continuous stirred-tank reactor, liquid content: 7.5 liter) provided with two catalyst component feed tubes and one overflow tube was heated and dried by a dryer of 150° C., and assembled while it was hot. The air in the autoclave was replaced by nitrogen under a vacuum. A n-heptane solution of 1.85 mmol/Hr of 2,5-dimethylpyrrole, a n-heptane solution of 9.0. mmol/Hr of triethylaluminum and a n-heptane solution of 3.0 mmol/Hr of 1,1,2,2,2-tetrachloroethane were continuously supplied from one catalyst component feed tube, and a n-heptane solution of 0.29 g/Hr and 0.60 mmol/Hr of chromium (III) 2-ethyl hexanoate and a mixed gas of ethylene and hydrogen (hydrogen concentration: 2.0 vol %) were continuously supplied from the other catalyst component feed tube. The total amount of n-heptane supplied was controlled to be 5.0 liter/ Hr.

The reaction pressure by the mixed gas was 35 Kg/cm²G, and the reaction temperature was 80° C. The reaction liquid obtained was caused to overflow into a pressure vessel which was connected to the autoclave, and supplied to a vertical "Sharples Super-D-Canter" (produced by Tomoe Kogyo, Co., Ltd), so as to separate the powdery polymeric by-product. The polymeric by-product was separated under the conditions that the number of revolutions of the outer bowl was 4000 rpm and the number of revolutions of the inner screw was 3500 rpm. The polymeric by-product was efficiently and smoothly separated from the reaction liquid.

Example 57

An α-olefin oligomer was continuously produced and the polymeric by-product was separated as described in Example 56 except that hydrogen was not existent in the gas phase of the autoclave. However, the polymeric by-product was not smoothly separated by the "Sharples Super-D-Canter" as in Example 56 due to the adherence of the filmy polymer to the apparatus or the like.

Example 58

A 2-liter autoclave which was heated and dried by a dryer of 120° C., was assembled while it was hot and the air in the autoclave was replaced by nitrogen under a vacuum. A catalyst component feed tube provided with a rupture plate of the burst pressure of about 5 kg/cm² and a catalyst component-supplementing tank having a capacity of 20 ml were attached to the autoclave. Not only the autoclave and the catalyst component feed tube, but also the catalyst component-supplementing tank was heated, dried and the air therein was replaced by nitrogen under a vacuum.

730 ml of n-heptane, a n-heptane solution of 0.140 mmol of 2,5-dimethylpyrrole, a n-heptane solution of 0.700 mmol of triethylaluminum and a n-heptane solution of 20.15 mg (0.094 mmol) of germanium tetrachloride were charged into the autoclave body side, while a n-heptane solution of 22.5 mg (0.047 mmol) of chromium (III) 2-ethyl hexanoate was charged into the catalyst component feed tube. The total amount of n-heptane was 750 ml. A n-heptane solution of 20.15 mg (0.094 mmol) of germanium tetrachloride was charged into the catalyst component-supplementing tank. At this point of time, the chromium compound was not in contact with the triethylaluminum.

The autoclave was first heated to 80° C. and ethylene was then introduced from the catalyst component feed tube. The rupture plate was burst by the pressure of ethylene, so that the chromium compound was introduced to the autoclave body side and the oligomerization of ethylene initiated. Ethylene was introduced until the total pressure reached 35 Kg/cm²G, and thereafter, the total pressure was maintained at 35 Kg/cm²G and the reaction temperature at 80° C. That is, an appropriate amount of ethylene for being treated in the autoclave was continuously supplied so as to maintain the total pressure at 35 Kg/cm²G.

1 hour after, the reaction liquid was sampled. Thereafter, the total amount of n-heptane of germanium tetrachloride in the catalyst component-supplementing tank was introduced to the autoclave and the reaction was continued for 1 hour under the same conditions. After releasing ethylene from the autoclave, the polymeric by-product (mainly polyethylene) in the reaction liquid was removed by a filter. The reaction liquid was recovered and the α-olefin oligomer in the reaction liquid was analyzed (Example 58B).

In each sample, after the polymeric by-product (mainly polyethylene) was removed, the sample was analyzed (Example 58A)

Example 59

An α-olefin oligomer was produced in the same reaction as in Example 58 except that a n-heptane solution of 20.15 mg (0.094 mmol) of germanium tetrachloride and a n-heptane solution of 0.700 mmol of triethylaluminum were charged into the catalyst component-supplementing tank, and that germanium tetrachloride and triethylaluminum were further added after the reaction continued 1 hour so as to further continue the reaction. The results of reactions after 1 hour and 2 hours are shown as Examples 59A and 59B, respectively.

Example 60

An α-olefin oligomer was produced in the same reaction as in Example 58 except that a n-heptane solution of 20.15 mg (0.094 mmol) of germanium tetrachloride, a n-heptane solution of 0.700 mmol of triethylaluminum and a n-heptane solution of 0.140 mmol of 2,5-dimethylpyrrole were charged into the catalyst component-supplementing tank, and that germanium tetrachloride, triethylaluminum and 2,5-dimethylpyrrole were further added after the reaction continued 1 hour so as to further continue the reaction. The results of reactions after 1 hour and 2 hours are shown as Examples 60A and 60B, respectively.

Example 61

An α-olefin oligomer was produced in the same reaction as in Example 58 except that a n-heptane solution of 0.700 mmol of triethylaluminum was charged into the catalyst component-supplementing tank, and that triethylaluminum was further added after the reaction continued 1 hour so as to further continue the reaction. The results of reaction s after 1 hour and 2 hours are shown as Examples 61A and 61, respectively.

Example 62

An α-olefin oligomer was produced in the same reaction as in Example 58 except that no catalyst component was further added. The results of reactions after 1 hour and 2 hours are shown as Examples 62A and 62B, respectively.

Example 63

An α-olefin oligomer was produced in the same reaction as in Example 58 except that no catalyst component was further added, and that molar ratio (a:b:c:d) of chromium (III) 2-ethyl hexanoate (a), 2,5-dimethylpyrrole (b), triethylaluminum (c) and germanium tetrachloride (d) was 1:3:15:4. The results of reactions after 1 hour and 2 hours are shown as Examples 63A and 63B, respectively.

Example 64

A multi-staged continuous stirred-tank reactor produced by connecting two 0.2-liter autoclaves (liquid content: 0.15 liter) by an overflow tube were used as the reaction apparatus. Two catalyst component feed tubes were attached to a first autoclave, and a catalyst component-supplementing tank was attached to the second autoclave. These autoclaves were heated and dried by a dried of 150° C. and assembled while they were hot. The air in the autoclaves was replaced by nitrogen under a vacuum.

A n-heptane solution of 6.0 mg/Hr (0.012 mmol/Hr) of chromium (III) 2-ethyl hexanoate and ethylene were continuously supplied from one catalyst component feed tube of the first autoclave, and a n-heptane solution of 0.37 mmol/Hr of 2,5-dimethylpyrrole, a n-heptane solution of 0.190 mmol/Hr of triethylaluminum and a n-heptane solution of 0.024 mmol/Hr of germanium tetrachloride were continuously supplied from the other catalyst component feed tube. The total amount of n-heptane supplied was controlled to be 0.10 liter/Hr.

The reaction pressure by the ethylene pressure was 35 Kg/cm$^2$G, and the reaction temperature was 80° C.

The reaction liquid obtained in the first autoclave was caused to overflow into the second autoclave, and a n-heptane solution of 0.190 mmol/Hr of triethylaluminum and 0.024 mmol/Hr of germanium tetrachloride was continuously supplied from the catalyst component-supplementing tank of the second autoclave at a rate of 40 ml/Hr. The reaction pressure and the reaction temperature in the second autoclave were maintained the same as those in the first autoclave. The reaction liquid flowing out of the overflow tube of the second autoclave was introduced to a pressure vessel which was connected to the overflow tube.

After releasing ethylene from the pressure vessel, the polymeric by-product (mainly polyethylene) was removed from the reaction liquid by a filter. The by-product was also removed from the reaction liquid sampled from the first autoclave in the same procedure.

Example 65

The same continuous reaction was carried out in the same procedure as in Example 64 except that no catalyst component was added to the second autoclave.

Example 66

A 2-liter autoclave which was heated and dried by a dryer of 120° C., was assembled while it was hot and the air in the autoclave was replaced by nitrogen under a vacuum. A catalyst component feed tube provided with a rupture plate of the burst pressure of about 5 kg/cm$^2$. 730 ml of n-heptane, a n-heptane solution of 0.140 mmol of 2,5-dimethylpyrrole, a n-heptane solution of 0.700 mmol of triethylaluminum and a n-heptane solution of 39.4 mg (0.235 mmol) of 1,1,2,2-tetrachloroethane were charged into the autoclave body side, while a n-heptane solution of 22.5 mg (0.047 mmol) of chromium (III) 2-ethyl hexanoate was charged into the catalyst component feed tube. The total amount of n-heptane was 750 ml. At this point of time, the chromium compound was not in contact with the triethylaluminum.

The autoclave was first heated to 80° C. and ethylene was then introduced from the catalyst component feed tube. The rupture plate was burst by the pressure of ethylene, so that the chromium compound was introduced to the autoclave body side and the oligomerization of ethylene was initiated. Ethylene was introduced until the total pressure reached 35 Kg/cm$^2$G, and thereafter, the total pressure was maintained at 35 Kg/cm$^2$G and the reaction temperature at 80° C. 0.5 hour after, the autoclave was degassed by releasing the pressure of the autoclave, and the polymeric by-product (mainly polyethylene) in the reaction liquid was removed by a filter so as to recover the reaction liquid. The α-olefin oligomer in the reaction liquid was analyzed (Example 66A).

The reaction liquid was then distilled so as to separate the $C_4$ and $C_6$ components, and 0.24 mmol of triethylaluminum was added to the remaining reaction liquid (n-heptane solution containing the catalyst components $C_8$ and $C_{10}$ to $C_6$ components) to prepare a circulating solvent containing catalyst components. Argon gas was introduced into the autoclave so as to replace the ethylene gas by the argon gas, and the circulating solvent containing catalyst components was charged into the autoclave. Ethylene was introduced to the autoclave until the total pressure reached 35 Kg/cm$^2$G. A second reaction was carried out while the total pressure was maintained at 35 Kg/cm$^2$G and the reaction temperature at 80° C. 1.0 hour after, the autoclave was degassed by releasing the pressure of the autoclave, and the polymeric by-product (mainly polyethylene) in the reaction liquid was removed by a filter. The α-olefin oligomer in the reaction liquid was analyzed (Example 66B).

Example 67

An α-olefin oligomer was produced in the first and the second reactions in the same procedure as in Example 66 except for using 0.235 mmol of 1,1,2,2-tetrachloroethane for preparing the circulating solvent containing catalyst components. The results of the first and second reactions are shown as Examples 67A and 67B, respectively.

Example 68

An α-olefin oligomer was produced in the first and the second reactions in the same procedure as in Example 66 except for using 0.701 mmol of triethylaluminum and 0.240 mmol of 1,1,2,2-tetrachloroethane for preparing the circulating solvent containing catalyst components. The results of the first and second reactions are shown as Examples 68A and 68B, respectively.

Example 69

An α-olefin oligomer was produced in the first and the second reactions in the same procedure as in Example 66 except that triethylaluminum was not used for preparing the circulating solvent containing catalyst components. The results of the first and second reactions are shown as Examples 69A and 69B, respectively.

Example 70

A 2-liter autoclave which was heated and dried by a dryer of 120° C., was assembled while it was hot and the air in the autoclave was replaced by nitrogen under a vacuum. A catalyst component feed tube provided with a rupture plate of the burst pressure of about 5 kg/cm$^2$. 730 ml of n-heptane, a n-heptane solution of 0.140 mmol of 2,5-dimethylpyrrole, a n-heptane solution of 0.700 mmol of triethylaluminum and a n-heptane solution of 39.4 mg (0.235 mmol) of 1,1,2,2-tetrachloroethane were charged into the autoclave body side, while a n-heptane solution of 22.5 mg (0.047 mmol) of chromium (III) 2-ethyl hexanoate was charged into the catalyst component feed tube. The total amount of n-heptane was 750 ml. The water content in the above n-heptane was 5 ppm (water/aluminum molar ratio was 0.25) which was produced by passing n-heptane containing 100 ppm of water through a drying column filled with molecular sieve.

After heating the autoclave to 80° C., ethylene obtained by passing through a drying column filled with molecular sieve was introduced from the catalyst component feed tube. The rupture plate was burst by the pressure of ethylene, so that the chromium compound was introduced to the autoclave body side and the oligomerization of ethylene was initiated. Ethylene was introduced until the total pressure reached 35 Kg/cm$^2$G, and thereafter, the total pressure was maintained at 35 Kg/cm$^2$G and the reaction temperature at 80° C. One hour after, the autoclave was degassed by releasing the pressure of the autoclave, and the polymeric by-product (mainly polyethylene) in the reaction liquid was removed by a filter so as to recover the reaction liquid. The α-olefin oligomer in the reaction liquid was analyzed by gas chromatography. The results of the composition analysis are shown in Table 3.

Example 71

An α-olefin oligomer was produced in the same procedure as in Example 70 except for using n-heptane containing 20 ppm of water (water/aluminum molar ratio was 1.00), which produced by passing through a drying column for shortened residence time. The results of the composition analysis are shown in Table 3.

Example 72

An α-olefin oligomer was produced in the same procedure as in Example 70 except for using n-heptane containing 40 ppm of water (water/aluminum molar ratio was 2.00), which produced by passing through a drying column for shortened residence time. The results of the composition analysis are shown in Table 4.

Example 73

An α-olefin oligomer was produced in the same procedure as in Example 70 except for using n-heptane containing 100 ppm of water (water/aluminum molar ratio was 4.00). The results of the composition analysis are shown in Table 4.

Example 74

A 2-liter autoclave which was assembled in the same procedure as in Example 48 was used, and 730 ml of cyclohexane, a n-heptane solution of 0.140 mmol of 2,5-dimethylpyrrole, a n-heptane solution of 15.7 mg (0.093 mmol) of 1,1,2,2-tetrachloroethane, a n-heptane solution of 0.70 mmol of triethylaluminum were charged into the autoclave body side in that order, while a n-heptane solution of 22.5 mg (0.047 mmol) of chromium (III) 2-ethyl hexanoate was charged into the catalyst component feed tube. The total amount of n-heptane was 20 ml. At this point of time, the chromium compound was not in contact with the triethylaluminum.

The autoclave was first heated to 80° C. and ethylene was introduced from the catalyst component feed tube at 80° C. The rupture plate was burst by the pressure of ethylene, so that the chromium compound was introduced to the autoclave body side and the oligomerization of ethylene was initiated. Ethylene was introduced until the total pressure reached 35 kg/cm$^2$G, and thereafter, the total pressure was maintained at 35 kg/cm$^2$G and the reaction temperature at 80° C.

After the reaction continued for a predetermined time, the autoclave was degassed by releasing the pressure of the autoclave. The polymeric by-product (mainly polyethylene) in the reaction liquid was recovered. The results of the reactions are shown in Table 5.

Example 75

An α-olefin oligomer was produced in the same reaction as in Example 74 except for using 20.0 mg (0.093 mmol) of germanium tetrachloride (GeCl$_4$) in place of 1,1,2,2-tetrachloroethane. The results of the reactions are shown in Table 6.

Example 76

An α-olefin oligomer was produced in the same reaction as in Example 74 except for using 14.4 mg (0.093 mmol) of carbon tetrachloride (CCl$_4$) in place of 1,1,2,2-tetrachloroetnane. The amount of 1-hexane recovered was 350 ml and the content of halogen therein was 2 ppm. The results of the reactions are shown in Table 7.

Example 77

An α-olefin oligomer was produced in the same reaction as in Example 74 except for changing the amount of 1,1,2,2-tetrachloroethane used to 39.2 mg (0.234 mmol). The amount of 1-hexane recovered was 530 ml and the content of halogen therein was 28 ppm. The results of the reactions are shown in Table 8.

Example 78

An α-olefin oligomer was produced in the same reaction as in Example 77 except for using 750 ml of n-heptane as the solvent. The results of the reactions are shown in Table 9.

Example 79

An α-olefin oligomer was produced in the same reaction as in Example 78 except for changing the amount of each catalyst component used to the amount shown in Table 6. The results of the reactions are shown in Table 10.

Example 80

An α-olefin oligomer was produced in the same reaction as in Example 78 except for using 12.1 mg (0.093 mmol) of 1,1,1-trichloroethane in place of 1,1,2,2-tetrachloroethane. The results of the reactions are shown in Table 11.

Example 81

A 2-liter autoclave which was prepared in the same procedure as in Example 48 was used, and 730 ml of cyclohexane, a n-heptane solution of 0.140 mmol of 2,5-dimethylpyrrole, a n-heptane solution of 27.3 mg (0.093 mmol) of 1,2,3,4,5,6-hexachlorocyclohexane, a n-heptane solution of 0.701 mmol of triethylaluminum were charged into the autoclave body side in that order, while a n-heptane solution of 22.5 mg (0.047 mmol) of chromium (III) 2-ethyl hexanoate was charged into the catalyst component feed tube. The total amount of n-heptane was 20 ml. At this point of time, the chromium compound was not in contact with the triethylaluminum.

The autoclave was first heated to 80° C. and ethylene was introduced from the catalyst component feed tube at 80° C. The rupture plate was burst by the pressure of ethylene, so that the chromium compound was introduced to the autoclave body side and the oligomerization of ethylene was initiated. Ethylene was introduced until the total pressure reached 35 kg/cm$^2$G, and thereafter, the total pressure was maintained at 35 kg/cm$^2$G and the reaction temperature at 80° C.

After the reaction continued for a predetermined time, each reaction liquid was sampled. After the reaction, the autoclave was degassed by releasing the pressure of the autoclave. The polymeric by-product (mainly polyethylene) in the reaction liquid was recovered. The result of the reaction is shown in Table 12. A change of the catalytic efficiency with time is shown in FIG. 1, numeral 1.

Example 82

An α-olefin oligomer was produced in the same reaction as in Example 81 except for using 19.9 mg (0.093 mmol) of pentachlorocyclopropane in place of 1,2,3,4,5,6-hexachlorocyclohexane. The results of the reactions are shown in Table 13. A change of the catalytic efficiency with time is shown in FIG. 1, numeral 2.

Example 83

An α-olefin oligomer was produced in the same reaction as in Example 81 except for using 20.0 mg (0.093 mmol) of germanium tetrachloride (GeCl$_4$) in place of 1,2,3,4,5,6-hexachlorocyclohexane. The results of the reactions are shown in Table 14. A change of the catalytic efficiency with time is shown in FIG. 1, numeral 3.

Example 84

An α-olefin oligomer was produced in the same reaction as in Example 81 except for using 14.4 mg (0.093 mmol) of carbon tetrachloride (CCl$_4$) in place of 1,2,3,4,5,6-hexachlorocyclohexane. The results of the reactions are shown in Table 15. A change of the catalytic efficiency with time is shown in FIG. 1, numeral 4.

Example 85

A 2-liter autoclave which was prepared in the same procedure as in Example 10 was used, and 480 ml of n-heptane, a n-heptane solution of 0.30 mmol of 2,5-dimethylpyrrole, a n-heptane solution of 1.52 mmol of triethylaluminum and a n-heptane solution of 0.50 mmol of 1,1,2,2-tetrachloroethane were charged into the autoclave body side, while a n-heptane solution of 0.10 mmol of chromium (III) 2-ethyl hexanoate was charged into the catalyst component feed tube. The total amount of n-heptane was 500 ml. At this point of time, the chromium compound was not in contact with the triethylaluminum.

The autoclave was first heated to 80° C. and ethylene was introduced from the catalyst component feed tube at 80° C. The rupture plate was burst by the pressure of ethylene, so that the chromium compound was introduced to the autoclave body side and the oligomerization of ethylene initiated. Ethylene was introduced until the total pressure reached 35 kg/cm$^2$G, and thereafter, the total pressure was maintained at 35 kg/cm$^2$G and the reaction temperature at 80° C. That is, an appropriate amount of ethylene for being treated in the autoclave was continuously supplied so as to maintain the total pressure at 35 kg/cm$^2$G.

After the reaction continued for 30 minutes, the autoclave was degassed by releasing the pressure of the autoclave. The polymeric by-product (56.1 mg) in the reaction liquid was removed under the nitrogen atmosphere by a filter so as to obtain an α-olefin oligomer. As a result of measurement of the components of the removed polymer by a high-frequency plasma emission spectrophotometer "ICAP-88" (manufactured by Japan Jarrey Ashe Corporation) (hereinunder referred to as "ICP analysis"), it was found that 8.5 wt % of Cr and 1.1 wt % of Al based on the amount of charged material were contained. As a result of analysis of the composition of the α-olefin oligomer in the reaction liquid by a gas chromatography, it as found that the catalytic activity was 116, 143 (g-α-olefin/g-Cr.hr), the C$_6$ content in the total product was 85.2 wt %, and the 1-hexene content in C$_6$ was 97.6 wt %.

A part (50 ml) of reaction liquid was collected under a nitrogen atmosphere, and the catalyst components were extracted under the nitrogen atmosphere by using nitric acid (50 ml) having a concentration shown in Table 16. At this time, the volume ratio of the oil layer to the water layer was 1:1, the extraction temperature was 20° C. and treatment time was 30 minutes. The organic layer was further washed with water, and the content of each catalyst component in each of the acid layer (extracting layer) used for extraction, the washing liquid used for washing the extracting layer with water, and the organic layer was measured by ICP analysis. The results of analysis are shown in Table 16.

Examples 86 and 87

An α-olefin oligomer was produced in the same reaction as in Example 85 except for using an acid having a concentration shown in Table 16 as an extracting liquid of the catalyst components. The results of analysis are shown in Table 16.

Examples 88 and 89

An α-olefin oligomer was produced in the same reaction as in Example 85 except for using an aqueous sodium hydroxide having a concentration shown in Table 17 as an extracting liquid of the catalyst components. The results of analysis are shown in Table 17.

Example 90

An α-olefin oligomer was produced in the same reaction as in Example 88 except for using a n-heptane solution of 0.19 mmol/l of chloroform in place of the n-heptane solution of 1,1,2,2-tetrachloroethane. The results of analysis are shown in Table 17.

Example 91

An α-olefin oligomer was produced, a polymeric by-product was separated and the catalyst components were extracted in the same reaction as in Example 85 except that 970 ml of n-heptane, a n-heptane solution of 1.24 mmol of 2,5-dimethylpyrrole, a n-heptane solution of 2.00 mmol of triethylaluminum were charged into the autoclave body side, while a n-heptane solution of 0.40 mmol of chromium (III) 2-ethyl hexanoate was charged into the catalyst component feed tube (the total amount of n-heptane was 1 liter), that the reaction temperature was changed to 60° C., and that the extracting liquid was changed to 1.4 mol/liter of hydrochloric acid. The results of analysis are shown in Table 18.

Example 92

An α-olefin oligomer was produced in the same reaction as in Example 91 except for using 1.2 mol/liter of aqueous sodium hydroxide solution in place of 1.4 mol/liter of hydrochloric acid. The results of analysis are shown in Table 18.

Example 93

A 2-liter autoclave which was heated and dried by a dryer of 120° C., was assembled while it was hot and the air in the autoclave was replaced by nitrogen under a vacuum. A catalyst component feed tube provided with a rupture plate of the burst pressure of about 5 kg/cm$^2$. 730 ml of n-heptane, a n-heptane solution of 0.140 mmol of 2,5-dimethylpyrrole, a n-heptane solution of 0.700 mmol of triethylaluminum and a n-heptane solution of 18.0 mg (0.234 mmol) of allyl chloride were charged into the autoclave body side, while a n-heptane solution of 22.5 mg (0.047 mmol) of chromium (III) 2-ethyl hexanoate was charged into the catalyst component feed tube. The total amount of n-heptane was 750 ml. At this point of time, the chromium compound was not in contact with the triethylaluminum.

After heating the autoclave to 80° C., ethylene was introduced from the catalyst component feed tube. The rupture plate was burst by the pressure of ethylene, so that the chromium compound was introduced to the autoclave body side and the oligomerization of ethylene was initiated. Ethylene was introduced until the total pressure reached 35 Kg/cm$^2$G, and thereafter, the total pressure was maintained at 35 Kg/cm$^2$G and the reaction temperature at 80° C.

After prescribed reaction time (0.5 hour), a part of reaction liquid was collected in a nitrogen atmosphere. After completion of the reaction, the autoclave was degassed by releasing the pressure of the autoclave, and the polymeric by-product (mainly polyethylene) in the reaction liquid was removed by a filter so as to recover the reaction solution. The α-olefin oligomer in the reaction liquid was analyzed by gas chromatography. The results of the composition analysis are shown in Table 19.

The obtained reaction solution (1,000 ml) was distilled by a glass distilling column (inner diameter: 32 mm⌀, number of stages: 20). The distillation was conducted in batchwise process in which R/D ratio was 2 and the operating pressure was 760 mmHg. The amount of 1-hexene recovered was 330 ml. The content of halogen in the recovered 1-hexene was measured by a micro sulfur and chlorine analyzer (Mitsubishi chemical Corporation) and halogen could not be detected.

Examples 94 and 95

An α-olefin oligomer was produced in the same procedure as in Example 83 except for the prescribed reaction time. The results of analysis are shown in Table 19.

TABLE 1

| | Example 1 | Example 2 | Example 3 |
|---|---|---|---|
| Type of solvent (Amount: ml) | CHX (120) HP (5) | CHX (120) HP (5) | CHX (120) HP (5) |
| Amount (mg) of Cr(2EHA)$_3$ | 12.5 | 12.5 | 10.0 |
| Cr(2EHA)$_3$ (a) (mmol) | 0.026 | 0.026 | 0.021 |
| Type of nitrogen-containing compound | (1) | (1) | (1) |
| Nitrogen-containing compound (b) (mmol) | 0.078 | 0.078 | 0.063 |
| Et$_3$Al (c) (mmol) | 0.390 | 0.390 | 0.310 |
| Type of halogen-containing compound | (1) | (2) | (3) |
| Halogen-containing compound (d) (mmol) | 0.052 | 0.052 | 0.042 |
| Molar ratio (a:b:c:d) of catalyst components | 1:3:15:2 | 1:3:15:2 | 1:3:15:2 |
| Reaction temperature (° C.) | 80 | 80 | 80 |
| Ethylene pressure (Kg/cm$^2$G) | 35 | 35 | 35 |
| Residence time (Hr) | 0.5 | 0.5 | 0.5 |
| Contacting method | (1) | (1) | (1) |

| | Example 4 | Example 5 | Example 6 |
|---|---|---|---|
| Type of solvent (Amount: ml) | CHX (46) HP (4) | CHX (46) HP (4) | CHX (120) HP (5) |
| Amount (mg) of Cr(2EHA)$_3$ | 10.0 | 10.0 | 12.5 |
| Cr(2EHA)$_3$ (a) (mmol) | 0.021 | 0.021 | 0.026 |
| Type of nitrogen-containing compound | (1) | (1) | (1) |
| Nitrogen-containing compound (b) (mmol) | 0.063 | 0.063 | 0.078 |
| Et$_3$Al (c) (mmol) | 0.310 | 0.310 | 0.390 |
| Type of halogen-containing compound | (4) | (5) | (6) |
| Halogen-containing compound (d) (mmol) | 0.042 | 0.042 | 0.052 |
| Molar ratio (a:b:c:d) of catalyst components | 1:3:15:2 | 1:3:15:2 | 1:3:15:2 |
| Reaction temperature (° C.) | 80 | 80 | 80 |
| Ethylene pressure (Kg/cm$^2$G) | 35 | 35 | 35 |
| Residence time (Hr) | 0.5 | 0.5 | 0.5 |

TABLE 1-continued

| | Example 7 | Example 8 | Example 9 |
|---|---|---|---|
| Type of solvent (Amount: ml) | HP (125) | CHX (120) HP (5) | CHX (120) HP (5) |
| Amount (mg) of Cr(2EHA)₃ | 12.5 | 12.5 | 12.5 |
| Cr(2EHA)₃ (a) (mmol) | 0.026 | 0.026 | 0.026 |
| Type of nitrogen-containing compound | (1) | (1) | (1) |
| Nitrogen-containing compound (b) (mmol) | 0.078 | 0.078 | 0.078 |
| Et₃Al (c) (mmol) | 0.390 | 0.390 | 0.390 |
| Type of halogen-containing compound | (6) | (6) | (6) |
| Halogen-containing compound (d) (mmol) | 0.052 | 0.052 | 0.052 |
| Molar ratio (a:b:c:d) of catalyst components | 1:3:15:2 | 1:3:15:2 | 1:3:15:2 |
| Reaction temperature (° C.) | 80 | 80 | 80 |
| Ethylene pressure (Kg/cm²G) | 35 | 35 | 35 |
| Residence time (Hr) | 0.5 | 0.5 | 0.5 |
| Contacting method | (1) | (1) | (1) |

| | Example 10 | Example 11 |
|---|---|---|
| Type of solvent (Amount: ml) | CHX (730) HP (20) | CHX (120) HP (5) |
| Amount (mg) of Cr(2EHA)₃ | 75.2 | 12.5 |
| Cr(2EHA)₃ (a) (mmol) | 0.156 | 0.026 |
| Type of nitrogen-containing compound | (1) | (1) |
| Nitrogen-containing compound (b) (mmol) | 0.470 | 0.078 |
| Et₃Al (c) (mmol) | 2.300 | 0.390 |
| Type of halogen-containing compound | (7) | (1) |
| Halogen-containing compound (d) (mmol) | 0.312 | 0.052 |
| Molar ratio (a:b:c:d) of catalyst components | 1:3:15:2 | 1:3:15:2 |
| Reaction temperature (° C.) | 80 | 80 |
| Ethylene pressure (Kg/cm²G) | 35 | 35 |
| Residence time (Hr) | 0.5 | 0.5 |
| Contacting method | (1) | (1) |

| | Comp. Example 1 | Comp. Example 2 |
|---|---|---|
| Type of solvent (Amount: ml) | CHX (120) HP (5) | CHX (120) HP (5) |
| Amount (mg) of Cr(2EHA)₃ | 12.5 | 12.5 |
| Cr(2EHA)₃ (a) (mmol) | 0.026 | 0.026 |
| Type of nitrogen-containing compound | (1) | (1) |
| Nitrogen-containing compound (b) (mmol) | 0.078 | 0.078 |
| Et₃Al (c) (mmol) | 0.390 | 0.390 |
| Type of halogen-containing compound | — | (1) |
| Halogen-containing compound (d) (mmol) | — | 0.052 |
| Molar ratio (a:b:c:d) of catalyst components | 1:3:15:0 | 1:3:15:2 |
| Reaction temperature (° C.) | 80 | 80 |
| Ethylene pressure (Kg/cm²G) | 35 | 35 |
| Residence time (Hr) | 0.5 | 0.5 |
| Contacting method | (1) | (X) |

| | Example 12 | Example 13 | Example 14 |
|---|---|---|---|
| Type of solvent (Amount: ml) | CHX (48) HP (2) | CHX (48) HP (2) | CHX (48) HP (2) |
| Amount (mg) of Cr(2EHA)₃ | 10.0 | 10.0 | 10.0 |
| Cr(2EHA)₃ (a) (mmol) | 0.021 | 0.021 | 0.021 |
| Type of nitrogen-containing compound | (2) | (3) | (4) |
| Nitrogen-containing compound (b) (mmol) | 0.062 | 0.062 | 0.062 |
| Et₃Al (c) (mmol) | 0.311 | 0.311 | 0.311 |
| Type of halogen-containing compound | (8) | (8) | (8) |
| Halogen-containing compound (d) (mmol) | 0.042 | 0.042 | 0.042 |
| Molar ratio (a:b:c:d) of catalyst components | 1:3:15:2 | 1:3:15:2 | 1:3:15:2 |
| Reaction | 80 | 80 | 80 |

TABLE 1-continued

| | Example 15 | Example 16 | Example 17 |
|---|---|---|---|
| temperature (° C.) | | | |
| Ethylene pressure (Kg/cm²G) | 35 | 35 | 35 |
| Residence time (Hr) | 0.5 | 0.5 | 0.5 |
| Contacting method | (1) | (1) | (1) |
| Type of solvent (Amount: ml) | CHX (48) HP (2) | CHX (48) HP (2) | CHX(48) HP (2) TL (1) |
| Amount (mg) of Cr(2EHA)$_3$ | 10.0 | 10.0 | 10.0 |
| Cr(2EHA)$_3$ (a) (mmol) | 0.021 | 0.021 | 0.021 |
| Type of nitrogen-containing compound | (2) | (2) | (2) |
| Nitrogen-containing compound (b) (mmol) | 0.062 | 0.062 | 0.062 |
| Et$_3$Al (c) (mmol) | 0.311 | 0.311 | 0.311 |
| Type of halogen-containing compound | (9) | (10) | (8) |
| Halogen-containing compound (d) (mmol) | 0.042 | 0.042 | 0.042 |
| Molar ratio (a:b:c:d) of catalyst components | 1:3:15:2 | 1:3:15:2 | 1:3:15:2 |
| Reaction temperature (° C.) | 80 | 80 | 80 |
| Ethylene pressure (Kg/cm²G) | 35 | 35 | 35 |
| Residence time (Hr) | 0.5 | 0.5 | 0.5 |
| Contacting method | (1) | (1) | (1) |

| | Example 18 | Example 19 | Example 20 |
|---|---|---|---|
| Type of solvent (Amount: ml) | CHX (120) HP (5) | CHX (48) HP (2) | CHX (48) HP (2) |
| Amount (mg) of Cr(2EHA)$_3$ | 2.50 | 10.0 | 10.0 |
| Cr(2EHA)$_3$ (a) (mmol) | 0.0052 | 0.021 | 0.021 |
| Type of nitrogen-containing compound | (2) | (2) | (2) |
| Nitrogen-containing compound (b) (mmol) | 0.156 | 0.062 | 0.062 |
| Et$_3$Al (c) (mmol) | 0.779 | 0.311 | 0.311 |
| Type of halogen-containing compound | (8) | (8) | (8) |
| Halogen-containing compound (d) (mmol) | 0.104 | 0.073 | 0.208 |
| Molar ratio (a:b:c:d) of catalyst components | 1:3:15:2 | 1:3:15:3.5 | 1:3:15:10 |
| Reaction temperature (° C.) | 80 | 80 | 80 |
| Ethylene pressure (Kg/cm²G) | 35 | 35 | 35 |
| Residence time (Hr) | 0.5 | 0.5 | 0.5 |
| Contacting method | (1) | (1) | (1) |

| | Example 21 | Example 22 | Example 23 |
|---|---|---|---|
| Type of solvent (Amount: ml) | CHX (48) HP (2) | CHX (48) HP (2) | CHX (48) HP (2) |
| Amount (mg) of Cr(2EHA)$_3$ | 10.0 | 10.0 | 10.0 |
| Cr(2EHA)$_3$ (a) (mmol) | 0.021 | 0.021 | 0.021 |
| Type of nitrogen-containing compound | (2) | (2) | (2) |
| Nitrogen-containing compound (b) (mmol) | 0.062 | 0.062 | 0.108 |
| Et$_3$Al (c) (mmol) | 0.311 | 0.934 | 0.420 |
| Type of halogen-containing compound | (8) | (8) | (8) |
| Halogen-containing compound (d) (mmol) | 0.126 | 0.042 | 0.062 |
| Molar ratio (a:b:c:d) of catalyst components | 1:3:15:6 | 1:3:44:2 | 1:5:20:3 |
| Reaction temperature (° C.) | 80 | 80 | 80 |
| Ethylene pressure (Kg/cm²G) | 20 | 35 | 35 |
| Residence time (Hr) | 0.5 | 0.5 | 0.5 |
| Contacting method | (1) | (1) | (1) |

| | Example 24 | Example 25 | Example 26 |
|---|---|---|---|
| Type of solvent (Amount: ml) | CHX (120) HP (5) | CHX (48) HP (2) | CHX (48) HP (2) |
| Amount (mg) of Cr(2EHA)$_3$ | 25.0 | 10.0 | 10.0 |
| Cr(2EHA)$_3$ (a) (mmol) | 0.052 | 0.021 | 0.021 |
| Type of nitrogen-containing compound | (2) | (2) | (2) |
| Nitrogen-containing compound (b) (mmol) | 0.156 | 0.062 | 0.062 |
| Et$_3$Al (c) (mmol) | 0.779 | 0.311 | 0.311 |
| Type of halogen-containing compound | (8) | (2) | (3) |
| Halogen-containing compound (d) (mmol) | 0.104 | 0.032 | 0.063 |

TABLE 1-continued

| | Example 24 | Example 25 | Example 26 |
|---|---|---|---|
| (d) (mmol) | | | |
| Molar ratio (a:b:c:d) of catalyst components | 1:3:15:2 | 1:3:15:1.5 | 1:3:15:3 |
| Reaction temperature (° C.) | 50 | 80 | 80 |
| Ethylene pressure (Kg/cm²G) | 35 | 35 | 35 |
| Residence time (Hr) | 0.5 | 0.5 | 0.5 |
| Contacting method | (1) | (1) | (1) |

| | Example 27 | Example 28 | Example 29 |
|---|---|---|---|
| Type of solvent (Amount: ml) | CHX (48) HP (2) | CHX (48) HP (2) | CHX (120) HP (5) |
| Amount (mg) of Cr(2EHA)₃ | 10.0 | 10.0 | 10.0 |
| Cr(2EHA)₃ (a) (mmol) | 0.021 | 0.021 | 0.052 |
| Type of nitrogen-containing compound | (2) | (2) | (2) |
| Nitrogen-containing compound (b) (mmol) | 0.062 | 0.062 | 0.156 |
| Et₃Al (c) (mmol) | 0.311 | 0.311 | 0.779 |
| Type of halogen-containing compound | (11) | (11) | (1) |
| Halogen-containing compound (d) (mmol) | 0.084 | 0.021 | 0.104 |
| Molar ratio (a:b:c:d) of catalyst components | 1:3:15:4 | 1:3:15:1 | 1:3:15:2 |
| Reaction temperature (° C.) | 80 | 80 | 80 |
| Ethylene pressure (Kg/cm²G) | 35 | 35 | 35 |
| Residence time (Hr) | 0.5 | 0.5 | 0.5 |
| Contacting method | (1) | (1) | (1) |

| | Example 30 | Example 31 | Example 32 |
|---|---|---|---|
| Type of solvent (Amount: ml) | CHX (48) HP (2) | CHX (120) HP (5) | CHX (48) HP (2) |
| Amount (mg) of Cr(2EHA)₃ | 10.0 | 25.0 | 10.0 |
| Cr(2EHA)₃ (a) (mmol) | 0.021 | 0.052 | 0.021 |
| Type of nitrogen-containing compound | (2) | (2) | (2) |
| Nitrogen-containing compound (b) (mmol) | 0.062 | 0.156 | 0.062 |
| Et₃Al (c) (mmol) | 0.311 | 0.779 | 0.311 |
| Type of halogen-containing compound (1) | (12) | (13) | (14) |
| Halogen-containing compound (1) (d) (mmol) | 0.062 | 23.4 | 0.084 |
| Molar ratio (a:b:c:d) of catalyst components | 1:3:15:3 | 1:3:15:450 | 1:3:15:4 |
| Reaction temperature (° C.) | 80 | 80 | 80 |
| Ethylene pressure (Kg/cm²G) | 35 | 35 | 35 |
| Residence time (Hr) | 0.5 | 0.5 | 0.5 |
| Contacting method | (1) | (1) | (1) |

| | Example 33 | Example 34 | Example 35 |
|---|---|---|---|
| Type of solvent (Amount: ml) | CHX (48) HP (2) | CHX (48) HP (2) | CHX (48) HP (2) |
| Amount (mg) of Cr(2EHA)₃ | 10.0 | 10.0 | 10.0 |
| Cr(2EHA)₃ (a) (mmol) | 0.021 | 0.021 | 0.021 |
| Type of nitrogen-containing compound | (2) | (2) | (2) |
| Nitrogen-containing compound (b) (mmol) | 0.062 | 0.062 | 0.062 |
| Et₃Al (c) (mmol) | 0.311 | 0.311 | 0.311 |
| Type of halogen-containing compound (1) | (15) | (16) | (3) |
| Halogen-containing compound (1) (d) (mmol) | 0.084 | 0.084 | 0.084 |
| Type of halogen-containing compound (2) | — | — | (9) |
| Halogen-containing compound (2) (d) (mmol) | — | — | 0.021 |
| Molar ratio (a:b:c:d) of catalyst components | 1:3:15:4 | 1:3:15:4 | 1:3:15:5 |
| Reaction temperature (° C.) | 80 | 80 | 80 |
| Ethylene pressure (Kg/cm²G) | 35 | 35 | 35 |
| Residence time (Hr) | 0.5 | 0.5 | 0.5 |
| Contacting method | (1) | (1) | (1) |

| | Example 36 | Example 37 | Example 38 |
|---|---|---|---|
| Type of solvent (Amount: ml) | CHX (48) HP (2) | CHX (48) HP (2) | CHX (48) HP (2) |
| Amount (mg) of Cr(2EHA)₃ | 10.0 | 10.0 | 10.0 |
| Cr(2EHA)₃ (a) (mmol) | 0.021 | 0.021 | 0.021 |
| Type of | (2) | (2) | (2) |

TABLE 1-continued

|  | | | |
|---|---|---|---|
| nitrogen-containing compound | | | |
| Nitrogen-containing compound (b) (mmol) | 0.062 | 0.062 | 0.062 |
| Et₃Al (c) (mmol) | 0.311 | 0.311 | 0.311 |
| Type of halogen-containing compound (1) | (3) | (3) | (9) |
| Halogen-containing compound (1) (d) (mmol) | 0.062 | 0.062 | 0.168 |
| Type of halogen-containing compound (2) | (9) | (9) | (14) |
| Halogen-containing compound (2) (d) (mmol) | 0.010 | 0.002 | 0.042 |
| Molar ratio (a:b:c:d) of catalyst components | 1:3:15:3.5 | 1:3:15:3 | 1:3:15:10 |
| Reaction temperature (° C.) | 80 | 80 | 80 |
| Ethylene pressure (Kg/cm²G) | 35 | 35 | 35 |
| Residence time (Hr) | 0.5 | 0.5 | 0.5 |
| Contacting method | (1) | (1) | (1) |

|  | Example 39 | Example 40 | Example 41 |
|---|---|---|---|
| Type of solvent (Amount: ml) | CHX (120) HP (5) | CHX (48) HP (2) | CHX (48) HP (2) |
| Amount (mg) of Cr(2EHA)₃ | 10.0 | 10.0 | 10.0 |
| Cr(2EHA)₃ (a) (mmol) | 0.052 | 0.021 | 0.021 |
| Type of nitrogen-containing compound | (2) | (2) | (2) |
| Nitrogen-containing compound (b) (mmol) | 0.156 | 0.062 | 0.062 |
| Et₃Al (c) (mmol) | 0.779 | 0.311 | 0.436 |
| Type of halogen-containing compound (1) | (17) | (18) | (19) |
| Halogen-containing compound (1) (d) (mmol) | 0.260 | 0.042 | 0.126 |
| Molar ratio (a:b:c:d) of catalyst components | 1:3:15:5 | 1:3:15:2 | 1:3:20:6 |
| Reaction temperature (° C.) | 80 | 80 | 80 |
| Ethylene pressure (Kg/cm²G) | 35 | 35 | 35 |
| Residence time (Hr) | 0.5 | 0.5 | 0.5 |
| Contacting method | (1) | (1) | (1) |

|  | Example 42 | Example 43 | Example 44 |
|---|---|---|---|
| Type of solvent (Amount: ml) | CHX (48) HP (2) | CHX (48) HP (2) | CHX (120) HP (5) |
| Amount (mg) of Cr(2EHA)₃ | 10.0 | 10.0 | 25.0 |
| Cr(2EHA)₃ (a) (mmol) | 0.021 | 0.021 | 0.052 |
| Type of nitrogen-containing compound | (2) | (2) | (2) |
| Nitrogen-containing compound (b) (mmol) | 0.062 | 0.062 | 0.156 |
| Et₃Al (c) (mmol) | 0.722 | 0.722 | 0.779 |
| Type of halogen-containing compound | (19) | (19) | (20) |
| Halogen-containing compound (d) (mmol) | 0.415 | 1.246 | 0.104 |
| Molar ratio (a:b:c:d) of catalyst components | 1:3:34:20 | 1:3:34:60 | 1:3:15:2 |
| Reaction temperature (° C.) | 80 | 80 | 80 |
| Ethylene pressure (Kg/cm²G) | 35 | 35 | 35 |
| Residence time (Hr) | 0.5 | 0.5 | 0.5 |
| Contacting method | (1) | (1) | (1) |

|  | Example 45 | Example 46 | Example 47 |
|---|---|---|---|
| Type of solvent (Amount: ml) | CHX (48) HP (2) | CHX (48) HP (2) | CHX (48) HP (2) |
| Amount (mg) of Cr(2EHA)₃ | 10.0 | 10.0 | 10.0 |
| Cr(2EHA)₃ (a) (mmol) | 0.021 | 0.021 | 0.021 |
| Type of nitrogen-containing compound | (2) | (2) | (2) |
| Nitrogen-containing compound (b) (mmol) | 0.062 | 0.062 | 0.062 |
| Et₃Al (c) (mmol) | 0.311 | 0.311 | 0.311 |
| Type of halogen-containing compound | (8) | (8) | (8) |
| Halogen-containing compound (d) (mmol) | 0.042 | 0.042 | 0.042 |
| Molar ratio (a:b:c:d) of catalyst components | 1:3:15:2 | 1:3:15:2 | 1:3:15:2 |
| Reaction temperature (° C.) | 80 | 80 | 80 |

TABLE 1-continued

|  | | | |
|---|---|---|---|
| Ethylene pressure (Kg/cm²G) | 35 | 35 | 35 |
| Residence time (Hr) | 0.5 | 0.5 | 0.5 |
| Contacting method | (2) | (3) | (4) |

|  | Example 48 | Example 49 |
|---|---|---|
| Heating pretreatment: Temperature (° C.) × Time (hr) | 120 × 1 | 140 × 1 |
| Type of solvent (Amount: ml) | HP (750) | HP (750) |
| Amount (mg) of Cr(2EHA)₃ | 22.5 | 22.5 |
| Cr(2EHA)₃ (a) (mmol) | 0.047 | 0.047 |
| Type of nitrogen-containing compound | (1) | (1) |
| Nitrogen-containing compound (b) (mmol) | 0.140 | 0.140 |
| Et₃Al (c) (mmol) | 0.701 | 0.701 |
| Type of halogen-containing compound | (12) | (12) |
| Halogen-containing compound (d) (mmol) | 0.240 | 0.240 |
| Molar ratio (a:b:c:d) of catalyst components | 1:3:15:5 | 1:3:15:5 |
| Reaction temperature (° C.) | 80 | 80 |
| Ethylene pressure (Kg/cm²G) | 35 | 35 |
| Residence time (Hr) | 0.5 | 0.5 |
| Contacting method | (1) | (1) |

|  | Example 50 | Example 51 |
|---|---|---|
| Heating pretreatment: Temperature (° C.) × Time (hr) | 120 × 1 | None |
| Type of solvent (Amount: ml) | HP (750) | HP (750) |
| Amount (mg) of Cr(2EHA)₃ | 22.5 | 22.5 |
| Cr(2EHA)₃ (a) (mmol) | 0.047 | 0.047 |
| Type of nitrogen-containing compound | (1) | (1) |
| Nitrogen-containing compound (b) (mmol) | 0.140 | 0.140 |
| Et₃Al (c) (mmol) | 0.701 | 0.701 |
| Type of halogen-containing compound | (12) | (12) |
| Halogen-containing compound (d) (mmol) | 0.240 | 0.240 |
| Molar ratio (a:b:c:d) of catalyst components | 1:3:15:5 | 1:3:15:5 |
| Reaction temperature (° C.) | 80 | 80 |
| Ethylene pressure (Kg/cm²G) | 35 | 35 |
| Residence time (Hr) | 0.5 | 0.5 |
| Contacting method | (1) | (1) |

|  | Example 52 | Example 53 |
|---|---|---|
| Type of solvent (Amount: ml) | HP (750) | HP (750) |
| Amount (mg) of Cr(2EHA)₃ | 22.5 | 22.5 |
| Cr(2EHA)₃ (a) (mmol) | 0.047 | 0.047 |
| Type of nitrogen-containing compound | (1) | (1) |
| Nitrogen-containing compound (b) (mmol) | 0.140 | 0.140 |
| Et₃Al (c) (mmol) | 0.701 | 0.701 |
| Type of halogen-containing compound | (12) | (12) |
| Halogen-containing compound (d) (mmol) | 0.240 | 0.240 |
| Molar ratio (a:b:c:d) of catalyst components | 1:3:15:5 | 1:3:15:5 |
| Reaction temperature (° C.) | 80 | 80 |
| Reaction pressure (Kg/cm²G) | 35 | 35 |
| Concentration of hydrogen (vol%) | 2.8 | 11.0 |
| Residence time (Hr) | 1.0 | 1.0 |
| Contacting method | (1) | (1) |

|  | Example 54 | Example 55 |
|---|---|---|
| Type of solvent (Amount: ml) | HP (750) | HP (750) |
| Amount (mg) of Cr(2EHA)₃ | 22.5 | 22.5 |
| Cr(2EHA)₃ (a) (mmol) | 0.047 | 0.047 |
| Type of nitrogen-containing compound | (1) | (1) |
| Nitrogen-containing compound | 0.140 | 0.140 |

TABLE 1-continued

|  |  |  |
|---|---|---|
| compound (b) (mmol) |  |  |
| Et₃Al (c) (mmol) | 0.701 | 0.701 |
| Type of halogen-containing compound | (12) | (12) |
| Halogen-containing compound (d) (mmol) | 0.240 | 0.240 |
| Molar ratio (a:b:c:d) of catalyst components | 1:3:15:5 | 1:3:15:5 |
| Reaction temperature (° C.) | 80 | 80 |
| Reaction pressure (Kg/cm²G) | 35 | 35 |
| Concentration of hydrogen (vol %) | 23.9 | 0 |
| Residence time (Hr) | 1.0 | 1.0 |
| Contacting method | (1) | (1) |

|  | Example 56 | Example 57 |
|---|---|---|
| Type of solvent (Amount: ml) | HP (5) | HP (5) |
| Amount of Cr(2EHA)₃ (g/hr) | 0.29 | 0.29 |
| Cr(2EHA)₃ (a) (mmol) | 0.60 | 0.06 |
| Type of nitrogen-containing compound | (1) | (1) |
| Nitrogen-containing compound (b) (mmol/Hr) | 1.8 | 1.8 |
| Et₃Al (c) (mmol/Hr) | 9.0 | 9.0 |
| Type of halogen-containing compound | (12) | (12) |
| Halogen-containing compound (d) (mmol/Hr) | 3.0 | 3.0 |
| Molar ratio (a:b:c:d) of catalyst components | 1:3:15:5 | 1:3:15:5 |
| Reaction temperature (° C.) | 80 | 80 |
| Reaction pressure (Kg/cm²G) | 35 | 35 |
| Concentration of hydrogen (vol%) | 2.0 | 0 |
| Residence time (Hr) measured at the outlet | 0.53 | 0.52 |
| Contacting method | (1) | (1) |

TABLE 1-continued

|  | Example 58A | Example 58B | Example 59A | Example 59B |
|---|---|---|---|---|
| Type of solvent (Amount: ml) | HP (750) | HP (10) | HP (750) | HP (20) |
| Amount (mg) of Cr(2EHA)₃ | 22.5 | — | 22.5 | — |
| Cr(2EHA)₃ (a) (mmol) | 0.047 | — | 0.047 | — |
| Type of nitrogen-containing compound | (1) | — | (1) | — |
| Nitrogen-containing compound (b) (mmol) | 0.140 | — | 0.140 | — |
| Et₃Al (c) (mmol) | 0.701 | — | 0.701 | 0.701 |
| Type of halogen-containing compound | (6) | (6) | (6) | (6) |
| Halogen-containing compound (d) (mmol) | 0.094 | 0.094 | 0.094 | 0.094 |
| Molar ratio (a:b:c:d) of catalyst components | 1:3:15:2 | 1:3:15:4 | 1:3:15:2 | 1:3:30:4 |
| Reaction temperature (° C.) | 80 | 80 | 80 | 80 |
| Ethylene pressure (Kg/cm²G) | 35 | 35 | 35 | 35 |
| Residence time (Hr) | 1.0 | 2.0 | 1.0 | 2.0 |
| Contacting method | (1) | — | (1) | — |

|  | Example 60A | Example 60B | Example 61A | Example 61B |
|---|---|---|---|---|
| Type of solvent (Amount: ml) | HP (750) | HP (30) | HP (750) | HP (10) |
| Amount (mg) of Cr(2EHA)₃ | 22.5 | — | 22.5 | — |
| Cr(2EHA)₃ (a) (mmol) | 0.047 | — | 0.047 | — |
| Type of nitrogen-containing compound | (1) | — | (1) | — |
| Nitrogen-containing compound (b) (mmol) | 0.140 | 0.140 | 0.140 | — |
| Et₃Al (c) (mmol) | 0.701 | 0.701 | 0.701 | 0.701 |
| Type of halogen-containing compound | (6) | (6) | (6) | — |
| Halogen-containing compound (d) (mmol) | 0.094 | 0.094 | 0.094 | — |
| Molar ratio (a:b:c:d) of catalyst components | 1:3:15:2 | 1:6:30:4 | 1:3:15:2 | 1:3:30:2 |
| Reaction temperature (° C.) | 80 | 80 | 80 | 80 |
| Ethylene pressure (Kg/cm²G) | 35 | 35 | 35 | 35 |

TABLE 1-continued

|  | | | | |
|---|---|---|---|---|
| Residence time (Hr) | 1.0 | 2.0 | 1.0 | 2.0 |
| Contacting method | (1) | — | (1) | — |

|  | Example 62A | Example 62B | Example 63A | Example 63B |
|---|---|---|---|---|
| Type of solvent (Amount: ml) | HP (750) | — | HP (750) | — |
| Amount (mg) of Cr(2EHA)$_3$ | 22.5 | — | 22.5 | — |
| Cr(2EHA)$_3$ (a) (mmol) | 0.047 | — | 0.047 | — |
| Type of nitrogen-containing compound | (1) | — | (1) | — |
| Nitrogen-containing compound (b) (mmol) | 0.140 | — | 0.140 | — |
| Et$_3$Al (c) (mmol) | 0.701 | — | 0.701 | — |
| Type of halogen-containing compound | (6) | — | (6) | — |
| Halogen-containing compound (d) (mmol) | 0.094 | — | 0.188 | — |
| Molar ratio (a:b:c:d) of catalyst components | 1:3:15:2 | 1:3:15:2 | 1:3:15:4 | 1:3:15:4 |
| Reaction temperature (° C.) | 80 | 80 | 80 | 80 |
| Ethylene pressure (Kg/cm$^2$G) | 35 | 35 | 35 | 35 |
| Residence time (Hr) | 1.0 | 2.0 | 1.0 | 2.0 |
| Contacting method | (1) | — | (1) | — |

|  | Example 64 | | Example 65 | |
|---|---|---|---|---|
|  | First AC | Second AC | First AC | Second AC |
| Type of solvent (Amount: ml) | HP (100) | HP (40) | HP (100) | HP (40) |
| Amount of Cr(2EHA)$_3$ (mg/hr) | 6.0 | — | 6.0 | — |
| Cr(2EHA)$_3$ (a) (mmol/Hr) | 0.012 | — | 0.012 | — |
| Type of nitrogen-containing compound | (1) | — | (1) | — |
| Nitrogen-containing compound (b) (mmol/Hr) | 0.037 | — | 0.037 | — |
| Et$_3$Al (c) (mmol/Hr) | 0.190 | 0.190 | 0.190 | — |
| Type of halogen-containing compound | (6) | (6) | (6) | — |
| Halogen-containing compound (d) (mmol/Hr) | 0.024 | 0.024 | 0.024 | — |
| Molar ratio (a:b:c:d) of catalyst components | 1:3:15:2 | 1:3:30:4 | 1:3:15:2 | 1:3:15:2 |
| Reaction temperature (° C.) | 80 | 80 | 80 | 80 |
| Ethylene pressure (Kg/cm$^2$G) | 35 | 35 | 35 | 35 |
| Residence time (Hr) measured at the outlet | 0.63 | 0.36 | 0.62 | 0.52 |
| Contacting method | (1) | — | (1) | — |

|  | Example 66A | Example 66B | Example 67A | Example 67B |
|---|---|---|---|---|
| Type of solvent (Amount: ml) | HP (750) | HP (750) | HP (750) | HP (750) |
| Amount (mg) of Cr(2EHA)$_3$ | 22.5 | 22.5 | 22.5 | 22.5 |
| Cr(2EHA)$_3$ (a) (mmol) | 0.047 | 0.047 | 0.047 | 0.047 |
| Type of nitrogen-containing compound | (1) | (1) | (1) | (1) |
| Nitrogen-containing compound (b) (mmol) | 0.140 | 0.140 | 0.140 | 0.140 |
| Et$_3$Al (c) (mmol) | 0.701 | 0.941 | 0.701 | 0.701 |
| Type of halogen-containing compound | (12) | (12) | (12) | (12) |
| Halogen-containing compound (d) (mmol) | 0.240 | 0.240 | 0.240 | 0.480 |
| Molar ratio (a:b:c:d) of catalyst components | 1:3:15:5 | 1:3:20:5 | 1:3.:15:5 | 1:3:15:10 |
| Reaction temperature (° C.) | 80 | 80 | 80 | 80 |
| Ethylene pressure (Kg/cm$^2$G) | 35 | 35 | 35 | 35 |
| Residence time (Hr) | 0.5 | 1.0 | 0.5 | 1.0 |
| Contacting method | (1) | (1) | (1) | (1) |

|  | Example 68A | Example 68B | Example 69A | Example 69B |
|---|---|---|---|---|
| Type of solvent (Amount: ml) | HP (750) | HP (750) | HP (750) | HP (750) |
| Amount (mg) of Cr(2EHA)$_3$ | 22.5 | 22.5 | 22.5 | 22.5 |
| Cr(2EHA)$_3$ (a) (mmol) | 0.047 | 0.047 | 0.047 | 0.047 |
| Type of nitrogen-containing compound | (1) | (1) | (1) | (1) |
| Nitrogen-containing compound (b) (mmol) | 0.140 | 0.140 | 0.140 | 0.140 |
| Et$_3$Al (c) (mmol) | 0.701 | 1.402 | 0.701 | 0.701 |
| Type of halogen-containing compound | (12) | (12) | (12) | (12) |

TABLE 1-continued

| | | | | |
|---|---|---|---|---|
| Halogen-containing compound (d) (mmol) | 0.240 | 0.480 | 0.240 | 0.240 |
| Molar ratio (a:b:c:d) of catalyst components | 1:3:15:5 | 1:3:30:10 | 1:3:15:5 | 1:3:15:5 |
| Reaction temperature (° C.) | 80 | 80 | 80 | 80 |
| Ethylene pressure (Kg/cm²G) | 35 | 35 | 35 | 35 |
| Residence time (Hr) | 0.5 | 1.0 | 0.5 | 1.0 |
| Contacting method | (1) | (1) | (1) | (1) |

TABLE 2

| | Example 1 | Example 2 | Example 3 |
|---|---|---|---|
| <Amount (g) of product> | 73.16 | 84.90 | 66.87 |
| <Compositional distribution (wt %)> | | | |
| $C_4$ | 0.01 | 0.04 | 0.30 |
| Total $C_6$ | 93.70 | 92.30 | 86.50 |
| 1-Hexene content (wt %) in $C_6$ | 99.60 | 99.50 | 97.70 |
| $C_8$ | 0.30 | 0.30 | 0.50 |
| $C_{10\ to\ 20}$ | 5.90 | 7.30 | 12.60 |
| $C_{22\ to\ 30}$ | 0.00 | 0.00 | 0.01 |
| By-product PE | 0.02 | 0.02 | 0.04 |
| <Catalytic efficiency> | 54200 | 62900 | 61900 |
| <Catalytic activity> | 108400 | 125800 | 123800 |

| | Example 4 | Example 5 | Example 6 |
|---|---|---|---|
| <Amount (g) of product> | 17.25 | 21.31 | 92.08 |
| <Compositional distribution (wt %)> | | | |
| $C_4$ | 3.60 | 0.10 | 0.06 |
| Total $C_6$ | 9.80 | 94.40 | 90.60 |
| 1-Hexene content (wt %) in $C_6$ | 90.10 | 99.30 | 99.60 |
| $C_8$ | 2.10 | 0.40 | 0.29 |
| $C_{10\ to\ 20}$ | 24.50 | 5.00 | 9.00 |
| $C_{22\ to\ 30}$ | 0.00 | 0.00 | 0.00 |
| By-product PE | 0.10 | 0.07 | 0.07 |
| <Catalytic efficiency> | 15950 | 19750 | 68200 |
| <Catalytic activity> | 31900 | 39500 | 136400 |

| | Example 7 | Example 8 | Example 9 |
|---|---|---|---|
| <Amount (g) of product> | 71.30 | 90.53 | 80.41 |
| <Compositional distribution (wt %)> | | | |
| $C_4$ | 0.13 | 0.30 | 0.01 |
| Total $C_6$ | 91.30 | 91.50 | 92.10 |
| 1-Hexene content (wt %) in $C_6$ | 99.00 | 99.30 | 99.40 |
| $C_8$ | 0.34 | 0.30 | 0.60 |
| $C_{10\ to\ 20}$ | 8.20 | 7.80 | 7.30 |
| $C_{22\ to\ 30}$ | 0.00 | 0.00 | 0.00 |
| By-product PE | 0.01 | 0.01 | 0.02 |

TABLE 2-continued

| | | | |
|---|---|---|---|
| <Catalytic efficiency> | 52800 | 67050 | 59550 |
| <Catalytic activity> | 105600 | 134100 | 119100 |

| | Example 10 | Example 11 |
|---|---|---|
| <Amount (g) of product> | 545.86 | 81.72 |
| <Compositional distribution (wt %)> | | |
| $C_4$ | 0.20 | 0.04 |
| Total $C_6$ | 88.90 | 91.80 |
| 1-Hexene content (wt %) in $C_6$ | 98.10 | 99.20 |
| $C_8$ | 0.50 | 0.30 |
| $C_{10\ to\ 20}$ | 10.30 | 7.80 |
| $C_{22\ to\ 30}$ | 0.00 | 0.00 |
| By-product PE | 0.00 | 0.02 |
| <Catalytic efficiency> | 74400 | 60500 |
| <Catalytic activity> | 148800 | 121000 |

| | Comparative Example 1 | Comparative Example 2 |
|---|---|---|
| <Amount (g) of product> | 15.87 | 4.37 |
| <Compositional distribution (wt %)> | | |
| $C_4$ | 13.70 | 0.40 |
| Total $C_6$ | 56.90 | 94.10 |
| 1-Hexene content (wt %) in $C_6$ | 84.60 | 98.30 |
| $C_8$ | 3.30 | 0.50 |
| $C_{10\ to\ 20}$ | 26.00 | 3.40 |
| $C_{22\ to\ 30}$ | 0.00 | 0.00 |
| By-product PE | 0.10 | 1.50 |
| <Catalytic efficiency> | 11750 | 3235 |
| <Catalytic activity> | 23500 | 6470 |

| | Example 12 | Example 13 | Example 14 |
|---|---|---|---|
| <Amount (g) of product> | 25.7 | 3.33 | 4.57 |
| <Compositional distribution (wt %)> | | | |
| $C_4$ | 0.3 | 3.5 | 0.1 |
| Total $C_6$ | 67.7 | 35.5 | 19.5 |
| 1-Hexene content (wt %) in $C_6$ | 92.6 | 79.9 | 89.1 |
| $C_8$ | 0.4 | 1.0 | — |
| $C_{10\ to\ 20}$ | 29.6 | 27.8 | 5.5 |
| $C_{22\ to\ 30}$ | 0.6 | 0.4 | 0.0 |
| Wax | 0.1 | 0.0 | — |
| By-product PE | 1.3 | 31.7 | 74.8 |
| <Catalytic efficiency> | 23770 | 3080 | 4235 |
| <Catalytic activity> | 47540 | 6160 | 8470 |

| | Example 15 | Example 16 | Example 17 |
|---|---|---|---|
| <Amount (g) of product> | 15.5 | 34.8 | 4.26 |
| <Compositional distribution (wt %)> | | | |
| $C_4$ | 1.5 | 0.2 | 0.2 |
| Total $C_6$ | 70.4 | 65.0 | 66.4 |
| 1-Hexene content (wt %) in $C_6$ | 92.2 | 93.1 | 96.0 |

TABLE 2-continued

| | | | |
|---|---|---|---|
| $C_8$ | 2.0 | 0.3 | 0.5 |
| $C_{10 \text{ to } 20}$ | 23.0 | 33.0 | 9.1 |
| $C_{22 \text{ to } 30}$ | 1.2 | 0.2 | 0.2 |
| Wax | 0.2 | 0.0 | 0.1 |
| By-product PE | 2.2 | 1.2 | 23.5 |
| <Catalytic efficiency> | 14305 | 32180 | 3945 |
| <Catalytic activity> | 28610 | 64360 | 7890 |

| | Example 18 | Example 19 | Example 20 |
|---|---|---|---|
| <Amount (g) of product> | 20.9 | 41.7 | 4.45 |
| <Compositional distribution (wt %)> | | | |
| $C_4$ | 0.2 | 0.1 | 0.3 |
| Total $C_6$ | 74.6 | 68.6 | 86.9 |
| 1-Hexene content (wt %) in $C_6$ | 93.8 | 94.1 | 95.1 |
| $C_8$ | 0.3 | 0.3 | 0.2 |
| $C_{10 \text{ to } 20}$ | 22.8 | 29.7 | 9.3 |
| $C_{22 \text{ to } 30}$ | 0.2 | 0.2 | — |
| Wax | — | 0.00 | — |
| By-product PE | 1.9 | 1.1 | 3.3 |
| <Catalytic efficiency> | 77550 | 38640 | 4125 |
| <Catalytic activity> | 155100 | 77280 | 8250 |

| | Example 21 | Example 22 | Example 23 |
|---|---|---|---|
| <Amount (g) of product> | 5.13 | 15.4 | 26.3 |
| <Compositional distribution (wt %)> | | | |
| $C_4$ | 0.3 | 1.4 | 0.1 |
| Total $C_6$ | 88.1 | 67.6 | 69.3 |
| 1-Hexene content (wt %) in $C_6$ | 95.2 | 93.3 | 94.2 |
| $C_8$ | — | 2.2 | 0.3 |
| $C_{10 \text{ to } 20}$ | 8.8 | 24.3 | 28.6 |
| $C_{22 \text{ to } 30}$ | — | 1.9 | 0.1 |
| Wax | — | 0.6 | — |
| By-product PE | 2.8 | 2.0 | 1.5 |
| <Catalytic efficiency> | 4755 | 14300 | 24315 |
| <Catalytic activity> | 9510 | 28600 | 48630 |

| | Example 24 | Example 25 | Example 26 |
|---|---|---|---|
| <Amount (g) of product> | 5.00 | 9.20 | 33.4 |
| <Compositional distribution (wt %)> | | | |
| $C_4$ | 0.8 | 0.1 | 0.0 |
| Total $C_6$ | 68.5 | 83.2 | 70.4 |
| 1-Hexene content (wt %) in $C_6$ | 92.2 | 95.8 | 94.1 |
| $C_8$ | 0.8 | 0.2 | — |
| $C_{10 \text{ to } 20}$ | 24.3 | 13.4 | 28.7 |
| $C_{22 \text{ to } 30}$ | 0.3 | — | 0.1 |
| Wax | — | — | — |
| By-product PE | 6.8 | 3.1 | 0.8 |
| <Catalytic efficiency> | 4625 | 8515 | 30900 |
| <Catalytic activity> | 9250 | 17030 | 61800 |

| | Example 27 | Example 28 | Example 29 |
|---|---|---|---|
| <Amount (g) of product> | 2.52 | 4.38 | 21.4 |
| <Compositional distribution (wt %)> | | | |
| $C_4$ | 0.3 | 0.2 | 0.0 |
| Total $C_6$ | 85.6 | 83.9 | 73.2 |
| 1-Hexene content (wt %) in $C_6$ | 95.7 | 95.1 | 94.8 |
| $C_8$ | 0.3 | 0.3 | 0.2 |
| $C_{10 \text{ to } 20}$ | 11.1 | 12.1 | 19.6 |
| $C_{22 \text{ to } 30}$ | — | — | 0.0 |
| Wax | — | — | 0.0 |
| By-product PE | 2.8 | 3.4 | 6.8 |
| <Catalytic efficiency> | 2335 | 4060 | 7925 |
| <Catalytic activity> | 4670 | 8120 | 15850 |

| | Example 30 | Example 31 | Example 32 |
|---|---|---|---|
| <Amount (g) of product> | 13.3 | 9.64 | 0.86 |
| <Compositional distribution (wt %)> | | | |
| $C_4$ | 0.4 | 0.4 | 0.0 |
| Total $C_6$ | 74.9 | 48.1 | 38.7 |
| 1-Hexene content (wt %) in $C_6$ | 92.7 | 96.9 | 96.9 |
| $C_8$ | 0.5 | 0.5 | — |
| $C_{10 \text{ to } 20}$ | 20.4 | 6.4 | 2.8 |
| $C_{22 \text{ to } 30}$ | 0.3 | 0.2 | — |
| Wax | 0.1 | — | — |
| By-product PE | 3.4 | 44.5 | 58.0 |
| <Catalytic efficiency> | 12280 | 3570 | 400 |
| <Catalytic activity> | 24560 | 7140 | 800 |

| | Example 33 | Example 34 | Example 35 |
|---|---|---|---|
| <Amount (g) of product> | 3.43 | 2.98 | 3.10 |
| <Compositional distribution (wt %)> | | | |
| $C_4$ | 0.2 | 0.5 | 0.3 |
| Total $C_6$ | 25.6 | 78.4 | 76.1 |
| 1-Hexene content (wt %) in $C_6$ | 95.4 | 95.4 | 95.7 |
| $C_8$ | 0.2 | 0.2 | 0.2 |
| $C_{10 \text{ to } 20}$ | 3.4 | 8.9 | 9.4 |
| $C_{22 \text{ to } 30}$ | 0.1 | — | — |
| Wax | — | — | — |
| By-product PE | 70.4 | 12.0 | 14.0 |
| <Catalytic efficiency> | 3175 | 2760 | 2840 |
| <Catalytic activity> | 6350 | 5520 | 5680 |

| | Example 36 | Example 37 | Example 38 |
|---|---|---|---|
| <Amount (g) of product> | 6.07 | 14.9 | 2.56 |
| <Compositional distribution (wt %)> | | | |
| $C_4$ | 0.1 | 1.0 | 0.7 |
| Total $C_6$ | 83.9 | 72.6 | 78.5 |
| 1-Hexene content (wt %) in $C_6$ | 94.5 | 92.8 | 94.7 |
| $C_8$ | 0.4 | 1.2 | — |
| $C_{10 \text{ to } 20}$ | 12.2 | 22.5 | 8.1 |
| $C_{22 \text{ to } 30}$ | — | 0.6 | — |
| Wax | — | 0.0 | — |
| By-product PE | 3.5 | 2.1 | 12.7 |
| <Catalytic efficiency> | 5620 | 13755 | 2375 |
| <Catalytic activity> | 11240 | 27510 | 4750 |

TABLE 2-continued

|  | Example 39 | Example 40 | Example 41 |
|---|---|---|---|
| <Amount (g) of product> | 9.75 | 19.6 | 5.53 |
| <Compositional distribution (wt %)> | | | |
| $C_4$ | 10.9 | 1.5 | 6.6 |
| Total $C_6$ | 55.0 | 57.7 | 58.2 |
| 1-Hexene content (wt %) in $C_6$ | 88.7 | 88.5 | 88.5 |
| $C_8$ | 3.0 | 1.0 | 3.2 |
| $C_{10\ to\ 20}$ | 23.2 | 21.1 | 24.4 |
| $C_{22\ to\ 30}$ | 0.5 | 1.2 | 0.9 |
| Wax | 0.0 | 0.7 | 0.3 |
| By-product PE | 7.3 | 16.8 | 6.3 |
| <Catalytic efficiency> | 3610 | 18120 | 5120 |
| <Catalytic activity> | 7220 | 36240 | 10240 |

|  | Example 42 | Example 43 | Example 44 |
|---|---|---|---|
| <Amount (g) of product> | 9.02 | 2.46 | 7.11 |
| <Compositional distribution (wt %)> | | | |
| $C_4$ | 5.5 | 0.3 | 9.3 |
| Total $C_6$ | 59.1 | 67.1 | 46.8 |
| 1-Hexene content (wt %) in $C_6$ | 89.9 | 90.4 | 90.6 |
| $C_8$ | 3.3 | 0.6 | 3.5 |
| $C_{10\ to\ 20}$ | 23.1 | 13.3 | 20.1 |
| $C_{22\ to\ 30}$ | 1.1 | — | 1.1 |
| Wax | 0.1 | — | 0.1 |
| By-product PE | 7.8 | 18.7 | 19.1 |
| <Catalytic efficiency> | 8355 | 2280 | 2630 |
| <Catalytic activity> | 16710 | 4560 | 5260 |

|  | Example 45 | Example 46 | Example 47 |
|---|---|---|---|
| <Amount (g) of product> | 24.6 | 12.6 | 10.2 |
| <Compositional distribution (wt %)> | | | |
| $C_4$ | 0.5 | 0.4 | 0.1 |
| Total $C_6$ | 63.3 | 70.2 | 68.6 |
| 1-Hexene content (wt %) in $C_6$ | 91.9 | 91.9 | 92.6 |
| $C_8$ | 0.5 | 0.5 | 1.0 |
| $C_{10\ to\ 20}$ | 29.6 | 21.7 | 23.0 |
| $C_{22\ to\ 30}$ | 0.4 | 0.8 | 0.4 |
| Wax | 0.1 | 0.1 | 0.2 |
| By-product PE | 5.7 | 6.3 | 6.0 |
| <Catalytic efficiency> | 22755 | 11710 | 9470 |
| <Catalytic activity> | 45510 | 23420 | 18940 |

|  | Example 48 | Example 49 |
|---|---|---|
| <Amount (g) of product> | 159.6 | 137.9 |
| <Compositional distribution (wt %)> | | |
| $C_4$ | 0.1 | 0.0 |
| Total $C_6$ | 95.4 | 97.0 |
| 1-Hexene content (wt %) in $C_6$ | 99.1 | 99.5 |
| $C_8$ | 0.4 | 0.5 |
| $C_{10\ to\ 20}$ | 4.0 | 2.5 |
| By-product PE | 0.00 | 0.00 |

TABLE 2-continued

|  | Example 50 | Example 51 |
|---|---|---|
| <Amount (g) of product> | 141.6 | 150.0 |
| <Compositional distribution (wt %)> | | |
| $C_4$ | 0.2 | 0.4 |
| Total $C_6$ | 94.0 | 89.0 |
| 1-Hexene content (wt %) in $C_6$ | 98.1 | 97.6 |
| $C_8$ | 0.5 | 0.7 |
| $C_{10\ to\ 20}$ | 5.2 | 9.8 |
| By-product PE | 0.00 | 0.02 |

|  | Example 52 | Example 53 | Example 54 | Example 55 |
|---|---|---|---|---|
| <Amount (g) of product> | 291.8 | 318.8 | 245.8 | 391.8 |
| <Compositional distribution (wt %)> | | | | |
| $C_4$ | 0.2 | 0.3 | 0.6 | 0.3 |
| Total $C_6$ | 91.4 | 91.2 | 91.4 | 91.1 |
| 1 Hexene content (wt %) in $C_6$ | 98.3 | 98.3 | 98.2 | 98.3 |
| $C_8$ | 0.6 | 0.6 | 0.8 | 0.6 |
| $C_{10\ to\ 20}$ | 7.7 | 7.8 | 8.0 | 7.9 |
| By-product PE | 0.06 | 0.05 | 0.03 | 0.03 |
| Form of By-product PE | Fine powder | Fine powder | Fine powder | Film-like |
| Average molecular weight | 82000 | 48000 | 41000 | 331060 |
| <Catalytic efficiency> | 125277 | 136220 | 105518 | 167422 |

|  | Example 56 | Example 57 |
|---|---|---|
| <Amount (g) of product> | 6.2 | 6.4 |
| <Compositional distribution (wt %)> | | |
| $C_4$ | 0.1 | 0.1 |
| Total $C_6$ | 91.0 | 90.9 |
| 1 Hexene content (wt %) in $C_6$ | 99.5 | 99.5 |
| $C_8$ | 0.4 | 0.4 |
| $C_{10\ to\ 20}$ | 8.5 | 8.6 |
| By-product PE | 0.05 | 0.04 |
| Form of By-product PE | Fine powder | Film-like |
| Average molecular weight | 85000 | 301000 |
| <Catalytic efficiency> | 197957 | 204342 |

|  | Example 58A | Example 58B | Example 59A | Example 59B |
|---|---|---|---|---|
| <Amount (g) of product> | 115.8 | 195.1 | 106.4 | 235.7 |
| <Compositional distribution (wt %)> | | | | |
| $C_4$ | 0.1 | 0.1 | 0.0 | 0.0 |
| Total $C_6$ | 95.5 | 95.9 | 95.8 | 93.3 |
| 1-Hexene content (wt %) in $C_6$ | 98.8 | 99.1 | 98.8 | 99.1 |
| $C_8$ | 0.5 | 0.4 | 0.5 | 0.5 |
| $C_{10\ to\ 20}$ | 3.9 | 3.6 | 3.6 | 5.9 |
| By-product PE | 0.10 | 0.10 | 0.20 | 0.20 |
| <Catalytic efficiency> | 49479 | 83280 | 45449 | 100736 |

|  | Example 60A | Example 60B | Example 61A | Example 61B |
|---|---|---|---|---|
| <Amount (g) of product> | 133.4 | 167.2 | 108.3 | 174.0 |

TABLE 2-continued

| | Compositional distribution (wt %) | | | |
|---|---|---|---|---|
| $C_4$ | 0.0 | 0.1 | 0.3 | 0.5 |
| Total $C_6$ | 95.6 | 95.6 | 93.4 | 92.2 |
| 1-Hexene content (wt %) in $C_6$ | 99.0 | 99.0 | 98.4 | 98.2 |
| $C_8$ | 0.5 | 0.5 | 0.6 | 0.7 |
| $C_{10\ to\ 20}$ | 3.8 | 3.7 | 5.5 | 6.4 |
| By-product PE | 0.14 | 0.14 | 0.06 | 0.08 |
| <Catalytic efficiency> | 57017 | 71448 | 46284 | 74370 |

| | Example 62A | Example 62B | Example 63A | Example 63B |
|---|---|---|---|---|
| <Amount (g) of product> | 120.4 | 123.6 | 103.4 | 128.8 |
| | Compositional distribution (wt %) | | | |
| $C_4$ | 0.4 | 0.1 | 0.0 | 0.0 |
| Total $C_6$ | 95.6 | 95.4 | 96.9 | 97.1 |
| 1-Hexene content (wt %) in $C_6$ | 98.9 | 98.9 | 99.3 | 99.1 |
| $C_8$ | 0.5 | 0.5 | 0.5 | 0.4 |
| $C_{10\ to\ 20}$ | 3.8 | 3.9 | 2.5 | 2.3 |
| By-product PE | 0.0 | 0.0 | 0.12 | 0.18 |
| <Catalytic efficiency> | 51473 | 52807 | 45826 | 57050 |

| | Example 64-1AC | Example 64-2AC | Example 65-1AC | Example 65-2AC |
|---|---|---|---|---|
| <Amount (g) of product> | 95.2 | 187.0 | 96.0 | 101.0 |
| | Compositional distribution (wt %) | | | |
| $C_4$ | 0.0 | 0.0 | 0.0 | 0.00 |
| Total $C_6$ | 93.6 | 93.7 | 94.0 | 94.0 |
| 1-Hexene content (wt %) in $C_6$ | 99.7 | 99.7 | 99.7 | 99.7 |
| $C_8$ | 0.4 | 0.4 | 0.4 | 0.4 |
| $C_{10\ to\ 20}$ | 5.9 | 5.8 | 5.9 | 5.9 |
| By-product PE | 0.06 | 0.06 | 0.06 | 0.06 |
| <Catalytic efficiency> | 146871 | 288580 | 150111 | 155864 |

| | Example 66A | Example 66B | Example 67A | Example 67B |
|---|---|---|---|---|
| <Amount (g) of product> | 223.7 | 495.6 | 225.1 | 450.1 |
| | Compositional distribution (wt %) | | | |
| $C_4$ | 0.3 | 0.1 | 0.3 | 0.1 |
| Total $C_6$ | 91.9 | 92.2 | 91.6 | 93.0 |
| 1-Hexene content (wt %) in $C_6$ | 98.1 | 98.8 | 98.5 | 98.9 |
| $C_8$ | 0.6 | 0.5 | 0.6 | 0.5 |
| $C_{10\ to\ 20}$ | 7.1 | 7.2 | 7.4 | 6.3 |
| By-product PE | 0.17 | 0.08 | 0.12 | 0.10 |
| <Catalytic efficiency> | 95598 | 211795 | 96197 | 192350 |
| <Catalytic efficiency> | 191196 | 211795 | 192394 | 192350 |

| | Example 68A | Example 68B | Example 69A | Example 69B |
|---|---|---|---|---|
| <Amount (g) of product> | 220.5 | 502.3 | 215.8 | 311.3 |
| | Compositional distribution (wt %) | | | |
| $C_4$ | 0.3 | 0.1 | 0.3 | 0.1 |
| Total $C_6$ | 91.5 | 92.5 | 91.0 | 91.8 |
| 1-Hexene content (wt %) in $C_6$ | 98.2 | 98.9 | 97.9 | 98.4 |
| $C_8$ | 0.6 | 0.6 | 0.6 | 0.6 |
| $C_{10\ to\ 20}$ | 7.5 | 6.7 | 7.9 | 7.3 |
| By-product PE | 0.10 | 0.09 | 0.12 | 0.08 |
| <Catalytic efficiency> | 94231 | 214658 | 92222 | 133034 |
| <Catalytic efficiency> | 188462 | 214658 | 184444 | 133034 |

TABLE 3

| | Example 70 | Example 71 |
|---|---|---|
| Type of solvent (Amount: ml) | HP(750) | HP(750) |
| Type of Cr compound | $Cr(2EHA)_3$ | $Cr(2EHA)_3$ |
| Amount (mg) of $Cr(2EHA)_3$ | 22.5 | 22.5 |
| $Cr(2EHA)_3$ (a) (mmol) | 0.047 | 0.047 |
| 2,5-DMPy (b) (mmol) | 0.140 | 0.140 |
| $Et_3Al$ (c) (mmol) | 0.701 | 0.701 |
| Type of halogen-containing compound | TCE | TCE |
| Halogen-containing compound (d) (mmol) | 0.240 | 0.240 |
| Molar ratio (a:b:c:d) of catalyst components | 1:3:15:5 | 1:3:15:5 |
| Water/Al molar ratio | 0.250 | 1.00 |
| Reaction temperature (°C.) | 80 | 80 |
| Ethylene pressure (Kg/cm²G) | 35 | 35 |
| Reaction time (Hr) | 1.0 | 1.0 |
| <Amount (g) of product> | 389.3 | 387.2 |
| | Compositional distribution (wt %) | |
| $C_4$ | 0.2 | 0.3 |
| Total $C_6$ | 91.2 | 93.1 |
| 1-Hexene content (wt %) in $C_6$ | 98.4 | 98.6 |
| $C_8$ | 0.6 | 0.5 |
| $C_{10\ to\ 20}$ | 8.0 | 6.1 |
| By-product PE | 0.02 | 0.03 |
| <Catalytic activity> | 166360 | 165452 |

TABLE 4

| | Example 72 | Example 73 |
|---|---|---|
| Type of solvent (Amount: ml) | HP(750) | HP(750) |
| Type of Cr compound | $Cr(2EHA)_3$ | $Cr(2EHA)$ |
| Amount (mg) of $Cr(2EHA)_3$ | 22.5 | 22.5 |
| $Cr(2EHA)_3$ (a) (mmol) | 0.047 | 0.047 |
| 2,5-DMPy (b) (mmol) | 0.140 | 0.140 |
| $Et_3Al$ (c) (mmol) | 0.701 | 0.701 |
| Type of halogen-containing compound | TCE | TCE |
| Halogen-containing compound (d) (mmol) | 0.240 | 0.240 |
| Molar ratio (a:b:c:d) of catalyst components | 1:3:15:5 | 1:3:15:5 |
| Water/Al molar ratio | 2.00 | 4.00 |
| Reaction temperature (°C.) | 80 | 80 |
| Ethylene pressure (Kg/cm²G) | 35 | 35 |
| Reaction time (Hr) | 1.0 | 1.0 |
| <Amount (g) of product> | 302.0 | 90.1 |
| | Compositional distribution (wt %) | |
| $C_4$ | 0.4 | 0.8 |
| Total $C_6$ | 91.7 | 84.7 |
| 1-Hexene content | 98.6 | 98.8 |

TABLE 4-continued

|  | Example 72 | Example 73 |
|---|---|---|
| (wt %) in $C_6$ | | |
| $C_8$ | 0.5 | 0.5 |
| $C_{10\ to\ 20}$ | 5.9 | 2.9 |
| By-product PE | 1.37 | 11.1 |
| <Catalytic activity> | 129055 | 38494 |

TABLE 5

|  | Example 74 | | | |
|---|---|---|---|---|
| Type of solvent (Amount: ml) | CHX(730) + HP(20) | | | |
| Type of Cr compound | $Cr(2EHA)_3$ | | | |
| Amount (mg) of $Cr(2EHA)_3$ | 22.5 | | | |
| $Cr(2EHA)_3$ (a) (mmol) | 0.047 | | | |
| 2,5-DMPy (b) (mmol) | 0.140 | | | |
| $Et_3Al$ (c) (mmol) | 0.701 | | | |
| Type of halogen-containing compound | 1,1,2,2-Tetrachloroethane | | | |
| Halogen-containing compound (d) (mmol) | 0.093 | | | |
| Molar ratio (a:b:c:d) of catalyst components | 1:3:15:2 | | | |
| Contacting method | (1) | | | |
| Reaction time (Hr) | 0.5 | 1.0 | 1.5 | 2.0 |
| <Amount (g) of product> | 83.9 | 211.0 | 358.0 | 477.8 |
| <Compositional distribution (wt %)> | | | | |
| $C_4$ | 2.2 | 1.0 | 0.7 | 0.8 |
| Total $C_6$ | 81.8 | 87.6 | 89.9 | 90.7 |
| 1-Hexene content (wt %) in $C_6$ | 95.0 | 97.5 | 98.3 | 98.6 |
| $C_8$ | 1.3 | 1.0 | 0.8 | 0.7 |
| $C_{10\ to\ 20}$ | 14.5 | 10.4 | 8.4 | 7.5 |
| $C_{22\ to\ 30}$ | 0 | 0 | 0 | 0 |
| By-product PE | — | — | — | 0.1 |
| <Catalytic efficiency> | 35842 | 90169 | 153141 | 204188 |
| <Catalytic activity> | 71683 | 90169 | 102094 | 102077 |

TABLE 6

|  | Example 75 | | | |
|---|---|---|---|---|
| Type of solvent (Amount: ml) | CHX(730) + HP(20) | | | |
| Type of Cr compound | $Cr(2EHA)_3$ | | | |
| Amount (mg) of $Cr(2EHA)_3$ | 22.5 | | | |
| $Cr(2EHA)_3$ (a) (mmol) | 0.047 | | | |
| 2,5-DMPy (b) (mmol) | 0.140 | | | |
| $Et_3Al$ (c) (mmol) | 0.701 | | | |
| Type of halogen-containing compound | Germanium tetrachloride | | | |
| Halogen-containing compound (d) (mmol) | 0.093 | | | |
| Molar ratio (a:b:c:d) of catalyst components | 1:3:15:2 | | | |
| Contacting method | (1) | | | |
| Reaction time (Hr) | 0.5 | 1.0 | 1.5 | 2.0 |
| <Amount (g) of product> | 149.5 | 194.8 | 208.2 | 267.0 |
| <Compositional distribution (wt %)> | | | | |
| $C_4$ | 0.03 | 0.03 | 0.03 | 0.03 |
| Total $C_6$ | 95.8 | 95.7 | 95.4 | 96.0 |
| 1-Hexene content (wt %) in $C_6$ | 99.2 | 99.3 | 99.4 | 99.4 |
| $C_8$ | 0.5 | 0.5 | 0.5 | 0.4 |
| $C_{10\ to\ 20}$ | 3.4 | 3.5 | 3.8 | 3.3 |
| $C_{22\ to\ 30}$ | 0 | 0 | 0 | 0 |
| By-product PE | — | — | — | 0.15 |
| <Catalytic efficiency> | 63873 | 83230 | 88991 | 114108 |
| <Catalytic activity> | 127745 | 83230 | 59327 | 57054 |

TABLE 7

|  | Example 76 | | | |
|---|---|---|---|---|
| Type of solvent (Amount: ml) | CHX(730) + HP(20) | | | |
| Type of Cr compound | $Cr(2EHA)_3$ | | | |
| Amount (mg) of $Cr(2EHA)_3$ | 22.5 | | | |
| $Cr(2EHA)_3$ (a) (mmol) | 0.047 | | | |
| 2,5-DMPy (b) (mmol) | 0.140 | | | |
| $Et_3Al$ (c) (mmol) | 0.701 | | | |
| Type of halogen-containing compound | Carbon tetrachloride | | | |
| Halogen-containing compound (d) (mmol) | 0.093 | | | |
| Molar ratio (a:b:c:d) of catalyst components | 1:3:15:2 | | | |
| Contacting method | (1) | | | |
| Reaction time (Hr) | 0.5 | 1.0 | 1.5 | 2.0 |
| <Amount (g) of product> | 124.1 | 168.5 | 195.9 | 250.8 |
| <Compositional distribution (wt %)> | | | | |
| $C_4$ | 0.02 | 0.02 | 0.02 | 0.02 |
| Total $C_6$ | 96.2 | 96.2 | 96.0 | 96.1 |
| 1-Hexene content (wt %) in $C_6$ | 99.3 | 99.4 | 99.4 | 99.5 |
| $C_8$ | 0.5 | 0.5 | 0.5 | 0.5 |
| $C_{10\ to\ 20}$ | 2.9 | 2.9 | 3.1 | 3.0 |
| $C_{22\ to\ 30}$ | 0 | 0 | 0 | 0 |
| By-product PE | — | — | — | 0.19 |
| <Catalytic efficiency> | 53020 | 71995 | 83726 | 107176 |
| <Catalytic activity> | 106039 | 71995 | 55817 | 53588 |
| Catalytic efficiency based on one mole of chlorine ($\times 10^6$) | 142 | 194 | 225 | 288 |

TABLE 8

|  | Example 77 | | |
|---|---|---|---|
| Type of solvent (Amount: ml) | CHX(730) + HP(20) | | |
| Type of Cr compound | $Cr(2EHA)_3$ | | |
| Amount (mg) of $Cr(2EHA)_3$ | 22.5 | | |
| $Cr(2EHA)_3$ (a) (mmol) | 0.047 | | |
| 2,5-DMPy (b) (mmol) | 0.140 | | |
| $Et_3Al$ (c) (mmol) | 0.701 | | |
| Type of halogen-containing compound | 1,1,2,2-Tetrachloroethane | | |
| Halogen-containing compound (d) (mmol) | 0.234 | | |
| Molar ratio (a:b:c:d) of catalyst components | 1:3:15:5 | | |
| Contacting method | (1) | | |
| Reaction time (Hr) | 1.0 | 1.5 | 2.0 |
| <Amount (g) of product> | 336.2 | 408.3 | 555.5 |
| <Compositional distribution (wt %)> | | | |
| $C_4$ | 0.1 | 0.1 | 0.2 |
| Total $C_6$ | 91.1 | 91.2 | 92.7 |
| 1-Hexene content (wt %) in $C_6$ | 98.8 | 98.9 | 99.0 |
| $C_8$ | 0.6 | 0.6 | 0.5 |

TABLE 8-continued

|  | Example 77 | | |
|---|---|---|---|
| $C_{10\ to\ 20}$ | 8.0 | 7.9 | 6.5 |
| $C_{22\ to\ 30}$ | 0 | 0 | 0 |
| By-product PE | — | — | 0.1 |
| <Catalytic efficiency> | 143660 | 174500 | 237392 |
| <Catalytic activity> | 143660 | 116333 | 118696 |
| Catalytic efficiency based on one mole of chlorine ($\times 10^6$) | 153 | 186 | 254 |

TABLE 9

|  | Example 78 | | |
|---|---|---|---|
| Type of Solvent (Amount: ml) | HP (750) | | |
| Type of Cr compound | $Cr(2EHA)_3$ | | |
| Amount (mg) of $Cr(2EHA)_3$ | 22.5 | | |
| $Cr(2EHA)_3$ (a) (mmol) | 0.047 | | |
| 2,5-DMPy (b) (mmol) | 0.140 | | |
| $Et_3Al$ (c) (mmol) | 0.701 | | |
| Type of halogen-containing compound | 1,1,2,2-Tetrachloroethane | | |
| Halogen-containing compound (d) (mmol) | 0.234 | | |
| Molar ratio (a:b:c:d) of catalyst components | 1:3:15:5 | | |
| Contacting method | (1) | | |
| Reaction time (Hr) | 1.0 | 1.5 | 2.0 |
| <Amount (g) of product> | 391.8 | 512.9 | 616.1 |
| <Compositional distribution (wt %)> | | | |
| $C_4$ | 0.3 | 0.2 | 0.3 |
| Total $C_6$ | 91.1 | 91.2 | 91.2 |
| 1-Hexene content (wt %) in $C_6$ | 98.3 | 98.6 | 98.8 |
| $C_8$ | 0.6 | 0.5 | 0.5 |
| $C_{10\ to\ 20}$ | 7.9 | 8.0 | 8.0 |
| $C_{22\ to\ 30}$ | 0 | 0 | 0 |
| By-product PE | — | — | — |
| <Catalytic efficiency> | 167442 | 219186 | 263298 |
| <Catalytic activity> | 167442 | 146124 | 131649 |

TABLE 10

|  | Example 79 | | |
|---|---|---|---|
| Type of solvent (Amount: ml) | HP (750) | | |
| Type of Cr compound | $Cr(2EHA)_3$ | | |
| Amount (mg) of $Cr(2EHA)_3$ | 15 | | |
| $Cr(2EHA)_3$ (a) (mmol) | 0.031 | | |
| 2,5-DMPy (b) (mmol) | 0.093 | | |
| $Et_3Al$ (c) (mmol) | 0.470 | | |
| Type of halogen-containing compound | 1,1,2,2-Tetrachloroethane | | |
| Halogen-containing compound (d) (mmol) | 0.156 | | |
| Molar ratio (a:b:c:d) of catalyst components | 1:3:15:5 | | |
| Contacting method | (1) | | |
| Reaction time (Hr) | 1.0 | 1.5 | 2.0 |
| <Amount (g) of product> | 245.4 | 409.8 | 493.9 |
| <Compositional distribution (wt %)> | | | |
| $C_4$ | 0.3 | 0.2 | 0.3 |
| Total $C_6$ | 90.2 | 92.1 | 92.1 |
| 1-Hexene content (wt %) in $C_6$ | 98.1 | 98.6 | 98.8 |
| $C_8$ | 0.7 | 0.6 | 0.6 |
| $C_{10\ to\ 20}$ | 8.7 | 7.0 | 7.0 |
| $C_{22\ to\ 30}$ | 0 | 0 | 0 |
| By-product PE | — | — | 0.024 |
| <Catalytic efficiency> | 157309 | 262723 | 316622 |
| <Catalytic activity> | 157309 | 175149 | 158311 |

TABLE 11

|  | Example 80 | | |
|---|---|---|---|
| Type of solvent (Amount: ml) | CHX (730) + HP (20) | | |
| Type of Cr compound | $Cr(2EHA)_3$ | | |
| Amount (mg) of $Cr(2EHA)_3$ | 22.5 | | |
| $Cr(2EHA)_3$ (a) (mmol) | 0.047 | | |
| 2,5-DMPy (b) (mmol) | 0.140 | | |
| $Et_3Al$ (c) (mmol) | 0.701 | | |
| Type of halogen-containing compound | 1,1,1-Trichloroethane | | |
| Halogen-containing compound (d) (mmol) | 0.093 | | |
| Molar ratio (a:b:c:d) of catalyst components | 1:3:15:2 | | |
| Contacting method | (1) | | |
| Reaction time (Hr) | 1.0 | 1.5 | 2.0 |
| <Amount (g) of product> | 355.4 | 404.7 | 537.4 |
| <Compositional distribution (wt %)> | | | |
| $C_4$ | 0.1 | 0.1 | 0.1 |
| Total $C_6$ | 91.6 | 90.5 | 92.1 |
| 1-Hexene content (wt %) in $C_6$ | 98.6 | 98.8 | 98.9 |
| $C_8$ | 0.5 | 0.5 | 0.4 |
| $C_{10\ to\ 20}$ | 7.9 | 8.9 | 7.4 |
| $C_{22\ to\ 30}$ | 0 | 0 | 0 |
| By-product PE | — | — | 0.01 |
| <Catalytic efficiency> | 151863 | 172928 | 229678 |
| <Catalytic activity> | 151863 | 115285 | 114839 |

TABLE 12

|  | Example 81 | | |
|---|---|---|---|
| Type of solvent (Amount: ml) | CHX (730) + HP (20) | | |
| Type of Cr compound | $Cr(2EHA)_3$ | | |
| Amount (mg) of $Cr(2EHA)_3$ | 22.5 | | |
| $Cr(2EHA)_3$ (a) (mmol) | 0.047 | | |
| 2,5-DMPy (b) (mmol) | 0.140 | | |
| $Et_3Al$ (c) (mmol) | 0.701 | | |
| Type of halogen-containing compound | 1,2,3,4,5,6-Hexachlorocyclohexane | | |
| Halogen-containing compound (d) (mmol) | 0.093 | | |
| Molar ratio (a:b:c:d) of catalyst components | 1:3:15:2 | | |
| Contacting method | (1) | | |
| Reaction time (Hr) | 1.0 | 1.5 | 2.0 |
| <Amount (g) of product> | 423.2 | 544.2 | 650.2 |
| <Compositional distribution (wt %)> | | | |
| $C_4$ | 0.1 | 0.1 | 0.1 |
| Total $C_6$ | 90.6 | 91.1 | 91.4 |
| 1-Hexene content (wt %) in $C_6$ | 98.4 | 98.6 | 98.7 |
| $C_8$ | 0.5 | 0.5 | 0.4 |
| $C_{10\ to\ 20}$ | 8.7 | 8.2 | 8.1 |
| $C_{22\ to\ 30}$ | 0 | 0 | 0 |
| By-product PE | — | — | 0.008 |
| <Catalytic efficiency> | 180866 | 232584 | 277852 |
| <Catalytic activity> | 180866 | 155056 | 138926 |

TABLE 13

| | Example 82 | | |
|---|---|---|---|
| Type of solvent (Amount: ml) | CHX (730) + HP (20) | | |
| Type of Cr compound | $Cr(2EHA)_3$ | | |
| Amount (mg) of $Cr(2EHA)_3$ | 22.5 | | |
| $Cr(2EHA)_3$ (a) (mmol) | 0.047 | | |
| 2,5-DMPy (b) (mmol) | 0.140 | | |
| $Et_3Al$ (c) (mmol) | 0.701 | | |
| Type of halogen-containing compound | Pentachlorocyclopropane | | |
| Halogen-containing compound (d) (mmol) | 0.093 | | |
| Molar ratio (a:b:c:d) of catalyst components | 1:3:15:2 | | |
| Contacting method | (1) | | |
| Reaction time (Hr) | 1.0 | 1.5 | 2.0 |
| <Amount (g) of product> | 251.4 | 297.2 | 401.0 |
| <Compositional distribution (wt %)> | | | |
| $C_4$ | 0.3 | 0.2 | 0.3 |
| Total $C_6$ | 91.9 | 91.7 | 92.7 |
| 1-Hexene content (wt %) in $C_6$ | 98.1 | 98.4 | 98.6 |
| $C_8$ | 0.6 | 0.6 | 0.5 |
| $C_{10\ to\ 20}$ | 7.1 | 7.5 | 6.4 |
| $C_{22\ to\ 30}$ | 0 | 0 | 0 |
| By-product PE | — | — | 0.01 |
| <Catalytic efficiency> | 107423 | 127001 | 171532 |
| <Catalytic activity> | 107423 | 84667 | 85766 |

TABLE 14

| | Example 83 | | |
|---|---|---|---|
| Type of solvent (Amount: ml) | CHX (730) + HP (20) | | |
| Type of Cr compound | $Cr(2EHA)_3$ | | |
| Amount (mg) of $Cr(2EHA)_3$ | 22.5 | | |
| $Cr(2EHA)_3$ (a) (mmol) | 0.047 | | |
| 2,5-DMPy (b) (mmol) | 0.140 | | |
| $Et_3Al$ (c) (mmol) | 0.701 | | |
| Type of halogen-containing compound | Germanium tetrachloride | | |
| Halogen-containing compound (d) (mmol) | 0.093 | | |
| Molar ratio (a:b:c:d) of catalyst components | 1:3:15:2 | | |
| Contacting method | (1) | | |
| Reaction time (Hr) | 1.0 | 1.5 | 2.0 |
| <Amount (g) of product> | 194.8 | 208.2 | 267.0 |
| <Compositional distribution (wt %)> | | | |
| $C_4$ | 0.03 | 0.03 | 0.03 |
| Total $C_6$ | 95.7 | 95.4 | 96.0 |
| 1-Hexene content (wt %) in $C_6$ | 99.3 | 99.4 | 99.4 |
| $C_8$ | 0.5 | 0.5 | 0.4 |
| $C_{10\ to\ 20}$ | 3.5 | 3.8 | 3.3 |
| $C_{22\ to\ 30}$ | 0 | 0 | 0 |
| By-product PE | — | — | 0.15 |
| <Catalytic efficiency> | 83230 | 88991 | 114108 |
| <Catalytic activity> | 83230 | 59327 | 57054 |

TABLE 15

| | Example 84 | | |
|---|---|---|---|
| Type of solvent (Amount: ml) | CHX (730) + HP (20) | | |
| Type of Cr compound | $Cr(2EHA)_3$ | | |
| Amount (mg) of $Cr(2EHA)_3$ | 22.5 | | |
| $Cr(2EHA)_3$ (a) (mmol) | 0.047 | | |
| 2,5-DMPy (b) (mmol) | 0.140 | | |
| $Et_3Al$ (c) (mmol) | 0.701 | | |
| Type of halogen-containing compound | Carbon tetrachloride | | |
| Halogen-containing compound (d) (mmol) | 0.093 | | |
| Molar ratio (a:b:c:d) of catalyst components | 1:3:15:2 | | |
| Contacting method | (1) | | |
| Reaction time (Hr) | 1.0 | 1.5 | 2.0 |
| <Amount (g) of product> | 168.5 | 195.9 | 250.8 |
| <Compositional distribution (wt %)> | | | |
| $C_4$ | 0.02 | 0.02 | 0.02 |
| Total $C_6$ | 96.2 | 96.0 | 96.1 |
| 1-Hexene content (wt %) in $C_6$ | 99.4 | 99.4 | 99.5 |
| $C_8$ | 0.5 | 0.5 | 0.5 |
| $C_{10\ to\ 20}$ | 2.9 | 3.1 | 3.0 |
| $C_{22\ to\ 30}$ | 0 | 0 | 0 |
| By-product PE | — | — | 0.19 |
| <Catalytic efficiency> | 71995 | 83726 | 107176 |
| <Catalytic activity> | 71995 | 55817 | 53588 |

TABLE 16

| Extracting liquid | Catalyst component | Theoretical Value[a] | Extracting layer[b] | Washing liquid[b] | Organic layer[b] |
|---|---|---|---|---|---|
| Ex. 85 Nitric acid 0.5 mol/l | Cr | 7.8 | 6.9 | 0.1 | 0 |
| | Al | 66.9 | 65.5 | 1.1 | 0 |
| | N | 6.9 | — | — | — |
| Ex. 86 Hydrochloric acid 1.0 mol/l | Cr | 7.8 | 6.6 | 0.1 | 0 |
| | Al | 66.9 | 66.0 | 1.5 | 0 |
| | N | 6.9 | 2.3 | 1.6 | 1.0 |
| Ex. 87 Hydrochloric acid 0.01 mol/l | Cr | 7.8 | 6.7 | 0.1 | 0 |
| | Al | 66.9 | 65.3 | 1.3 | 0 |
| | N | 6.9 | 2.0 | 1.7 | 1.5 |

Note)
[a]: The concentration (ppm) of each catalyst component which is contained in the reaction liquid after the removal of a polymer.
[b]: The value obtained by calculating the weight of each catalyst component measured by ICP analysis as the concentration (weight ppm) of each catalyst in 50 ml of the reaction liquid after the removal of a polymer.

TABLE 17

| Extracting liquid | Catalyst component | Theoretical Value[a] | Extracting layer[b] | Washing liquid[b] | Organic layer[b] |
|---|---|---|---|---|---|
| Ex. 88 NaOH 0.8 mol/l | Cr | 7.8 | 6.1 | 0 | 0 |
| | Al | 66.9 | 60.9 | 0.3 | 0 |
| | N | 6.9 | — | 0.8 | 4.7 |
| Ex. 89 NaOH 0.01 mol/l | Cr | 7.8 | 6.0 | 0 | 0 |
| | Al | 66.9 | 59.5 | 0 | 0 |
| | N | 6.9 | — | 0.2 | 5.0 |
| Ex. 90 NaOH 0.8 mol/1 | Cr | 7.8 | 5.2 | — | 0 |
| | Al | 66.9 | 67.1 | — | 0 |
| | N | 6.9 | — | — | 5.5 |

Note)
[a]: The concentration (ppm) of each catalyst component which is contained in the reaction liquid after the removal of a polymer.
[b]: The value obtained by calculating the weight of each catalyst component measured by ICP analysis as the concentration (weight ppm) of each catalyst in 50 ml of the reaction liquid after the removal of a polymer.

TABLE 18

| | Extracting liquid | Catalyst component | Theoretical Value[a] | Extracting layer[b] | Organic layer[b] |
|---|---|---|---|---|---|
| Ex. 91 | Hydrochloric acid 1.4 mol/l | Cr | 29.7 | 13.7 | 15.7 |
| | | Al | 77.1 | 64.8 | 11.6 |
| | | N | 24.8 | 10.4 | 12.4 |
| Ex. 92 | NaOH 1.2 mol/l | Cr | 29.7 | 11.9 | 16.3 |
| | | Al | 77.1 | 77.0 | 0 |
| | | N | 24.8 | 9.8 | 13.3 |

Note)
[a]: The concentration (ppm) of each catalyst component which is contained in the reaction liquid after the removal of a polymer.
[b]: The value obtained by calculating the weight of each catalyst component measured by ICP analysis as the concentration (weight ppm) of each catalyst in 50 ml of the reaction liquid after the removal of a polymer.

TABLE 19

| | Example 93 | Example 94 | Example 95 |
|---|---|---|---|
| Type of solvent (Amount: ml) | CHX (730) + HP (20) | CHX (730) + HP (20) | CHX (730) + HP (20) |
| Type of Cr compound | Cr(2EHA)$_3$ | Cr(2EHA)$_3$ | Cr(2EHA)$_3$ |
| Amount (mg) of Cr(2EHA)$_3$ | 22.5 | 22.5 | 22.5 |
| Cr(2EHA)$_3$ (a) (mmol) | 0.047 | 0.047 | 0.047 |
| 2,5-DMPy (b) (mmol) | 0.140 | 0.140 | 0.140 |
| Et$_3$Al (c) (mmol) | 0.701 | 0.701 | 0.701 |
| Type of halogen-containing compound | Allyl chloride | Allyl chloride | Allyl chloride |
| Halogen-containing compound (d) (mmol) | 0.234 | 0.234 | 0.234 |
| Molar ratio (a:b:c:d) of catalyst components | 1:3:15:5 | 1:3:15:5 | 1:3:15:5 |
| Contacting method | (1) | (1) | (1) |
| Residence time (Hr) | 0.5 | 1.0 | 2.0 |
| <Amount (g) of product> | 123.1 | 161.5 | 232.2 |
| <Compositional distribution (wt %)> | | | |
| C$_4$ | 0.1 | 0.0 | 0.0 |
| Total C$_6$ | 97.6 | 97.1 | 96.6 |
| 1-Hexene content (wt %) in C$_6$ | 99.3 | 99.5 | 99.3 |
| C$_8$ | 0.4 | 0.4 | 0.4 |
| C$_{10\ to\ 20}$ | 1.9 | 2.3 | 2.7 |
| C$_{22\ to\ 30}$ | 0 | 0 | 0 |
| By-product PE | — | — | 0.161 |
| <Catalytic efficiency> | 52607 | 68996 | 99244 |
| Catalytic efficiency based on one mole of chlorine (×10$^6$) | 225 | 295 | 424 |

What is claimed is:

1. A process for producing an α-olefin oligomer, which comprises oligomerizing an α-olefin in a hydrocarbon reaction solvent in the presence of a catalytically effective amount of a chromium-based catalyst system consisting of (a) a chromium compound, (b) a nitrogen-containing compound selected from the group consisting of pyrroles, pyrrole derivatives and compounds represented by the following formula (1-A):

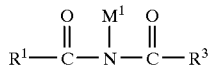  (1-A)

wherein M$^1$ represents a hydrogen atom or a metal element in groups IA, IIA, IB and IIIA of the Periodic Table, each of R$^1$ and R$^3$ represents a hydrogen atom, an alkyl group having 1 to 30 carbon atoms, an alkenyl group having 1 to 30 carbon atoms, or an aralkyl group having 1 to 30 carbon atoms, (c) an alkylaluminum compound of the formula

wherein R$^1$ and R$^2$ are each a hydrocarbon group having 1 to 15 carbon atoms and R$^1$ and R$^2$ may be the same or different from each other; in, n, and p are the numbers defined by $0<m\leq3$, $0\leq n<3$ and $0\leq p<3$ respectively, and m+n+p=3 and (d) a halogen-containing compound containing an element selected from Groups IIIA, IIIB, IVA, IVB, VA, VB or VIB of the Periodic Table, provided that before the α-olefin, the chromium compound (a), the nitrogen-containing compound (b), the alkylaluminum compound (c) and the halogen-containing compound (d) come into contact with each other, the chromium compound (a) and the alkylaluminum compound (c) do not previously contact each other, and when the oligomerization of the α-olefin takes place, the chromium compound (2) and the alkylaluminum compound (c) are supplied simultaneously and separately into the reaction system, wherein the oligomerization is conducted at a temperature of from 0 to 250° C., under a pressure of from 3 to 250 kg/cm$^2$, the α-olefin concentration in the reaction solvent is of from 5 to 100 mol %, the chromium compound concentration is of from $1\times10^{-7}$ to 0.5 mol per liter of the reaction solvent, and the molar ratio of compounds (a):(b):(c):(d) of 1:0.1 to 100:0.1 to 500:0.1 to 100.

2. A process for producing an α-olefin oligomer according to claim 1, wherein said chromium compound (a) is selected from the group consisting of chromium alkoxides, chromium carboxylates, chromium β-diketonates, salts of chromium with anions of β-ketoester, chromium β-ketocarboxylates, amide complexes of chromium, carbonyl complexes of chromium, carbene complexes of chromium, cyclopentadienyl complexes of chromium, alkyl complexes of chromium, phenyl complexes of chromium, chromium halides, ether complexes of chromium halides, ester complexes of chromium halides, ketone complexes of chromium halides, aldehyde complexes of chromium halides, alcohol complexes of chromium halides, amine complexes of chromium halides, nitrile complexes of chromium halides, phosphine complexes of chromium halides and thioether complexes of chromium halides.

3. A process for producing an α-olefin oligomer according to claim 1, wherein said nitrogen-containing compound (b) is selected from the group consisting of pyrroles and derivatives thereof, and said halogen-containing compound (d) is a halogenated hydrocarbon.

4. A process for producing an α-olefin oligomer according to claim 3, wherein said nitrogen-containing compound (b) is selected from the group consisting of pyrrole and 2,5-dimethylpyrrole.

5. A process for producing an α-olefin oligomer according to claim 1, wherein said nitrogen-containing compound (b) is represented by formula (1-A).

6. A process for producing an 60-olefin oligomer according to claim 5, wherein said nitrogen-containing compound (b) is selected from the group consisting of maleimides and derivatives thereof.

7. A process for producing an α-olefin oligomer according to claim 5, wherein said nitrogen-containing compound (b) is selected from the group consisting of maleimides and derivatives thereof, and said halogen-containing compound (d) is an inorganic halide.

8. A process for producing an α-olefin oligomer according to claim 1, wherein said alkylaluminum compound (c) is a trialkylaluminum compound.

9. A process for producing an α-olefin oligomer according to claim 1, wherein said halogen-containing compound (d) contains an element selected from Groups IVA or IVB of the Periodic Table.

10. A process for producing an α-olefin oligomer according to claim 9, wherein said halogen-containing compound (d) is selected from the group consisting of carbon tetrachloride, chloroform, dichloroethane, titanium tetrachloride and germanium tetrachloride.

11. A process for producing an α-olefin oligomer according to claim 1, wherein said halogen-containing compound (d) is a halogenated linear hydrocarbon having at least 2 carbon atoms, and is substituted by at least 3 halogen atoms.

12. A process for producing an α-olefin oligomer according to claim 11, wherein said halogen-containing compound (d) is selected from the group consisting of trichloroethane, tetrachloroethane, pentachloroethane and hexachloroethane.

13. A process for producing an α-olefin oligomer according to claim 1, wherein said halogen-containing compound (d) is a halogenated cyclic hydrocarbon.

14. A process for producing an α-olefin oligomer according to claim 1, wherein said α-olefin is ethylene, and said chromium compound (a) and said alkylaluminum compound (c) contact each other in the presence of ethylene at pressure of about 5 to 100 kg/cm².

15. A process for producing an α-olefin oligomer according to claim 1, wherein said chromium compound (a) and said α-olefin are introduced into a solution containing said nitrogen-containing compound (b), said alkylaluminum compound (c) and said halogen-containing compound (d).

16. A process for producing an α-olefin oligomer according to claim 1, wherein said alkylaluminum compound (c) and said α-olefin are introduced into a solution containing said chromium compound (a), said nitrogen-containing compound (b) and said halogen-containing compound (d).

17. A process for producing an α-olefin oligomer according to claim 1, wherein said alkylaluminum compound (c), said halogen-containing compound (d) and said α-olefin are introduced into a solution containing said chromium compound (a) and said nitrogen-containing compound (b).

18. A process for producing an α-olefin oligomer according to claim 1, wherein said chromium compound (a), said halogen-containing compound (d) and said α-olefin are introduced into a solution containing said nitrogen-containing compound (b) and said alkylaluminum compound (c).

19. A process for producing an α-olefin oligomer according to claim 1, wherein, catalyst components containing at least said alkylaluminum compound (c) and said halogen-containing compound (d), but not containing said chromium compound (a), are first heated to not lower than 100° C. in said reaction solvent, and then said treated catalyst components are contacted with the remaining catalyst components and said α-olefin in the reaction solvent.

20. A process for producing an α-olefin oligomer according to claim 1, wherein 0.1 to 15 vol % of hydrogen exists in a gas phase in a reaction vessel.

21. A process for producing an α-olefin oligomer according to claim 1, the oligomerization of an α-olefin in a reaction solvent is conducted by a semi-batch process or by a continuous process, and at least one catalyst component selected from the group consisting of said nitrogen-containing compound (b), said alkylaluminum compound (c) and said halogen-containing compound (d) is additionally supplied said reaction system.

22. A process for producing an α-olefin oligomer according to claim 1, wherein each of said chromium compound (a), nitrogen-containing compound (b) and said alkylaluminum compound (c) and said halogen-containing compound (d) are continuously supplied into the reaction system.

23. A process for producing an α-olefin oligomer according to claim 1, wherein 0.001 to 1.5 mol of water based on one mol of said alkylaluminum compound (c) is present in the reaction system.

24. A process for producing an α-olefin oligomer according to claim 1, including the further steps of distilling a reaction solution at least containing each of said chromium compound (a), nitrogen compound (b), alkylaluminum compound (c), halogen-containing compound (d) and α-olefin oligomer and separating said α-olefin oligomer from the reaction solution, adding to the recovered solution containing the catalyst components, the alkylaluminum compound (c), the halogen-containing compound (d) or a combination thereof, and recirculating the recovered solution to said reaction system.

25. A process for producing an α-olefin oligomer according to claim 1, wherein the catalyst component or components are removed by contacting a solution after reaction containing said catalyst components and α-olefin oligomer with not more than 2.5 mol/liter of an aqueous acid or alkali solution.

26. A process for producing an α-olefin oligomer according to claim 1, wherein said reaction solvent is an acyclic or alicyclic saturated hydrocarbon having 4 to 10 carbon atoms.

27. A process for producing an α-olefin oligomer according to claim 1, wherein said α-olefin is ethylene, and said α-olefin oligomer is 1-hexene.

28. A process for producing an α-olefin oligomer, which comprises oligomerizing an α-olefin in a hydrocarbon reaction solvent in the presence of a chromium-based catalyst system consisting essentially of (a) a chromium compound, (b) a nitrogen-containing compound selected from the group consisting of pyrroles, pyrrole derivatives and compounds represented by the following formula (1-A):

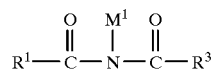

(1-A)

wherein $M^1$ represents a hydrogen atom or a metal element in groups IA, IIA, IB and IIIA of the Periodic Table, each of $R^1$ and $R^3$ represents a hydrogen atom, an alkyl group having 1 to 30 carbon atoms, alkenyl group having 1 to 30 carbon atoms, an aralkyl group having 1 to 30 carbon atoms, (c) an alkylaluminum compound of the formula

wherein $R^1$ and $R^2$ are each a hydrocarbon group having 1 to 15 carbon atoms and $R^1$ and $R^2$ may be the same or different from each other; m, n, and p are the numbers defined by $0<m\leq3$, $0\leq n<3$ and $0\leq p<3$ respectively, and $m+n+p=3$ and (d) a halogen-containing compound containing an element selected from Groups IIIA, IIIB, IVA, IVB, VA, VB or VIB of the Periodic Table, wherein catalyst components containing at least said alkylaluminum compound (c) and said halogen-containing compound (d), and not containing said chromium compound (a) are first heated to not lower than 100° C. in a reaction solvent, and said thus-treated catalyst components are contacted with the remaining catalyst components and said α-olefin in said reaction solvent.

29. A process for producing an α-olefin oligomer according to claim 28, wherein said α-olefin and said chromium compound (a) are introduced into a solution heated to at least 100° C. and which contains said nitrogen-containing compound (b), said alkylaluminum compound (c) and said halogen-containing compound (d).

30. A process for producing an α-olefin oligomer according to claim 28, wherein said α-olefin, said chromium compound (a) and said nitrogen-containing compound (b) are introduced into a solution heated to at least 100° C. and which contains said alkylaluminum compound (c) and said halogen-containing compound (d).

31. A process for producing an α-olefin oligomer which comprises oligomerizing an α-olefin in a hydrocarbon reaction solvent in the presence of a chromium-based catalyst system consisting essentially of (a) a chromium compound, (b) a nitrogen-containing compound selected from the group consisting of pyrroles, pyrrole derivatives and compounds represented by the following formula (1-A):

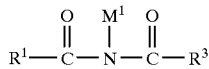

(1-A)

wherein $M^1$ represents a hydrogen atom or a metal element in groups IA, IIA, IB and IIIA of the Periodic Table, each of $R^1$ and $R^3$ represents a hydrogen atom, an alkyl group having 1 to 30 carbon atoms, alkenyl group having 1 to 30 carbon atoms, or an aralkyl group having 1 to 30 carbon atoms, (c) an alkylaluminum compound of the formula

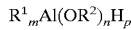

wherein $R^1$ and $R^2$ are each a hydrocarbon group having 1 to 15 carbon atoms and $R^1$ and $R^2$ may be the same or different from each other; m, n, and p are the numbers defined by $0<m\leq 3$, $0\leq n<3$ and $0\leq p<3$ respectively, and $m+n+p=3$ and (d) a halogen-containing compound containing an element selected from Groups IIIA, IIIB, IVA, IVB, VA, VB or VIB of the Periodic Table, wherein said oligomerization of the α-olefin in the reaction solvent is by a semi-batch process or by a continuous process, and at least one catalyst component selected from the group consisting of said nitrogen-containing compound (b), said alkylaluminum compound (c) and said halogen-containing compound (d) is additionally supplied to the reaction system.

32. A process for producing an α-olefin oligomer according to claim 31, wherein said alkylaluminum compound (c) and said halogen-containing compound (d) are additionally supplied to the reaction system.

33. A process for producing an α-olefin oligomer according to claim 31, wherein said alkylaluminum compound (c) is additionally supplied to the reaction system.

34. A process for producing an α-olefin oligomer according to claim 31, wherein said nitrogen-containing compound (b), said alkylaluminum compound (c) and said halogen-containing compound (d) are additionally supplied to the reaction system.

35. A process for producing an α-olefin oligomer according to claim 32, wherein the amount of said nitrogen-containing compound (b), the amount of alkylaluminum compound (c), and the amount of halogen-containing compound (d), are, respectively, not more than 10 mol, not more than 100 mol and not more than 20 mol per addition, and provided that at least one of said compounds (b), (c) and (d) is added per one mol of the chromium compound (a) added at the initiation of the oligomerization.

* * * * *